US007253273B2

(12) United States Patent
Collingwood

(10) Patent No.: US 7,253,273 B2
(45) Date of Patent: Aug. 7, 2007

(54) TREATMENT OF NEUROPATHIC PAIN WITH ZINC FINGER PROTEINS

(75) Inventor: Trevor Collingwood, Novato, CA (US)

(73) Assignee: Sangamo Biosciences, Inc., Richmond, CA (US)

(*) Notice: Subject to any disclaimer, the term of this patent is extended or adjusted under 35 U.S.C. 154(b) by 0 days.

(21) Appl. No.: 11/096,706

(22) Filed: Apr. 1, 2005

(65) Prior Publication Data

US 2005/0245476 A1 Nov. 3, 2005

Related U.S. Application Data

(60) Provisional application No. 60/560,535, filed on Apr. 8, 2004, provisional application No. 60/576,757, filed on Jun. 2, 2004.

(51) Int. Cl.
*C07H 21/02* (2006.01)
*C07H 21/04* (2006.01)

(52) U.S. Cl. .................................................... 536/23.1

(58) Field of Classification Search ................ 536/23.1
See application file for complete search history.

(56) References Cited

U.S. PATENT DOCUMENTS 6,607,882 B1 8/2003 Cox, III et al.
2004/0019006 A1 1/2004 Hayashizaki et al.
2006/0040880 A1 2/2006 Forsayeth et al.

OTHER PUBLICATIONS

Beerli and Barbas, 2002, Nature Biotechnology, 20: 135-141.*
Ginalski et al., 2005, Nucleic Acids Research 33: 1874-1891.*
Jouvenot et al., "Gene Control as a Therapeutic Intervention: Zinc-Finger Protein Transcription Factors as Regulators of the Molecular Determinants of Neuropathic Pain," *Molecular Therapy,* 9(suppl. 1):S90, # 233 (2004).
Tan et al., "Zinc Finger Protein Transcription Factors as Potential Therapeutic Agents for the Treatment of Neuropathic Pain," *Molecular Therapy,* 11(suppl. 1):S250, # 646 (2005).

* cited by examiner

*Primary Examiner*—Anne M. Wehbe'
*Assistant Examiner*—Joanne Hama
(74) *Attorney, Agent, or Firm*—Townsend and Townsend and Crew, LLP

(57) ABSTRACT

A variety of zinc finger proteins (ZFPs) and methods utilizing such proteins are provided for use in treating neuropathic pain. ZFPs that bind to a target site in genes that are aberrantly expressed in subjects having neuropathic pain are described. In addition, ZFPs that bind to a target site in genes expressed at normal levels in subjects experiencing neuropathic pain, modulation of whose expression results in decreased pain perception, are also provided. For example, genes that are over-expressed in the dorsal root ganglia (DRG) of pain patients (e.g., VR1, TRKA and/or Nav1.8) can be repressed, whereas genes that are under-expressed in the same populations can be activated.

3 Claims, 6 Drawing Sheets

TREATMENT OF NEUROPATHIC PAIN WITH ZINC FINGER PROTEINS

CROSS-REFERENCES TO RELATED APPLICATIONS

The present application claims the benefit of U.S. provisional applications 60/560,535 (filed Apr. 8, 2004) and 60/576,757 (filed Jun. 2, 2004), the disclosures of which are incorporated by reference in their entireties for all purposes.

BACKGROUND OF THE INVENTION

Neuropathic pain, also referred to as a chronic pain, is a complex disorder resulting from injury to the nerve, spinal cord or brain. There is evidence that nerve fibers in subjects with neuropathic pain develop abnormal excitability, particularly hyper-excitability. Zimmerman (2001) *Eur J Pharmacol* 429(1-3):23-37. Although the American Pain Society estimates that nearly 50 million Americans are totally or partially disabled by pain, there are currently very few effective, well-tolerated treatments available. Wetzel et al. (1997) Ann Pharmacother 31(9):1082-3). Indeed, existing therapeutics cause a range of undesirable side effects primarily due to the difficulty in developing small-molecule drugs capable of specifically targeting the receptor/channel of choice.

Studies have shown the existence of primary sensory neurons that can be excited by noxious heat, mechanical damage, intense pressure or irritant chemicals, but not by innocuous stimuli such as warmth or light touch. These nociceptors selectively detect pain-inducing stimuli and appear to be distinct from other sensory mechanisms. This suggests that by suppressing the molecular mechanism of nociception it might be possible to limit the perception of painful stimuli without compromising general sensory awareness.

Transduction of noxious stimuli in nociception is mediated by cellular receptors that typically include non-selective ion channels (e.g., vanilloid receptor, VR1), sodium ion channels (e.g., PN3/$NaV_{1.8}$), tyrosine receptor kinases (e.g., TrkA), and GPCRs (e.g., bradykinin receptors). The majority of these receptors are expressed only in neuronal cells that are involved in both chronic and acute nociception, making them possible targets for therapeutic intervention aimed at limiting the pain response. Conventional therapeutic approaches typically focus on attempting to identify ligands that function as antagonists for these receptors. However, a major barrier to this approach is the cross-reactivity of receptor antagonists with other receptors of similar structure that are distinct from the pain-related targets.

The study of the molecular mechanisms triggering neuropathic pain has identified several genes that are abnormally expressed in sensory neurons of the Dorsal Root Ganglion (DRG) in models of neuropathic pain, including Vanilloid Receptor 1 (VR1), a non-selective cationic channel responding to thermal, pH and capsacin stimulation (Hudson et al. (2001) Eur J Neurosci 13(11):2105-2114; Walker et al. (2003) *J. Pharmacol. Exp Ther* 304(1):56-62; Tyrosine kinase A receptor or high-affinity NGF receptor (TRKA), which has been shown to be upregulated in DRG neurons after chronic spinal cord injury (Qiao et al. (2002) J. Comp Neurol. 449(3):217-230); (iii) the sodium channel Nav1.8 (also referred to as PN3 or SCN10A) (Coward et al. (2000) Pain 85(1-2):41-50); and nitric oxide synthase (NOS) (Zimmerman, supra). Lai et al. (2002) Pain 95(1-2):143-152, showed that reduced levels of Nav1.8 correlate with inhibition of neuropathic pain in the rat spinal nerve injury model of chronic pain.

However, the modulation of genes aberrantly expressed in neuropathic pain has not been previously described. Furthermore, the ability to alter expression of these genes may have utility in treating and/or preventing many forms of pain.

BRIEF SUMMARY OF THE INVENTION

A variety of zinc finger proteins (ZFPs) and methods utilizing such proteins are provided for use in treating neuropathic pain. ZFPs that bind to a target site in genes that are aberrantly expressed in subjects having neuropathic pain are described. In addition, ZFPs that bind to a target site in genes expressed at normal levels in subjects experiencing neuropathic pain, modulation of whose expression results in decreased pain perception, are also provided. For example, using the methods and compositions described herein, genes that are over-expressed in the dorsal root ganglia (DRG) of pain patients (e.g., VR1, TRKA and/or Nav1.8) can be repressed, while genes that are under-expressed in the same populations can be activated.

The ZFPs can be fused to a regulatory domain as part of a fusion protein. By selecting either an activation domain or a repression domain for fusion with the ZFP, one can either activate or repress gene expression. Thus, by appropriate choice of the regulatory domain fused to the ZFP, one can selectively modulate the expression of a target gene and hence various physiological processes correlated with neuropathic pain.

By engineering ZFPs that bind to (and modulate expression of) genes encoding molecular targets involved in neuropathic pain to varying degrees, the extent to which a physiological process (e.g., pain) is modulated can be varied, thereby enabling treatment to be tailored. This can be achieved because multiple target sites (e.g., 9, 12 or 18 base pair target sites) in any given gene can be acted upon by the ZFPs provided herein. Thus, in some methods, a plurality of ZFPs (or fusions comprising these ZFPs) is administered. These ZFPs can then bind to different target sites located within a single target gene (e.g., VR1, TRKA, Nav1.8, etc). Alternatively, the ZFPs can bind to target sites in different genes (e.g., two or more of VR1, TRKA, NAV1.8, etc). Such ZFPs can in some instances have a synergistic effect. In certain methods, the plurality of fusion proteins includes different regulatory domains.

Also provided herein are polynucleotides and nucleic acids that encode the ZFPs disclosed herein. Additionally, compositions containing the nucleic acids and/or ZFPs are also provided. For example, certain compositions include a nucleic acid that encodes one of the ZFPs described herein operably linked to a regulatory sequence, combined with a pharmaceutically acceptable carrier or diluent, wherein the regulatory sequence allows for expression of the nucleic acid in a cell. Protein-based compositions include a ZFP as disclosed herein and a pharmaceutically acceptable carrier or diluent.

These and other embodiments will readily occur to those of ordinary skill in the art in view of the disclosure herein.

DETAILED DESCRIPTION OF THE INVENTION

Figure 1:
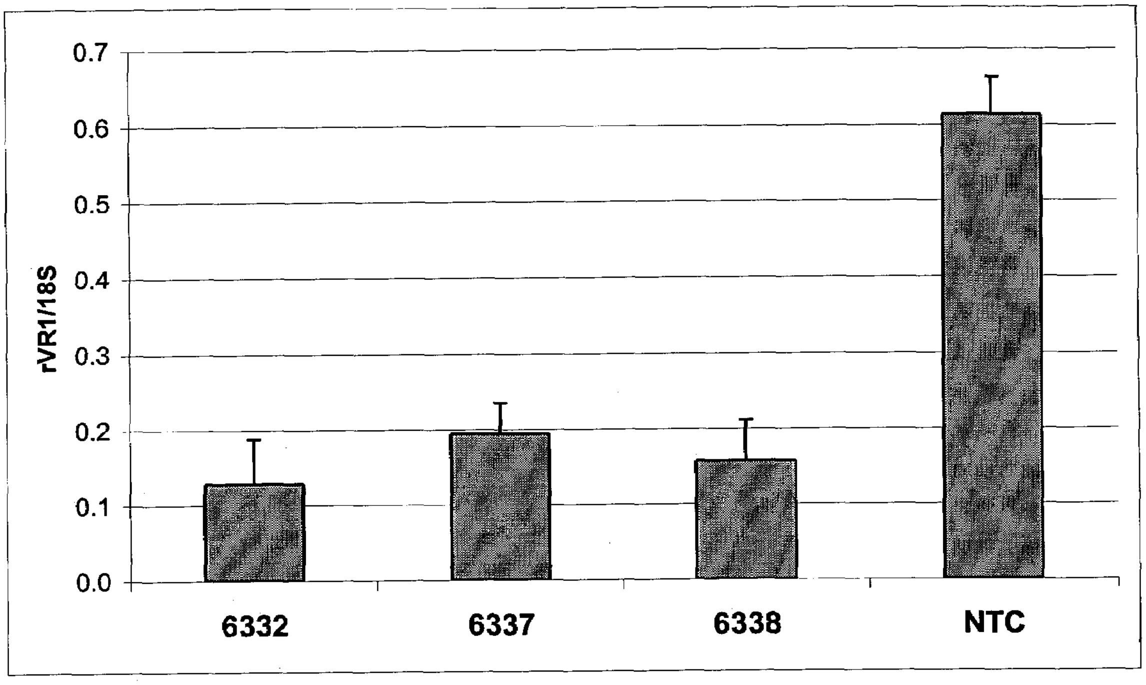
FIG. 1 is a graph depicting repression of VR1 gene expression in rat cells transfected with a plasmid encoding a fusion of a KOX repression domain and a VR1-targeted ZFP (designated 6332, 6337, 6338). The fusion proteins are designated 6332-KOX, 6337-KOX, and 6338-KOX. "NTC" refers to a non-transfected control.

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

I. Definitions

The term "zinc finger protein" or "ZFP" refers to a protein having DNA binding domains that are stabilized by zinc. The individual DNA binding domains are typically referred to as "fingers." A ZFP has least one finger, typically two, three, four, five, six or more fingers. Each finger binds from two to four base pairs of DNA, typically three or four base pairs of DNA. A ZFP binds to a nucleic acid sequence called a target site or target segment. Each finger typically comprises an approximately 30 amino acid, zinc-chelating, DNA-binding subdomain. An exemplary motif characterizing one class of these proteins ($C_2H_2$ class) is -Cys-$(X)_2$-4-Cys-(X)12-His-$(X)_3$-5-His (where X is any amino acid) (SEQ ID NO:1). Additional classes of zinc finger proteins are known and are useful in the practice of the methods, and in the manufacture and use of the compositions disclosed herein (see, e.g., Rhodes et al. (1993) Scientific American 268:56-65 and U.S. Patent Application Publication No. 2003/0108880). Studies have demonstrated that a single zinc finger of this class consists of an alpha helix containing the two invariant histidine residues coordinated with zinc along with the two cysteine residues of a single beta turn (see, e.g., Berg & Shi, Science 271:1081-1085 (1996)).

A "target site" is the nucleic acid sequence recognized by a ZFP. A single target site typically has about four to about ten base pairs. Typically, a two-fingered ZFP recognizes a four to seven base pair target site, a three-fingered ZFP recognizes a six to ten base pair target site, a four-finger ZFP recognizes a 12-14 bp target sequence and a six-fingered ZFP recognizes an 18-20 bp target sequence, which can comprise two adjacent nine to ten base pair target sites or three adjacent 6-7 bp target sites.

A "target subsite" or "subsite" is the portion of a DNA target site that is bound by a single zinc finger, excluding cross-strand interactions. Thus, in the absence of cross-strand interactions, a subsite is generally three nucleotides in length. In cases in which a cross-strand interaction occurs (i.e., a "D-able subsite," see co-owned WO 00/42219) a subsite is four nucleotides in length and overlaps with another 3- or 4-nucleotide subsite.

"Kd" refers to the dissociation constant for a binding molecule, i.e., the concentration of a compound (e.g., a zinc finger protein) that gives half maximal binding of the compound to its target (i.e., half of the compound molecules are bound to the target) under given conditions (i.e., when

[target]<<Kd), as measured using a given assay system (see, e.g., U.S. Pat. No. 5,789,538). The assay system used to measure the Kd should be chosen so that it gives the most accurate measure of the actual Kd of the ZFP. Any assay system can be used, as long is it gives an accurate measurement of the actual Kd of the ZFP. In one embodiment, the Kd for a ZFP is measured using an electrophoretic mobility shift assay ("EMSA"). Unless an adjustment is made for ZFP purity or activity, the Kd calculations may result in an overestimate of the true Kd of a given ZFP. Preferably, the Kd of a ZFP used to modulate transcription of a gene is less than about 100 nM, more preferably less than about 75 nM, more preferably less than about 50 nM, most preferably less than about 25 nM.

A "gene," for the purposes of the present disclosure, includes a DNA region encoding a gene product, as well as all DNA regions that regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. Genes involved in neuropathic pain include, but are not limited to, VR1, TRKA, and Nav1.8.

Furthermore, the term "gene" includes nucleic acids that are substantially identical to a native gene. The terms "identical" or percent "identity," in the context of two or more nucleic acids or polypeptides, refer to two or more sequences or subsequences that are the same or have a specified percentage of nucleotides or amino acid residues that are the same, when compared and aligned for maximum correspondence, as measured using a sequence comparison algorithm such as those described below for example, or by visual inspection.

The phrase "substantially identical," in the context of two nucleic acids or polypeptides, refers to two or more sequences or subsequences that have at least 75%, preferably at least 85%, more preferably at least 90%, 95% or higher or any integral value therebetween nucleotide or amino acid residue identity, when compared and aligned for maximum correspondence, as measured using a sequence comparison algorithm such as those described below for example, or by visual inspection. Preferably, the substantial identity exists over a region of the sequences that is at least about 10, preferably about 20, more preferable about 40-60 residues in length or any integral value therebetween, preferably over a longer region than 60-80 residues, more preferably at least about 90-100 residues, and most preferably the sequences are substantially identical over the full length of the sequences being compared, such as the coding region of a nucleotide sequence for example.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection [see generally, Current Protocols in Molecular Biology, (Ausubel, F. M. et al., eds.) John Wiley & Sons, Inc., New York (1987-1999, including supplements such as supplement 46 (April 1999)]. Use of these programs to conduct sequence comparisons are typically conducted using the default parameters specific for each program.

Another example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. This is referred to as the neighborhood word score threshold (Altschul et al, supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For determining sequence similarity the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, Proc. Natl. Acad. Sci. USA 89:10915 (1989)). 11171 In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another indication that two nucleic acid sequences are substantially identical is that the two molecules hybridize to each other under stringent conditions. "Hybridizes substantially" refers to complementary hybridization between a probe nucleic acid and a target nucleic acid and embraces minor mismatches that can be accommodated by reducing the stringency of the hybridization media to achieve the desired detection of the target polynucleotide sequence. The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

A further indication that two nucleic acid sequences or polypeptides are substantially identical is that the polypeptide encoded by the first nucleic acid is immunologically cross reactive with the polypeptide encoded by the second nucleic acid, as described below.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein that encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid that encodes a polypeptide is implicit in each described sequence.

A polypeptide is typically substantially identical to a second polypeptide, for example, where the two peptides differ only by conservative substitutions. A "conservative substitution," when describing a protein, refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. See, e.g., Creighton (1984) Proteins, W.H. Freeman and Company. In addition, individual substitutions, deletions or additions which alter, add or delete a single amino acid or a small percentage of amino acids in an encoded sequence are also "conservatively modified variations."

A "functional fragment" or "functional equivalent" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid, binding to a regulatory molecule) are well known in the art. Similarly, methods for determining protein function are well known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and PCT WO 98/44350.

The terms "nucleic acid," "polynucleotide," and "oligonucleotide" are used interchangeably and refer to a deoxyribonucleotide or ribonucleotide polymer in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties. In general, an analogue of a particular nucleotide has the same base-pairing specificity; i.e., an analogue of A will base-pair with T. Thus, the term polynucleotide sequence is the alphabetical representation of a polynucleotide molecule. This alphabetical representation can be input into databases in a computer having a central processing unit and used for bioinformatics applications such as functional genomics and homology searching. The terms additionally encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs). The nucleotide sequences are displayed herein in the conventional 5'-3' orientation.

"Chromatin" is the nucleoprotein structure comprising the cellular genome. "Cellular chromatin" comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, $H_2B$, H3 and H4; and linker DNA (of variable length depending on the organism) extends between nucleosome cores. A molecule of histone HI is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome" is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "exogenous molecule" is a molecule that is not normally present in a cell, but can be introduced into a cell by one or more genetic, biochemical or other methods.

Normal presence in the cell is determined with respect to the particular developmental stage and environmental conditions of the cell. Thus, for example, a molecule that is present only during embryonic development of muscle is an exogenous molecule with respect to an adult muscle cell. An exogenous molecule can comprise, for example, a functioning version of a malfunctioning endogenous molecule or a malfunctioning version of a normally functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., protein or nucleic acid (i.e., an exogenous gene), providing it has a sequence that is different from an endogenous molecule. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous molecule" is one that is normally present in a particular cell at a particular developmental stage under particular environmental conditions.

An "endogenous gene" is a gene that is present in its normal genomic and chromatin context. An endogenous gene can be present, e.g., in a chromosome, an episome, a bacterial genome or a viral genome.

The phrase "adjacent to a transcription initiation site" refers to a target site that is within about 50 bases either upstream or downstream of a transcription initiation site. "Upstream" of a transcription initiation site refers to a target site that is more than about 50 bases 5' of the transcription initiation site (i.e., in the non-transcribed region of the gene). "Downstream" of a transcription initiation site refers to a target site that is more than about 50 bases 3' of the transcription initiation site.

A "fusion molecule" is a molecule in which two or more subunit molecules are linked, typically covalently. The subunit molecules can be the same chemical type of molecule, or can be different chemical types of molecules. Examples of the first type of fusion molecule include, but are not limited to, fusion polypeptides (for example, a fusion between a ZFP DNA-binding domain and a transcriptional activation domain) and fusion nucleic acids (for example, a nucleic acid encoding the fusion polypeptide described supra). Examples of the second type of fusion molecule include, but are not limited to, a fusion between a triplex-forming nucleic acid and a polypeptide, and a fusion between a minor groove binder and a nucleic acid.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs that are modified, by processes such as capping, polyadenylation, methylation, and editing, and proteins modified by, for example, methylation, acetylation, phosphorylation, ubiquitination, ADP-ribosylation, myristilation, and glycosylation.

"Gene activation" refers to any process that results in an increase in production of a gene product. A gene product can be either RNA (including, but not limited to, mRNA, rRNA, tRNA, and structural RNA) or protein. Accordingly, gene activation includes those processes that increase transcription of a gene and/or translation of a mRNA. Examples of gene activation processes that increase transcription include, but are not limited to, those that facilitate formation of a transcription initiation complex, those that increase transcription initiation rate, those that increase transcription elongation rate, those that increase processivity of transcription and those that relieve transcriptional repression (by, for example, blocking the binding of a transcriptional repressor). Gene activation can constitute, for example, inhibition of repression as well as stimulation of expression above an existing level. Examples of gene activation processes that increase translation include those that increase translational initiation, those that increase translational elongation and those that increase mRNA stability. In general, gene activation comprises any detectable increase in the production of a gene product, in some instances an increase in production of a gene product by about 2-fold, in other instances from about 2- to about 5-fold or any integer therebetween, in still other instances between about 5- and about 10-fold or any integer therebetween, in yet other instances between about 10- and about 20-fold or any integer therebetween, sometimes between about 20- and about 50-fold or any integer therebetween, in other instances between about 50- and about 100-fold or any integer therebetween, and in yet other instances between 100-fold or more.

"Gene repression" and "inhibition of gene expression" refer to any process that results in a decrease in production of a gene product. A gene product can be either RNA (including, but not limited to, mRNA, rRNA, tRNA, and structural RNA) or protein. Accordingly, gene repression includes those processes that decrease transcription of a gene and/or translation of a mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes that decrease translation include those that decrease translational initiation, those that decrease translational elongation and those that decrease mRNA stability. Transcriptional repression includes both reversible and irreversible inactivation of gene transcription. In general, gene repression comprises any detectable decrease in the production of a gene product, in some instances a decrease in production of a gene product by about 2-fold, in other instances from about 2- to about 5-fold or any integer therebetween, in yet other instances between about 5- and about 10-fold or any integer therebetween, in still other instances between about 10- and about 20-fold or any integer therebetween, sometimes between about 20- and about 50-fold or any integer therebetween, in other instances between about 50- and about 100-fold or any integer therebetween, in still other instances 100-fold or more. In yet other instances, gene repression results in complete inhibition of gene expression, such that no gene product is detectable.

"Modulation" refers to a change in the level or magnitude of an activity or process. The change can be either an increase or a decrease. For example, modulation of gene expression includes both gene activation and gene repression. Modulation can be assayed by determining any parameter that is indirectly or directly affected by the expression of the target gene (e.g. VR1, TRKA, Nav1.8). Such parameters include, e.g., changes in RNA or protein levels, changes in protein activity, changes in product levels, changes in downstream gene expression, changes in reporter gene transcription (luciferase, CAT, β-galactosidase, β-glucuronidase, green fluorescent protein (see, e.g., Mistili & Spector, Nature Biotechnology 15:961-964 (1997)); changes in signal transduction, phosphorylation and dephosphorylation, receptor-ligand interactions, second messenger concentrations (e.g., cGMP, cAMP, IP3, and $Ca^{2+}$), cell growth, and vascularization. These assays can be in vitro, in vivo, and ex vivo. Such functional effects can be measured by any means known to those skilled in the art, e.g., measurement of RNA or protein levels, measurement of RNA stability, identification of downstream or reporter gene expression, e.g., via chemiluminescence, fluorescence, colorimetric reactions, antibody binding, inducible markers, ligand binding assays; changes in intracellular second messengers such as cGMP and inositol triphosphate (IP3); changes in intracellular calcium levels; cytokine release, and the like.

A "regulatory domain" or "functional domain" refers to a protein or a protein domain that has transcriptional modulation activity when tethered to a DNA binding domain, i.e., a ZFP. Typically, a regulatory domain is covalently or non-covalently linked to a ZFP (e.g., to form a fusion molecule) to effect transcription modulation. Regulatory domains can be activation domains or repression domains. Activation domains include, but are not limited to, VP 16, VP64 and the p65 subunit of nuclear factor Kappa-B. Repression domains include, but are not limited to, KRAB, KOX, MBD2B and v-ErbA. Additional regulatory domains include, e.g., transcription factors and co-factors (e.g., MAD, ERD, SID, early growth response factor 1, and nuclear hormone receptors), endonucleases, integrases, recombinases, methyltransferases, histone acetyltransferases, histone deacetylases etc. Activators and repressors include co-activators and co-repressors (see, e.g., Utley et al., Nature 394:498-502 (1998)). Alternatively, a ZFP can act alone, without a regulatory domain, to effect transcription modulation.

The term "operably linked" or "operatively linked" is used with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. An operatively linked transcriptional regulatory sequence is generally joined in cis with a coding sequence, but need not be directly adjacent to it. For example, an enhancer can constitute a transcriptional regulatory sequence that is operatively linked to a coding sequence, even though they are not contiguous.

With respect to fusion polypeptides, the term "operably linked" or "operatively linked" can refer to the fact that each of the components performs the same function in linkage to the other component as it would if it were not so linked. For example, with respect to a fusion polypeptide in which a ZFP DNA-binding domain is fused to a transcriptional activation domain (or functional fragment thereof), the ZFP DNA-binding domain and the transcriptional activation domain (or functional fragment thereof) are in operative linkage if, in the fusion polypeptide, the ZFP DNA-binding domain portion is able to bind its target site and/or its binding site, while the transcriptional activation domain (or functional fragment thereof) is able to activate transcription.

The term "recombinant," when used with reference to a cell, indicates that the cell replicates an exogenous nucleic acid, or expresses a peptide or protein encoded by an exogenous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette," "expression cassette" or "expression construct" is a nucleic acid construct, generated recombinantly or synthetically, that has control elements that are capable of effecting expression of a structural gene that is operatively linked to the control elements in hosts compatible with such sequences. Expression cassettes include at least promoters and optionally, transcription termination signals. Typically, the recombinant expression cassette includes at least a nucleic acid to be transcribed (e.g., a nucleic acid encoding a desired polypeptide) and a promoter. Additional factors necessary or helpful in effecting expression can also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

A "promoter" is defined as an array of nucleic acid control sequences that direct transcription. As used herein, a promoter typically includes necessary nucleic acid sequences near the start site of transcription, such as, in the case of certain RNA polymerase II type promoters, a TATA element, CCAAT box, SP-1 site, etc. As used herein, a promoter also optionally includes distal enhancer or repressor elements, which can be located as much as several thousand base pairs from the start site of transcription. The promoters often have an element that is responsive to transactivation by a DNA-binding moiety such as a polypeptide, e.g., a nuclear receptor, Gal4, the lac repressor and the like.

A "constitutive" promoter is a promoter that is active under most environmental and developmental conditions. An "inducible" promoter is a promoter that is active under certain environmental or developmental conditions.

A "weak promoter" refers to a promoter having about the same activity as a wild type herpes simplex virus ("HSV") thymidine kinase ("tk") promoter or a mutated HSV tk promoter, as described in Eisenberg & McKnight, Mol. Cell. Biol. 5:1940-1947 (1985).

An "expression vector" is a nucleic acid construct, generated recombinantly or synthetically, with a series of specified nucleic acid elements that permit transcription of a particular nucleic acid in a host cell, and optionally integration or replication of the expression vector in a host cell. The expression vector can be part of a plasmid, virus, or nucleic acid fragment, of viral or non-viral origin. Typically, the expression vector includes an "expression cassette," which comprises a nucleic acid to be transcribed operably linked to a promoter. The term expression vector also encompasses naked DNA operably linked to a promoter.

By "host cell" is meant a cell that contains an expression vector or nucleic acid, either of which optionally encodes a ZFP or a ZFP fusion protein. The host cell typically supports the replication or expression of the expression vector. Host cells can be prokaryotic cells such as, for example, *E. coli*, or eukaryotic cells such as yeast, fungal, protozoal, higher plant, insect, or amphibian cells, or mammalian cells such as CHO, HeLa, 293, COS-1, and the like, e.g., cultured cells (in vitro), explants and primary cultures (in vitro and ex vivo), and cells in vivo.

The term "naturally occurring," as applied to an object, means that the object can be found in nature, as distinct from being artificially produced by humans.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins. The polypeptide sequences are displayed herein in the conventional N-terminal to C-terminal orientation.

A "subsequence" or "segment" when used in reference to a nucleic acid or polypeptide refers to a sequence of nucleotides or amino acids that comprise a part of a longer sequence of nucleotides or amino acids (e.g., a polypeptide), respectively.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage.

By an "effective" amount (or "therapeutically effective" amount) of a pharmaceutical composition is meant a sufficient, but nontoxic amount of the agent to provide the desired effect. The term refers to an amount sufficient to treat a subject. Thus, the term therapeutic amount refers to an amount sufficient to remedy a disease state or symptoms, by preventing, hindering, retarding or reversing the progression of the disease or any other undesirable symptoms whatsoever. The term prophylactically effective amount refers to an amount given to a subject that does not yet have the disease, and thus is an amount effective to prevent, hinder or retard the onset of a disease.

II. Overview

A variety of compositions and methods are provided herein for modulating the expression of target genes that are over- or under-expressed in subjects with neuropathic pain. For example, zinc finger proteins that are capable of modulating expression of one or more target genes involved in nerve excitability are provided, thereby modulating chronic pain. Also described are methods for treating neuropathic pain by contacting a cell or population of cells such as in an organism, with one or more zinc finger proteins (ZFPs) that bind to specific sequences in target genes involved in, e.g., nerve excitability and pain. In certain methods, one ZFP is administered and is able to bind to a target site in a single target gene. Other methods involve administering a plurality of different ZFPs that bind to a multiple target sites within a single target gene or, alternatively, within multiple target genes.

Thus, also provided herein are a variety of zinc finger proteins that are engineered to specifically recognize and bind to particular nucleic acid segments (target sites) in genes involved in neuropathic pain, modulate expression of these genes and thereby treat pain. In one embodiment, the ZFPs are linked to regulatory domains to create chimeric transcription factors to activate or repress transcription of one or more genes involved in pain.

With such ZFPs, expression of the target gene(s) can be enhanced; with certain other ZFPs, expression can be repressed. The target site can be adjacent to, upstream of, and/or downstream of the transcription start site (defined as nucleotide +1). As indicated above, one or more ZFPs can be used to modulate expression of one or more target genes. Thus, depending upon the particular ZFP(s) utilized, one can tailor the level at which one or more genes are expressed.

Exemplary target genes include the VR1, TrkA and NaV1.8 genes. The Capsaicin and Vanilloid Receptor (VR1) is located exclusively on small nerve fibers of the dorsal root ganglia (DRG). It is activated by noxious heat, lipid, and the low pH that is often associated with tissue damage. It has been found to be closely associated with other nociceptors (its activity is heightened by nerve growth factor (NGF) and bradykinin) and is therefore regarded as an integrator of the various pain-inducing stimuli. $VR^{-/-}$ mice are viable, normally sentient, and largely indistinguishable from littermates, except for impaired nociception.

The tyrosine Kinase Receptor A (TrkA) is the receptor for NGF, which is a key regulator of nociceptive thresholds. TrkA expression is restricted to the neuronal subpopulation that is principally concerned with nociception. It functions at primary sensory nerve terminals in the DRG to promote thermal hypersensitivity. TrkA both facilitates VR1 function, and requires VR1 for its own function. Adult mice deficient in TrkA exhibit impaired nociception.

The tetrodotoxin-resistant sodium channel ($NaV_{1.8}$, also known as PN3, SNS, and SCN10a) is restricted to the peripheral small diameter sensory neurons in DRGs and is believed to play a unique role in transmission of nociceptive information to the spinal cord. Its expression is also influenced by NGF and TrkA. $NaV_{1.8}^{-/-}$ mice are apparently normal but show deficits in thermoreception and the development of inflammatory pain, and their behavioral responses to noxious mechanical stimulation appear to be completely abolished.

By virtue of the ability of the ZFPs to bind to target sites and influence expression of genes involved in nerve excitability, the ZFPs provided herein can be used to treat a wide range of neuropathic pain. For example, repression of VR1, TRKA and/or Nav1.8 expression can be achieved using the ZFPs described herein, thereby ameliorating or eliminating neuropathic pain. Thus, in certain applications, the ZFPs can be used to repress expression of genes overexpressed in subjects with neuropathic pain, both in vitro and in vivo. Such repression can be utilized, for example, as treatment for chronic pain.

Additional genes whose repression results in reduction of chronic pain include, for example, Dynorphin, NT3, and CCK-b. Conversely, activation of expression of the BDNF, NGF and GDNF genes can also be used for pain reduction. Sah et al. (2003) *Nat. Rev. Drug Disc.* 2: 460-472. Activation and repression of gene expression can be achieved by any method known in the art (e.g., antisense, siRNA). Preferred methods for modulation of gene expression involve the use of engineered zinc finger proteins comprising a transcriptional regulatory domain.

In addition, inactivation of genes involved in pain perception such as, for example, VR1, TrkA and NaV1.8, can be used for treatment of neuropathic pain. In these embodiments, fusion proteins comprising an engineered zinc finger domain and a cleavage domain (or cleavage half-domain) are used for targeted cleavage of a DNA sequence in an endogenous gene involved in neuropathic pain. Targeted cleavage can result in the subsequent introduction of a mutation into the cleaved gene by non-homologous end-joining; alternatively, one or more sequences can be inserted into a gene by homologous recombination following targeted cleavage. See U.S. Patent Application Publication Nos. 2003/0232410; 2005/0026157; 2005/0064474 and WO 03/87341 for additional details relating to targeted cleavage and recombination.

Disclosed herein are compositions and methods for targeted regulation of transcription and targeted DNA cleavage, which are useful, for example, in the treatment of neuropathic pain. These include fusion proteins comprising an engineered zinc finger protein and a functional domain such as, for example, a transcriptional repression domain, a transcriptional activation domain, a nuclease domain or a nuclease half-domain. Suitable functional domains are known in the art and include, without limitation, transcriptional activation domains such as, for example, VP16, VP64 and p65; transcriptional repression domains such as, for example, KOX and v-erbA, cleavage domains such as, for example, HO and cleavage half-domains such as, for example, the cleavage domain of FokI. One or more of the same or different functional domains can be present in a given fusion protein. See co-owned U.S. Patent Application Publication No. 2002/0160940, incorporated by reference, for disclosure of exemplary transcriptional activation and repression domains. Co-owned U.S. Patent Application Publication No. 2005/0064474, incorporated by reference, discloses exemplary cleavage domains and cleavage half-domains.

III. Zinc Finger Proteins for Regulating Gene Expression

A. General

The zinc finger proteins (ZFPs) disclosed herein are proteins that can bind to DNA in a sequence-specific manner. As indicated above, these ZFPs can be used to modulate expression of a target gene (e.g., a gene involved in nerve excitability) in vivo or in vitro and by so doing treat chronic pain. An exemplary motif characterizing one class of these proteins, the $C_2H_2$ class, is -Cys-$(X)_{2-4}$-Cys-$(X)_{12}$-His-$(X)_{3-5}$-His (where X is any amino acid) (SEQ ID NO:1). Several structural studies have demonstrated that the finger domain contains an alpha helix containing the two invariant histidine residues and two invariant cysteine residues in a beta turn coordinated through zinc. However, the ZFPs provided herein are not limited to this particular class. Additional classes of zinc finger proteins are known and can also be used in the methods and compositions disclosed herein. See, e.g., Rhodes, et al. (1993) Scientific American 268:56-65 and U.S. Patent Application Publication No. 2003/0108880. In certain ZFPs, a single finger domain is about 30 amino acids in length. Zinc finger domains are involved not only in DNA-recognition, but also in RNA binding and in protein-protein binding.

The x-ray crystal structure of Zif268, a three-finger domain from a murine transcription factor, has been solved in complex with a cognate DNA-sequence and shows that each finger can be superimposed on the next by a periodic rotation. The structure suggests that each finger interacts independently with DNA over 3 base-pair intervals, with side-chains at positions −1, +2, +3 and +6 on each recognition helix making contacts with their respective DNA triplet subsites. Numbering is with respect to the beginning of the helical portion of the zinc finger; in this numbering scheme, the first (or amino terminal-most) conserved histidine residue of the zinc finger is designated +7. The amino terminus of Zif268 is situated at the 3' end of the DNA strand with which it makes most contacts. Some zinc fingers can bind to a fourth base in a target segment. If the strand with which a zinc finger protein makes most contacts is designated the target strand, some zinc finger proteins bind to a three base triplet in the target strand and a fourth base on the nontarget strand. The fourth base is complementary to the base immediately 3' of the three base subsite.

B. Exemplary ZFPs

ZFPs that bind to particular target sites in genes involved in neuropathic pain are disclosed herein. The target sites can be located upstream or downstream of the transcriptional start site (defined as nucleotide +1). Target sites can include, for example, 9 nucleotides, 12 nucleotides or 18 nucleotides.

The target sites can be located adjacent the transcription initiation site or be located significantly upstream or downstream of the transcription start site. In certain embodiments, a single target site is recognized by the ZFP(s). In other instances, multiple ZFPs can be used, each recognizing different targets in a single gene (e.g., VR1, TRKA or NAV1.8) or in multiple genes.

The ZFPs that bind to these target sites typically include at least one zinc finger but can include a plurality of zinc fingers (e.g., 2, 3, 4, 5, 6 or more fingers). Usually, the ZFPs include at least three fingers. Certain of the ZFPs include four or six fingers. The ZFPs that include three fingers typically recognize a target site that includes 9 or 10 nucleotides; four-finger ZFPs recognize a 12-14-nucleotide target site, and ZFPs having six fingers can recognize target sites that include 18 to 21 nucleotides. The ZFPs can also be fusion proteins that include one or more regulatory domains, which domains can be transcriptional activation or repression domains.

Exemplary zinc finger proteins that bind to a target site in a VR1, Trk-A or NaV1.8 gene are described in detail in the Examples and Tables 2, 3, 4, 5 and 7.

Table 1 shows the nucleotide sequences of target sites for exemplary zinc finger proteins binding to the VR1', Trk-A and NaV 1.8 genes, and the location of each target site relative to the transcription start site. For the human NaV1.8 gene, the transcription start site was estimated, based on homology with the corresponding gene in rat and dog. Negative numbers refer to bp upstream of the transcription start site and positive numbers refer to bp downstream of the transcription start site, where the transcription start site is defined as nucleotide +1. Nucleotides shown in lower case represent nucleotides that are not contacted by a zinc finger. In these cases, the zinc finger protein is designed with a long, non-canonical linker between fingers that bind DNA to either side of the skipped nucleotide. See, for example, U.S. Pat. No. 6,479,626 and WO 01/53480. The genes examined for target sites include rat VR1 (see GenBank accession number NW_047336), rat TRK-A (GenBank No. $NW_{13}047626$), human TrkA (GenBank No. NT_079484) and human NAV1.8 (GenBank No. NT_022517).

TABLE 1

| ZFP | Target site (5'-3') | SEQ ID NO. | GenBank Accession # | Location of Target Site |
|---|---|---|---|---|
| 6144 | TGGGGGTGGGCATTGGCTG | 2 | NW_047336 | -225 (rat VR1) |
| 6149 | GATTGGGATCAGCTCAAG | 3 | NW_047336 | -1093 (rat VR1) |
| 6150 | GTTAAGTGTGCAGTAATGG | 4 | NW_047336 | 186 (rat VR1) |
| 6332 | CTCAAGGACGAGGCAAAG | 5 | NW_047336 | 1105 (rat VR1) |
| 6337 | GATTGGGATCAGCTCAAG | 3 | NW_047336 | 1093 (rat VR1) |
| 6338 | CGGAAGACCCAGAACAAG | 6 | NW_047336 | 381 (rat VR1) |
| 6182 | CCGCGGGGCTAGGCGGTC | 7 | NW_047626 | 106 (rat TRK-A) |
| 6297 | CATGAGGAAGGGGAGCTGG | 8 | NW_047626 | -130 (rat TRK-A) |
| 6584 | TCCCTGCTCCAAGGCAGAG | 9 | NT_022517 | -962 (human NAV1.8) |
| 6585 | GATGGACAACAAGGTTGAG | 10 | NT_022517 | 931 (human NAV1.8) |
| 6586 | GTGAGGGGACAAGCCAAGG | 11 | NT_022517 | -934 (human NAV1.8) |
| 6587 | TTTCAGTGGAAGAAGGGG | 12 | NT_022517 | -459 (human NAV1.8) |
| 6590 | TAATAGAGGAGGAAACTG | 13 | NT_022517 | -788 (human NAV1.8) |
| 6591 | GATCAGGATCAGAGCAGTG | 14 | NT_022517 | 764 (human NAV1.8) |
| 6621 | GCTGAGCCACTGTCACTG | 15 | NT_022517 | -8 (human NAV1.8) |
| 6622 | GGTGAGCGACTGTCACTG | 15 | NT_022517 | -8 (human NAV1.8) |
| 6670 | AAGGCGgGGCCGGGCGGGG | 16 | NT_079484 | -12 to -31 (human TrkA) |
| 6675 | GAGGGGcAAGGCGgGGCCGG | 17 | NT_079484 | -18 to -38 (human TrkA) |
| 6678 | CGCACCCTGCCCCGATGC | 18 | NT_079484 | +116 to +138 (human TrkA) |
| 6679 | GAGTAGGAAGCGgGTGGAG | 19 | NT_079484 | -59 to -90 (human TrkA) |
| 6680 | CTGCCGCCACGGCTCCTC | 20 | NT_079484 | +139 to +157 (human TrkA) |
| 6681 | AGCGGGCGCTGCCCTAGC | 21 | NT_079484 | +487 to +506 (human TrkA) |

Table 2 shows the amino acid sequences included in the recognition region of each finger (F1 through F6) of the various zinc finger proteins designed to bind to a target sequence in rat VR1. The amino acid sequences shown depict residues −1 through +6, as numbered relative to the first amino acid residue in the helical portion of the zinc finger.

TABLE 2

| | F1 | F2 | F3 | F4 | F5 | F6 |
|---|---|---|---|---|---|---|
| 6144 | RSDSLSR (SEQ ID NO:22) | NNDHRKT (SEQ ID NO:23) | TREDLKR (SEQ ID NO:24) | RSDHLSR (SEQ ID NO:25) | RSDHLSN (SEQ ID NO:26) | RSDHRTN (SEQ ID NO:27) |
| 6149 | RSDDLSV (SEQ ID NO:28) | TSSNRTK (SEQ ID NO:29) | RNDMLNE (SEQ ID NO:30) | TSSNLSR (SEQ ID NO:31) | RSDHLST (SEQ ID NO:32) | TSSNRTK (SEQ ID NO:29) |
| 6150 | RSDHLSQ (SEQ ID NO:33) | TSSNRIT (SEQ ID NO:34) | RSDNLSQ (SEQ ID NO:35) | RSNARTK (SEQ ID NO:36) | RSDNLST (SEQ ID NO:37) | HNATRIN (SEQ ID NO:38) |
| 6332 | RSDNLST (SEQ ID NO:37) | QSATRTK (SEQ ID NO:39) | RSDNLST (SEQ ID NO:37) | DSANRIK (SEQ ID NO:40) | RSDDLSV (SEQ ID NO:28) | TSSNRTK (SEQ ID NO:29) |

TABLE 2-continued

| | F1 | F2 | F3 | F4 | F5 | F6 |
|---|---|---|---|---|---|---|
| 6337 | RSDDLSV (SEQ ID NO:28) | TSSNRTK (SEQ ID NO:29) | RSDALSE (SEQ ID NO:41) | TSSSRKK (SEQ ID NO:42) | TKLHLIE (SEQ ID NO:43) | QSANLSR (SEQ ID NO:44) |
| 6338 | RSDALSV (SEQ ID NO:45) | DNANRIT (SEQ ID NO:46) | RSDNLSE (SEQ ID NO:47) | ASKTRTN (SEQ ID NO:48) | RSDNLSV (SEQ ID NO:49) | RNAHRIN (SEQ ID NO:50) |

Table 3 shows the amino acid sequences included in the recognition region of each finger (F1 through F6) of the zinc finger proteins designed to bind to a target sequence in rat Trk-A. The amino acid sequences shown depict residues −1 through +6, as numbered relative to the first amino acid residue in the helical portion of the zinc finger.

TABLE 3

| | F1 | F2 | F3 | F4 | F5 | F6 |
|---|---|---|---|---|---|---|
| 6182 | DSRSLTE (SEQ ID NO:51) | RRDDLSR (SEQ ID NO:52) | RSDHLSQ (SEQ ID NO:33) | DNSHRTR (SEQ ID NO:53) | RSDHLSE (SEQ ID NO:54) | RNRDRIT (SEQ ID NO:65) |
| 6297 | RSDHLSE (SEQ ID NO:54) | RSSNRIK (SEQ ID NO:56) | RSDDLSR (SEQ ID NO:57) | RNDNRIT (SEQ ID NO:58) | RSDHLSQ (SEQ ID NO:33) | TSQNRKN (SEQ ID NO:59) |

Table 4 shows the amino acid sequences included in the recognition region of each finger (F1 through F6) of the various zinc finger proteins designed to bind to a target sequence in human NaV1.8. The amino acid sequences shown depict residues −1 through +6, as numbered relative to the first amino acid residue in the helical portion of the zinc finger.

TABLE 4

| ZFP | F1 | F2 | F3 | F4 | F5 | F6 |
|---|---|---|---|---|---|---|
| 6584 | RSDALSE (SEQ ID NO:41) | QNATRTK (SEQ ID NO:60) | RSDNLSN (SEQ ID NO:61) | TNSNRIK (SEQ ID NO :62) | RSDSLSA (SEQ ID NO:63) | DRSSRTK (SEQ ID NO:64) |
| 6585 | RSDNLST (SEQ ID NO:37) | HSHARIK (SEQ ID NO:65) | RSDALSV (SEQ ID NO:45) | DNANRIT (SEQ ID NO:46) | TSDSLTE (SEQ ID NO:66) | NRDNLSR (SEQ ID NO:67) |
| 6586 | RSDHLSA (SEQ ID NO:68) | QSATRIT (SEQ ID NO:69) | RSDALSV (SEQ ID NO:45) | DNANRTK (SEQ ID NO:70) | RSDHLSQ (SEQ ID NO:33) | RSAVRKN (SEQ ID NO:71) |
| 6587 | RSDHLSE (SEQ ID NO:54) | RNDNRKT (SEQ ID NO:72) | RSDNLSE (SEQ ID NO:47) | RNAHRIN (SEQ ID NO:50) | RSDHLSE (SEQ ID NO:54) | TSSSRKN (SEQ ID NO:73) |
| 6590 | RSDVLSE (SEQ ID NO:74) | QRNHRTT (SEQ ID NO:75) | RSDHLSN (SEQ ID NO:26) | RSDHRTN (SEQ ID NO:27) | RSDHLST (SEQ ID NO:32) | NRSNRTT (SEQ ID NO:76) |
| 6591 | RSDVLSK (SEQ ID NO:77) | QNATRIK (SEQ ID NO:78) | RNDMLNE (SEQ ID NO:30) | TSSNLSR (SEQ ID NO:31) | RSDALSE (SEQ ID NO:41) | TSSSRKK (SEQ ID NO:42) |
| 6621 | RSDALSE (SEQ ID NO:41) | RSSDRTK (SEQ ID NO:79) | RSDTLST (SEQ ID NO:80) | QKATRTT (SEQ ID NO:81) | HSADLTQ (SEQ ID NO:82) | QSSDLSR (SEQ ID NO:83) |
| 6622 | RSDALSE (SEQ ID NO:41) | RSSDRTK (SEQ ID NO:79) | RSDTLST (SEQ ID NO:80) | QKATRTT (SEQ ID NO:81) | RSDTLST (SEQ ID NO:80) | HSDTRKK (SEQ ID NO:84) |

Table 5 shows the amino acid sequences included in the recognition region of each finger (F1 through F6) of the various zinc finger proteins designed to bind to a target sequence in the human TrkA gene. The amino acid sequences shown depict residues −1 through +6, as numbered relative to the first amino acid residue in the helical portion of the zinc finger.

TABLE 5

| | F1 | F2 | F3 | F4 | F5 | F6 |
|---|---|---|---|---|---|---|
| 6670 | RSDHLSN (SEQ ID NO:26) | RNDDRKK (SEQ ID NO:85) | RSDHLSE (SEQ ID NO:54) | NSSSRIK (SEQ ID NO:86) | RSDDLSR (SEQ ID NO:57) | RNDNRIT (SEQ ID NO:58) |
| 6675 | RSDHLSE (SEQ ID NO:54) | NSSSRIK (SEQ ID NO:86) | RSDDLSR (SEQ ID NO:57) | RNDNRIT (SEQ ID NO:58) | RSDHLSE (SEQ ID NO:54) | RNDNRKR (SEQ ID NO:87) |
| 6678 | RKDDLIR (SEQ ID NO:88) | TSSSLSR (SEQ ID NO:89) | RSDNLSA (SEQ ID NO:90) | RSQNRTR (SEQ ID NO:91) | RSDDLSK (SEQ ID NO:92) | QSATRTK (SEQ ID NO:39) |
| 6679 | RSDNLSR (SEQ ID NO:93) | RSDARTN (SEQ ID NO:94) | RSDDLSR (SEQ ID NO:57) | QSANRTK (SEQ ID NO:95) | RSDNLST (SEQ ID NO:37) | NNNSRKT (SEQ ID NO:96) |
| 6680 | RSDNLSA (SEQ ID NO:90) | RSQNRTR (SEQ ID NO:91) | RSDHLSQ (SEQ ID NO:33) | RKDTRTN (SEQ ID NO:97) | RSDNLSR (SEQ ID NO:93) | DNNARLN (SEQ ID NO:98) |
| 6681 | MRADLIR (SEQ ID NO:99) | RSDDLSR (SEQ ID NO:57) | RNTDLIR (SEQ ID NO:100) | TSSDLSR (SEQ ID NO:101) | RSDHLSQ (SEQ ID NO:33) | ASSTRTK (SEQ ID NO:102) |

As noted above, the target sites may be any length, but are preferably 9-10, 12-14, or 18-21 nucleotides in length.

Thus, as indicated herein, one or more ZFPs described herein can be utilized to modulate expression of one or more genes involved in neuropathic pain, and by so doing treat this pain. By judicious selection of various ZFPs and/or combinations thereof, one can tailor targeted gene modulation and, accordingly, tailor treatment for neuropathic pain.

C. Zinc Finger Proteins Targeted to the PN3 Gene

The methods for pain therapy and analgesia disclosed herein involve regulation of the expression of, inter alia, the endogenous cellular gene encoding PN3 (also known as NaV1.8) by expressing, in one or more cells of a subject, a fusion protein that binds to a target sequence in the PN3 gene and represses its transcription. Such a fusion protein can be expressed in a cell by introducing into the cell a nucleic acid (DNA or RNA) that encodes the protein, or by introducing the protein directly into the cell. Nucleic acids and/or proteins can also administered to a subject (see below) such that the nucleic acid or protein enters one or more cells of the subject In addition, nucleic acids and/or proteins can be introduced ex vivo into cells which have been isolated from a subject, said cells being returned to the subject after introduction of the nucleic acid and/or protein and optional incubation.

In certain embodiments, a fusion protein as described above comprises a DNA-binding domain and a functional domain (e.g., a transcriptional activation domain or a transcriptional repression domain). The DNA-binding domain can be an engineered zinc finger binding domain as described, for example, in co-owned U.S. Pat. Nos. 6,453,242; 6,534,261; 6,607,882; 6,785,613; 6,794,136 and 6,824,978. See also, for example, U.S. Pat. Nos. 5,5,789,538; 6,007,988; 6,013,453; 6,140,466; 6,242,568; 6,410,248; 6,479,626; 6,746,838 and 6,790,941.

The DNA-binding domain can bind to any sequence, in the transcribed or non-transcribed region of the PN3 gene, or to any other sequence, as long as transcription of the PN3 gene is regulated. Methods for selecting target sites for binding by zinc finger proteins are disclosed in co-owned U.S. Pat. No. 6,453,242. In certain embodiments, the target site is in an accessible region of cellular chromatin as described, for example, in co-owned U.S. Patent Application Publication No. 2002/0064802 A1.

For those embodiments in which the DNA-binding domain is an engineered zinc finger binding domain, the zinc finger domain is engineered to bind a specific target site. The binding domain contains a plurality of zinc fingers (e.g., 2, 3, 4, 5, 6 or more zinc fingers). In general, an individual zinc finger binds a subsite of 3-4 nucleotides. The subsites can be contiguous in a target site (and are in some cases overlapping); alternatively a subsite can be separated from an adjacent subsite by gaps of one, two three or more nucleotides. Binding to subsites separated by a gap of one or more nucleotides is facilitated by the use of non-canonical, longer linker sequences between adjacent zinc fingers. See, for example, U.S. Pat. No. 6,479,626 and U.S. Patent Application Publication Nos. 2002/0173006 and 2003/0119023.

Exemplary target sites for zinc finger proteins regulating PN3 expression are shown in Table 6. In this table, the target sites are depicted as being made up of 3-nucleotide subsites. Nucleotides comprising the subsites, which are contacted by the zinc fingers, are shown in uppercase. Nucleotides between subsites, which are not contacted by a zinc finger, are shown in lowercase. Numbers in the column labeled "Location" refer to the distance, in nucleotides, between the near edge of the target site and the first nucleotide of the initiation codon for the PN3 gene. This nucleotide, "A" in the sequence "ATG," is located at position 38810505 on the minus strand of human chromosome 3 (i.e., the "T" of the ATG codon is located at position 38810504). See *Homo sapiens* Genome (build 35.1), NCBI.

Exemplary zinc finger binding domains that bind to these target sites are shown in Table 7. The table shows the amino acids sequence of the seven-residue recognition region of each zinc finger (amino acid residues −1 through +6 with respect to the start of the helical portion of the zinc finger), for each of the six-finger proteins.

TABLE 6

| ZFP | Target Sequence | | Location |
|---|---|---|---|
| 6584 | TCCCTGcTCGAAGGCACAG | (SEQ ID NO:9) | -23238 |
| 6585 | GATGGAcAACAAGGTTGAG | (SEQ ID NO:10) | -21327 |
| 6586 | GTGAGGgGACAAGCCAAGG | (SEQ ID NO:11) | -23210 |
| 6587 | TTTCAGTGGAAGAAGGGG | (SEQ ID NO:12) | -22734 |
| 6588 | AGTAAGGATCAGGATCAG | (SEQ ID NO:103) | -21500 |
| 6589 | CCACTGTCACTGAGGAGG | (SEQ ID NO:104) | -22277 |
| 6590 | TAATAGAGGAGGAAACTG | (SEQ ID NO:13) | -23063 |
| 6591 | GATCAGGATCAGaGCAGTG | (SEQ ID NO:14) | -21494 |
| 6592 | CCTATGGCCCTGtGGACAG | (SEQ ID NO:105) | -22946 |
| 6595 | GATCAGGATCAGaGCAGTG | (SEQ ID NO:14) | -21494 |
| 6596 | GGGAGGGGTAGGtGGAGGA | (SEQ ID NO:106) | -22972 |
| 6609 | GGAGGGgTAGGTGGAGGAG | (SEQ ID NO:107) | -22973 |
| 6610 | AAGGGGTCCCAGGCGAAG | (SEQ ID NO:108) | -22998 |
| 6612 | CAAAAGGGAGGGgTAGGTG | (SEQ ID NO:109) | -22967 |
| 6613 | AGGGAGGGGTAGGTGGAG | (SEQ ID NO:110) | -22970 |
| 6615 | AGGGAGGGGTAGGTGGAG | (SEQ ID NO:110) | -22970 |
| 6616 | GCATGGTCTCCGGGTCAG | (SEQ ID NO:111) | -21585 |
| 6617 | TCTCTGGGTCAGgGTTCCA | (SEQ ID NO:112) | -23149 |
| 6618 | GGAGGGgTAGGTGgAGGAGG | (SEQ ID NO:113) | -22974 |
| 6619 | AGTAAGGATCAGGATCAG | (SEQ ID NO:103) | -21500 |
| 6620 | GAGGGGTAGGTGgAGGAGG | (SEQ ID NO:114) | -22974 |
| 6621 | GCTGAGCCACTGTCACTG | (SEQ ID NO:15) | -22283 |
| 6622 | GCTGAGCCACTGTCACTG | (SEQ ID NO:15) | -22283 |
| 6623 | GGCCTGgAGTGGGgTCCAAG | (SEQ ID NO:115) | -21417 |

TABLE 6-continued

| ZFP | Target Sequence | | Location |
|---|---|---|---|
| 6626 | AGGGAGgGGTAGGtGGAGGA | (SEQ ID NO:116) | -22972 |
| 6627 | TCACTGaGGAGGAGAAACG | (SEQ ID NO:117) | -22271 |
| 6669 | GATGAGGATCAGaGCAGTG | (SEQ ID NO:14) | -21494 |
| 7231 | TCCATGaACTAGGaAATATG | (SEQ ID NO:118) | -837 |
| 7232 | GATAAGGGTGAGGGAGTG | (SEQ ID NO:119) | -639 |
| 7233 | GCAGGGGAATGGGTTCCT | (SEQ ID NO:120) | -177 |
| 7234 | TCCTGGGAGGAGcCAAGTG | (SEQ ID NO:121) | -162 |
| 7235 | GAAGAAgAATGAGAAGATG | (SEQ ID NO:122) | 3 |
| 7236 | AAGAAGAATGAGAAGATG | (SEQ ID NO:123) | 3 |
| 7237 | CCGGAGTCACTGGTGGAG | (SEQ ID NO:124) | 69 |
| 7238 | GCATAGGGAGCAGAAGGA | (SEQ ID NO:125) | 137 |
| 7239 | GGAGGCCGCAGGcCAGAGG | (SEQ ID NO:126) | 564 |
| 7240 | TAGTGGGTTTATAAAATG | (SEQ ID NO:127) | 727 |
| 7241 | CTACTGgAATGTGTGCCTG | (SEQ ID NO:128) | 864 |
| 7276 | AAGAAGGCTGGAgACACAG | (SEQ ID NO:129) | -904 |
| 7277 | AGACTGAACCTGGAGGTC | (SEQ ID NO:130) | -567 |
| 7278 | AACTTGGAGGTCCAAATG | (SEQ ID NO:131) | -495 |
| 7279 | AATCTGGTGGTGGTGGTA | (SEQ ID NO:132) | -306 |
| 7280 | CCCAGGGCCAAGGAGGAC | (SEQ ID NO:133) | 360 |
| 7281 | GCAGAGcTTTCAGGGAAAG | (SEQ ID NO:134) | 525 |

TABLE 7

| ZFP | F1 | F2 | F3 | F4 | F5 | F6 |
|---|---|---|---|---|---|---|
| 6584 | RSDALSE (SEQ ID NO:41) | QNATWL7K (SEQ ID NO:60) | RSDNLSN (SEQ ID NO:61) | TNSNRIK (SEQ ID NO:62) | RSDSLSA (SEQ ID NO:63) | DRSSRTK (SEQ ID NO:64) |
| 6585 | RSDNLST (SEQ ID NO:37) | HSHARIK (SEQ ID NO:65) | RSDALSV (SEQ ID NO:45) | DNANRIT (SEQ ID NO:46) | TSDSLTE (SEQ ID NO:66) | NRDNLSR (SEQ ID NO:67) |
| 6586 | RSDHLSA (SEQ ID NO:68) | QSATRIT (SEQ ID NO:69) | RSDALSV (SEQ ID NO:45) | DNANRTK (SEQ ID NO:70) | RSDHLSQ (SEQ ID NO:33) | RSAVRKN (SEQ ID NO:71) |
| 6587 | RSDHLSE (SEQ ID NO:54) | RNDNRKT (SEQ ID NO:72) | RSDNLSE (SEQ ID NO:47) | RNAHRIN (SEQ ID NO:50) | RSDHLSE (SEQ ID NO:54) | TSSSRKN (SEQ ID NO:73) |
| 6588 | RNDMLNE (SEQ ID NO:30) | TSSNLSR (SEQ ID NO:31) | RSDALSE (SEQ ID NO:41) | TSSSRKK (SEQ ID NO:42) | RSDNLSV (SEQ ID NO:49) | ANHHRIN (SEQ ID NO:135) |
| 6589 | RSDHLSN (SEQ ID NO:26) | RSDHRTN (SEQ ID NO:27) | RSDALSE (SEQ ID NO:41) | RSSDRTK (SEQ ID NO:79) | RSDTLST (SEQ ID NO:80) | QKATRTT (SEQ ID NO:81) |

TABLE 7-continued

| ZFP | F1 | F2 | F3 | F4 | F5 | F6 |
|---|---|---|---|---|---|---|
| 6590 | RSDVLSE (SEQ ID NO:74) | QRNHRTT (SEQ ID NO:75) | RSDHLSN (SEQ ID NO:26) | RSDHRTN (SEQ ID NO:27) | RSDHLST (SEQ ID NO:32) | NRSNRTT (SEQ ID NO:76) |
| 6591 | RSDVLSK (SEQ ID NO:77) | QNATRIK (SEQ ID NO:78) | RNDMLNE (SEQ ID NO:30) | TSSNLSR (SEQ ID NO:31) | RSDALSE (SEQ ID NO:41) | TSSSRKK (SEQ ID NO:42) |
| 6592 | QSAVLTE (SEQ ID NO:136) | QSQHLTR (SEQ ID NO:137) | RSDSLSA (SEQ ID NO:63) | DRSSRTK (SEQ ID NO:64) | RSDSLSV (SEQ ID NO:138) | RNQDRKN (SEQ ID NO:139) |
| 6595 | TSHALTQ (SEQ ID NO:140) | DSAHLSR (SEQ ID NO:141) | RSDALSE (SEQ ID NO:41) | RSSDRTK (SEQ ID NO:79) | RSDTLST (SEQ ID NO:80) | QKATRTT (SEQ ID NO:81) |
| 6596 | TSHALTQ (SEQ ID NO:140) | DSAHLSR (SEQ ID NO:141) | RSDHLSQ (SEQ ID NO:33) | TSAHRIK (SEQ ID NO:142) | RSDHLSR (SEQ ID NO:25) | QKDSRKN (SEQ ID NO:143) |
| 6609 | RSDNLSR (SEQ ID NO:93) | DNNARIN (SEQ ID NO:98) | RSDALSQ (SEQ ID NO:144) | RNDNRIT (SEQ ID NO:58) | RSDHLTK (SEQ ID NO:145) | NSDHLSR (SEQ ID NO:146) |
| 6610 | RSDTLSV (SEQ ID NO:147) | DNSTRIK (SEQ ID NO:148) | RSDNLSQ (SEQ ID NO:35) | ASNDRKK (SEQ ID NO:149) | RSDHLSE (SEQ ID NO:54) | RNDNRKT (SEQ ID NO:72) |
| 6612 | RSDALSQ (SEQ ID NO:144) | RNDNRIT (SEQ ID NO:58) | RSDHLTK (SEQ ID NO:145) | NSDHLSR (SEQ ID NO:146) | RSDHLSE (SEQ ID NO:54) | QNANRIT (SEQ ID NO:150) |
| 6613 | RSDNLSR (SEQ ID NO:93) | RSDARTN (SEQ ID NO:94) | RSDNLST (SEQ ID NO:37) | RSDHRKT (SEQ ID NO:151) | RSDNLSA (SEQ ID NO:90) | RSDHRIT (SEQ ID NO:152) |
| 6615 | ASAHLTE (SEQ ID NO:153) | RSDALSR (SEQ ID NO:154) | RSDNLST (SEQ ID NO:37) | RSDHRKT (SEQ ID NO:151) | RSDNLSA (SEQ ID NO:90) | RSDHRIT (SEQ ID NO:152) |
| 6616 | RSDHLSE (SEQ ID NO:54) | TSSSRKN (SEQ ID NO:73) | RSDTLSE (SEQ ID NO:155) | NNRDRTK (SEQ ID NO:156) | RSDHLSQ (SEQ ID NO:33) | QSATRTK (SEQ ID NO:39) |
| 6617 | SNEALIE (SEQ ID NO:157) | ThSSLSR (SEQ ID NO:89) | RSDHLSE (SEQ ID NO:54) | ThSSRKN (SEQ ID NO:73) | RSDTLSV (SEQ ID NO:147) | RNSDRTK (SEQ ID NO:158) |
| 6618 | RSDHLSN (SEQ ID NO:26) | RSDHRTN (SEQ ID NO:27) | RSDALSQ (SEQ ID NO:144) | RNDNRIT (SEQ ID NO:58) | RSDHLTK (SEQ ID NO:145) | NSDHLSR (SEQ ID NO:146) |
| 6619 | RSDALSE (SEQ ID NO:41) | TSSSRKK (SEQ ID NO:42) | RSDALSE (SEQ ID NO:41) | TSSSRKK (SEQ ID NO:42) | RSDNLSV (SEQ ID NO:49) | ANHHRIN (SEQ ID NO:135) |
| 6620 | RSDHLSN (SEQ ID NO:26) | RSDHRTN (SEQ ID NO:27) | RSDALSQ (SEQ ID NO:144) | RNDNRIT (SEQ ID NO:58) | RSDHLSE (SEQ ID NO:54) | RNDNRKR (SEQ ID NO:87) |
| 6621 | RSDALSE (SEQ ID NO:41) | RSSDRTK (SEQ ID NO:79) | RSDTLST (SEQ ID NO:80) | QKATRTT (SEQ ID NO:81) | HSADLTQ (SEQ ID NO:82) | QSSDLSR (SEQ ID NO:83) |
| 6622 | RSDALSE (SEQ ID NO:41) | RSSDRTK (SEQ ID NO:79) | RSDTLST (SEQ ID NO:80) | QKATRTT (SEQ ID NO:81) | RSDTLST (SEQ ID NO:80) | HSDTRKK (SEQ ID NO:84) |
| 6623 | RSDNLSN (SEQ ID NO:61) | TNSNRIK (SEQ ID NO:62) | RSDHLSE (SEQ ID NO:54) | AKHHRKT (SEQ ID NO:227) | RSDALSV (SEQ ID NO:45) | DSSHRTR (SEQ ID NO:159) |
| 6626 | TSHALTQ (SEQ ID NO:140) | DSAHLSR (SEQ ID NO:141) | RSDHLSQ (SEQ ID NO:33) | TSAHRIK (SEQ ID NO:142) | RSDNLSA (SEQ ID NO:90) | RSDHRIT (SEQ ID NO:152) |
| 6627 | RSDTLSV (SEQ ID NO:147) | QNANRTT (SEQ ID NO:160) | TSHALTQ (SEQ ID NO:140) | DSAHLSR (SEQ ID NO:141) | RSDALSE (SEQ ID NO:41) | RSSDRTK (SEQ ID NO:79) |
| 6669 | RSDHLSE (5EQ ID NO:54) | AKHHRKT (SEQ ID NO:227) | RSDALSE (SEQ ID NO:41) | TSSSRKK (SEQ ID NO:42) | RSDALSE (SEQ ID NO:41) | TSSSRKK (SEQ ID NO:42) |
| 7231 | RSDSLSN (SEQ ID NO:161) | TSNNRTT (SEQ ID NO:162) | TSNNRTT (SEQ ID NO:162) | RSDHLSQ (SEQ ID NO:33) | ASSTRIT (SEQ ID NO:163) | RSDVLSA (SEQ ID NO:164) |
| 7232 | RSDSLSV (SEQ ID NO:138) | QNQHRIN (SEQ ID NO:165) | RSDNLAR (SEQ ID NO:166) | TSGHLSR (SEQ ID NO:167) | RSDHLSA (SEQ ID NO:68) | ANSNRIK (SEQ ID NO:168) |
| 7233 | RSHDLIE (SEQ ID NO:169) | TSSSLSR (SEQ ID NO:89) | RSDHLSQ (SEQ ID NO:33) | QSANRTT (SEQ ID NO:170) | RSDHLSR (SEQ ID NO:25) | QSGDLTR (SEQ ID NO:171) |
| 7234 | RSDSLSK (SEQ ID NO:172) | QSANRTT (SEQ ID NO:170) | RSDNLSR (SEQ ID NO:93) | DNNARIN (SEQ ID NO:98) | RSDHLSE (SEQ ID NO:54) | RSADRTK (SEQ ID NO:173) |

TABLE 7-continued

| ZFP | F1 | F2 | F3 | F4 | F5 | F6 |
|---|---|---|---|---|---|---|
| 7235 | RSDSLSN (SEQ ID NO:161) | TRASRIT (SEQ ID NO:174) | RSDNLSR (SEQ ID NO:93) | TNQNRIT (SEQ ID NO:175) | QSGNLAR (SEQ ID NO:176) | QSGNLAR (SEQ ID NO:176) |
| 7236 | RSDSLSN (SEQ ID NO:161) | TRASRIT (SEQ ID NO:174) | RSDNLSR (SEQ ID NO:93) | TNQNRIT (SEQ ID NO:175) | RSDNLSA (SEQ ID NO:90) | RKDTRIT (SEQ ID NO:177) |
| 7237 | RSDNLAR (SEQ ID NO:166) | RSDALAR (SEQ ID NO:178) | RSDALSE (SEQ ID NO:41) | RSSDRTK (SEQ ID NO:79) | RSDHLSR (SEQ ID NO:25) | RNQDRTN (SEQ ID NO:179) |
| 7238 | QSGHLQR (SEQ ID NO:180) | QSGNLAR (SEQ ID NO:176) | QSGDLTR (SEQ ID NO:171) | QSGHLSR (SEQ ID NO:181) | RSDHLSE (SEQ ID NO:54) | QSATRKK (SEQ ID NO:182) |
| 7239 | RSDHLSQ (SEQ ID NO:33) | RNADRKT (SEQ ID NO:183) | RSDHLSN (SEQ ID NO:26) | DNRDRIK (SEQ ID NO:184) | DSAALTA (SEQ ID NO:185) | DSAHLSR (SEQ ID NO:141) |
| 7240 | RSDTLSA (SEQ ID NO:186) | QNANRKT (SEQ ID NO:187) | AKSELNT (SEQ ID NO:188) | TSSSLSR (SEQ ID NO:89) | RSDHLSQ (SEQ ID NO:33) | TSANRTT (SEQ ID NO:189) |
| 7241 | RSDALST (SEQ ID NO:190) | ASSNRIK (SEQ ID NO:191) | RSDVLSQ (SEQ ID NO:192) | TSSNRKT (SEQ ID NO:193) | RSDNLST (SEQ ID NO:37) | DNSNRIN (SEQ ID NO:194) |
| 7276 | RSDHLSE (SEQ ID NO:54) | QSASRKN (SEQ ID NO:195) | QSGDLTR (SEQ ID NO:171) | QSSDLRR (SEQ ID NO:196) | RSDNLSA (SEQ ID NO:90) | RKDTRIT (SEQ ID NO:177) |
| 7277 | DRSALSR (SEQ ID NO:197) | RSDNLTR (SEQ ID NO:198) | RSDSLST (SEQ ID NO:199) | DSSNRIT (SEQ ID NO:200) | RSDTLSE (SEQ ID NO:155) | QNAHRKT (SEQ ID NO:201) |
| 7278 | RSDSLSA (SEQ ID NO:63) | QNANRKT (SEQ ID NO:187) | DRSALSR (SEQ ID NO:197) | RSDNLTR (SEQ ID NO:198) | RSDSLSA (SEQ ID NO:63) | DRSNRKT (SEQ ID NO:202) |
| 7279 | QSGALAR (SEQ ID NO:203) | RSDALAR (SEQ ID NO:178) | RSDALSR (SEQ ID NO:154) | RSDALAR (SEQ ID NO:178) | RSDVLSE (SEQ ID NO:74) | TKSNRTT (SEQ ID NO:204) |
| 7280 | DRSNLSR (SEQ ID NO:205) | RSDNLTR (SEQ ID NO:198) | RSDTLSV (SEQ ID NO:147) | DNSTRIK (SEQ ID NO:148) | RSDHLSN (SEQ ID NO:26) | DNRDRIK (SEQ ID NO:184) |
| 7281 | RSDSLSV (SEQ ID NO:138) | QNQHRIN (SEQ ID NO:165) | RSDHLSE (SEQ ID NO:54) | TSSSRKN (SEQ ID NO:73) | RSDNLAR (SEQ ID NO:166) | QSGDLTR (SEQ ID NO:171) |

The amino acid residues shown in Tables 2, 3, 4, 5 and 7 correspond to residues −1 through +6 with respect to the start of the alpha-helical portion of a zinc finger and are denoted the "recognition regions" because one or more of these residues participate in sequence specificity of nucleic acid binding. Accordingly, proteins comprising the same recognition regions in any polypeptide backbone sequence are considered equivalents to the protein identified in Tables 2, 3, 4, 5, and 7, since they have the same DNA-binding specificity.

Thus, in certain embodiments, the recognition regions disclosed in Tables 2, 3, 4, 5 and 7 can be present in any zinc finger backbone (see, e.g., U.S. Pat. Nos. 6,453,242 and 6,534,261) and the resulting proteins can be used to regulate transcription, e.g., in the treatment of neuropathic pain.

Within the recognition region, residues −1, +3 and +6 are primarily responsible for protein-nucleotide contacts. The residue at position +2 is also sometimes involved in binding specificity. Accordingly, non-limiting examples of additional equivalents include zinc fingers containing residues at positions −1, +3 and +6 (and optionally +2) that are identical to those of any of the zinc fingers disclosed herein.

Correspondences between amino acids at the −1, +3 and +6 (and optionally +2) contact residues of the recognition region of a zinc finger, and nucleotides in a target site, have been described. See, for example, U.S. Pat. Nos. 6,007,988; 6,013,453; 6,746,838; and 6,866,997; as well as PCT Publications WO 96/06166; WO 98/53058; WO 98/53059 and WO 98/53060. Accordingly, also to be considered equivalents are zinc finger proteins having the same binding specificity, according to the aforementioned design rules, as the proteins disclosed herein.

IV. Characteristics of ZFPS

Zinc finger proteins are formed from zinc finger components. For example, zinc finger proteins can have one to thirty-seven fingers, commonly having 2, 3, 4, 5 or 6 fingers. A zinc finger protein recognizes and binds to a target site (sometimes referred to as a target segment) that represents a relatively small subsequence within a target gene. Each component finger of a zinc finger protein can bind to a subsite within the target site. The subsite includes a triplet of three contiguous bases all on the same strand (sometimes referred to as the target strand). The subsite may or may not also include a fourth base on the opposite strand that is the complement of the base immediately 3' of the three contiguous bases on the target strand. In many zinc finger proteins, a zinc finger binds to its triplet subsite substantially independently of other fingers in the same zinc finger protein. Accordingly, the binding specificity of zinc finger protein containing multiple fingers is usually approximately the aggregate of the specificities of its component fingers. For example, if a zinc finger protein is formed from first, second and third fingers that individually bind to triplets XXX, YYY, and ZZZ, the binding specificity of the zinc finger protein is 3'XXX YYY ZZZ5'.

The relative order of fingers in a zinc finger protein from N-terminal to C-terminal determines the relative order of triplets in the 3' to 5' direction in the target. For example, if a zinc finger protein comprises from N-terminal to C-terminal first, second and third fingers that individually bind, respectively, to triplets 5'GAC3', 5'GTA3' and 5'GGC3' then the zinc finger protein binds to the target segment 3'CAGATGCGG5'. If the zinc finger protein comprises the fingers in another order, for example, second finger, first finger, third finger, then the zinc finger protein binds to a target segment comprising a different permutation of triplets, in this example, 3'ATGCAGCGG5'. See Berg & Shi, Science 271, 1081-1086 (1996). The assessment of binding properties of a zinc finger protein as the aggregate of its component fingers may, in some cases, be influenced by context-dependent interactions of multiple fingers binding in the same protein.

Two or more zinc finger proteins can be linked to have a target specificity that is the aggregate of that of the component zinc finger proteins (see e.g., Kim & Pabo, Proc. Natl. Acad. Sci. U.S.A. 95, 2812-2817 (1998)). For example, a first zinc finger protein having first, second and third component fingers that respectively bind to XXX, YYY and ZZZ can be linked to a second zinc finger protein having first, second and third component fingers with binding specificities, AAA, BBB and CCC. The binding specificity of the combined first and second proteins is thus 3'XXXYYYZZZ_AAABBBCCC5', where the underline indicates a short intervening region (typically 0-5 bases of any type). In this situation, the target site can be viewed as comprising two target segments separated by an intervening segment.

Linkage can be accomplished using any of the following peptide linkers: T G E K P: (SEQ ID NO:206) (Liu et al., 1997, supra.); (G4S)n (SEQ ID NO:207) (Kim et al., Proc. Natl. Acad. Sci. U.S.A. 93:1156-1160 (1996.); GGRRGGGS (SEQ ID NO:208); LRQRDGERP(SEQ ID NO:209); LRQKDGGGSERP (SEQ ID NO:210) LRQKD $(G_3S)_2$ERP (SEQ ID NO:211).

Alternatively, flexible linkers can be rationally designed using computer programs capable of modeling both DNA-binding sites and the peptides themselves or by phage display methods. In a further variation, noncovalent linkage can be achieved by fusing two zinc finger proteins with domains promoting heterodimer formation of the two zinc finger proteins. For example, one zinc finger protein can be fused with fos and the other with jun (see Barbas et al., WO 95/119431).

Linkage of two zinc finger proteins is advantageous for conferring a unique binding specificity within a mammalian genome. A typical mammalian diploid genome consists of $3\times10^9$ bp. Assuming that the four nucleotides A, C, G, and T are randomly distributed, a given 9 bp sequence is present approximately 23,000 times. Thus a ZFP recognizing a 9 bp target with absolute specificity would have the potential to bind to.about.23,000 sites within the genome. An 18 bp sequence is present about once in a random DNA sequence whose complexity is ten times that of a mammalian genome.

A component finger of zinc finger protein typically contains about 30 amino acids and in one embodiment, has the following motif (N-C):

Cys-$(X)_{2-4}$-Cys-X.X.X.X.X.X.X.X.X.X.X.X-His-(X)3-5-His (SEQ ID NO:1)

The two invariant histidine residues and two invariant cysteine residues in a single beta turn are coordinated through zinc atom (see, e.g., Berg & Shi, Science 271, 1081-1085 (1996)). The above motif shows a numbering convention that is standard in the field for the region of a zinc finger conferring binding specificity. The amino acid on the left (N-terminal side) of the first invariant His residue is assigned the number +6, and other amino acids further to the left are assigned successively decreasing numbers. The alpha helix begins at residue 1 and extends to the residue following the second conserved histidine. The entire helix is therefore of variable length, between 11 and 13 residues.

V. Design of ZFPS

The ZFPs provided herein are engineered to recognize a selected target site in a gene involved in neuropathic pain (e.g., VR1, TRKA, or NAV1.8). Non-limiting examples of ZFPs suitable for modulating expression of these and other genes are described herein.

The process of designing or selecting a ZFP typically starts with a natural ZFP as a source of framework residues. The process of design or selection serves to define nonconserved positions (i.e., positions −1 to +6) so as to confer a desired binding specificity. One suitable ZFP is the DNA binding domain of the mouse transcription factor Zif268. The DNA binding domain of this protein has the amino acid sequence:

```
                                    (SEQ ID NO:212)
YACPVESCDRRFSRSDELTRHIRIHTGQKP (F1)

                                    (SEQ ID NO:213)
FQCRICMRNFSRSDHLTTHIRTHTGEKP (F2)

                                     SEQ ID NO:214)
FACDICGRKFARSDERKRHTKIHLRQK (F3)

and binds to a target 5' GCG TGG GCG 3'.
```

Another suitable natural zinc finger protein as a source of framework residues is Sp-1. The Sp-1 sequence used for construction of zinc finger proteins corresponds to amino acids 531 to 624 in the Sp-1 transcription factor. This sequence is 94 amino acids in length. See, e.g., U.S. Patent Application No. 20030021776 for the sequence of Sp1 and an alternate form of Sp-1, referred to as an Sp-1 consensus sequence.

Sp-1 binds to a target site 5'GGG GCG GGG3'.

There are a number of substitution rules that assist rational design of some zinc finger proteins. For example, ZFP DNA-binding domains can be designed and/or selected to recognize a particular target site as described in U.S. Pat. Nos. 6,453,242; 6,534,261; 6,746,838; 6,785,613; 6,794,136; and 6,866,997; U.S. Patent Application Publication No. 2003/0104526; as well as U.S. Pat. Nos. 5,789,538; 6,007,408; 6,013,453; 6,140,081; and 6,140,466; and PCT publications WO 95/19431, WO 98/53058; WO 98/53059; WO 98/53060; WO 98/54311, WO 00/23464 and WO 00/27878.

In one embodiment, a target site for a zinc finger DNA-binding domain is identified according to site selection rules disclosed in co-owned U.S. Pat. No. No. 6,453,242. In certain embodiments, a ZFP is selected as described in co-owned WO 02/077227; See also WO 96/06166; Desjarlais & Berg, PNAS 90, 2256-2260 (1993); Choo & Klug, PNAS 91, 11163-11167 (1994); Desjarlais & Berg, PNAS 89, 7345-7349 (1992); Jamieson et al., Biochemistry 33:5689-5695 (1994); and Choo et al., WO 98/53057, WO 98/53058; WO 98/53059; WO 98/53060.

Many of these rules are supported by site-directed mutagenesis of the three-finger domain of the ubiquitous transcription factor, Sp-1 (Desjarlais and Berg, 1992; 1993). One of these rules is that a 5' G in a DNA triplet can be bound by a zinc finger incorporating arginine at position 6 of the recognition helix. Another substitution rule is that a G in the middle of a subsite can be recognized by including a histidine residue at position 3 of a zinc finger. A further substitution rule is that asparagine can be incorporated to recognize A in the middle of a triplet, aspartic acid, glutamic acid, serine or threonine can be incorporated to recognize C in the middle of a triplet, and amino acids with small side chains such as alanine can be incorporated to recognize T in the middle of a triplet. A further substitution rule is that the 3' base of a triplet subsite can be recognized by incorporating the following amino acids at position −1 of the recognition helix: arginine to recognize G, glutamine to recognize A, glutamic acid (or aspartic acid) to recognize C, and threonine to recognize T. Although these substitution rules are useful in designing zinc finger proteins they do not take into account all possible target sites. Furthermore, the assumption underlying the rules, namely that a particular amino acid in a zinc finger is responsible for binding to a particular base in a subsite is only approximate. Context-dependent interactions between proximate amino acids in a finger or binding of multiple amino acids to a single base or vice versa can cause variation of the binding specificities predicted by the existing substitution rules. Accordingly, in certain embodiments, a ZFP DNA-binding domain of predetermined specificity is obtained according to the methods described in co-owned WO 02/077227.

Any suitable method known in the art can be used to design and construct nucleic acids encoding ZFPs, e.g., phage display, random mutagenesis, combinatorial libraries, computer/rational design, affinity selection, PCR, cloning from cDNA or genomic libraries, synthetic construction and the like. (see, e.g., U.S. Pat. No. 5,786,538; Wu et al., PNAS 92:344-348 (1995); Jamieson et al., Biochemistry 33:5689-5695 (1994); Rebar & Pabo, Science 263:671-673 (1994); Choo & Klug, PNAS 91:11163-11167 (1994); Choo & Klug, PNAS 91: 11168-11172 (1994); Desjarlais & Berg, PNAS 90:2256-2260 (1993); Desjarlais & Berg, PNAS 89:7345-7349 (1992); Pomerantz et al., Science 267:93-96 (1995); Pomerantz et al., PNAS 92:9752-9756 (1995); and Liu et al., PNAS 94:5525-5530 (1997); Griesman & Pabo, Science 275:657-661 (1997); Desjarlais & Berg, PNAS 91:11-99-11103 (1994)).

In certain preferred embodiments, the binding specificity of a DNA-binding domain (e.g., a ZFP DNA-binding domain) is determined by identifying accessible regions in the sequence in question (e.g., in cellular chromatin). Accessible regions can be determined as described in co-owned WO 01/83732. See, also, U.S. Patent Application No. 20030021776A1. A DNA-binding domain is then designed and/or selected as described herein to bind to a target site within the accessible region.

VI. Production of Zinc Finger Proteins

A. Synthesis and Cloning

ZFP polypeptides and nucleic acids encoding the same can be made using routine techniques in the field of recombinant genetics. Basic texts disclosing general methods include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)). In addition, nucleic acids less than about 100 bases can be custom ordered from any of a variety of commercial sources, such as The Midland Certified Reagent Company (mcrc@oligos.com), The Great American Gene Company (http://www.genco.com), ExpressGen Inc. (www.expressgen.com), Operon Technologies Inc. (Alameda, Calif.). Similarly, peptides can be custom ordered from any of a variety of sources, such as PeptidoGenic (pkim@ccnet.com), HTI Bio-products, Inc. (http://www.hti-bio.com), BMA Biomedicals Ltd (U.K.), Bio.Synthesis, Inc.

Oligonucleotides can be chemically synthesized according to the solid phase phosphoramidite triester method first described by Beaucage & Caruthers, Tetrahedron Letts. 22:1859-1862 (1981), using an automated synthesizer, as described in Van Devanter et al., Nucleic Acids Res. 12:6159-6168 (1984). Purification of oligonucleotides is by either denaturing polyacrylamide gel electrophoresis or by reverse phase HPLC. The sequence of the cloned genes and synthetic oligonucleotides can be verified after cloning using, e.g., the chain termination method for sequencing double-stranded templates of Wallace et al., Gene 16:21-26 (1981).

Two alternative methods are typically used to create the coding sequences required to express newly designed DNA-binding peptides. One protocol is a PCR-based assembly procedure that utilizes six overlapping oligonucleotides. Three oligonucleotides correspond to “universal” sequences that encode portions of the DNA-binding domain between the recognition helices. These oligonucleotides typically remain constant for all zinc finger constructs. The other three “specific” oligonucleotides are designed to encode the recognition helices. These oligonucleotides contain substitutions primarily at positions −1, 2, 3 and 6 on the recognition helices making them specific for each of the different DNA-binding domains.

The PCR synthesis is carried out in two steps. First, a double stranded DNA template is created by combining the six oligonucleotides (three universal, three specific) in a four cycle PCR reaction with a low temperature annealing step, thereby annealing the oligonucleotides to form a DNA “scaffold.” The gaps in the scaffold are filled in by high-fidelity thermostable polymerase, the combination of Taq and Pfu polymerases also suffices. In the second phase of construction, the zinc finger template is amplified by external primers designed to incorporate restriction sites at either end for cloning into a shuttle vector or directly into an expression vector.

An alternative method of cloning the newly designed DNA-binding proteins relies on annealing complementary oligonucleotides encoding the specific regions of the desired ZFP. This particular application requires that the oligonucleotides be phosphorylated prior to the final ligation step. This is usually performed before setting up the annealing reactions. In brief, the “universal” oligonucleotides encoding the constant regions of the proteins (oligos 1, 2 and 3 of above) are annealed with their complementary oligonucleotides. Additionally, the “specific” oligonucleotides encoding the finger recognition helices are annealed with their respective complementary oligonucleotides. These complementary oligos are designed to fill in the region that was previously filled in by polymerase in the above-mentioned protocol. Oligonucleotides complementary to oligos 1 and 6 are engineered to leave overhanging sequences specific for the restriction sites used in cloning into the vector of choice in the following step. The second assembly protocol differs from the initial protocol in the following aspects: the “scaffold” encoding the newly designed ZFP is composed entirely of synthetic DNA thereby eliminating the polymerase fill-in step, additionally the fragment to be cloned into the vector does not require amplification. Lastly, the design of leaving sequence-specific overhangs eliminates the need for restriction enzyme digests of the inserting fragment. Alternatively, changes to ZFP recognition helices can be created using conventional site-directed mutagenesis methods.

Both assembly methods require that the resulting fragment encoding the newly designed ZFP be ligated into a vector. Ultimately, the ZFP-encoding sequence is cloned into an expression vector. Expression vectors that are commonly utilized include, but are not limited to, a modified pMAL-c2 bacterial expression vector (New England BioLabs, Beverly, Mass.) or an eukaryotic expression vector, pcDNA (Promega, Madison, Wis.). The final constructs are verified by sequence analysis.

Any suitable method of protein purification known to those of skill in the art can be used to purify ZFPs (see, Ausubel, supra, Sambrook, supra). In addition, any suitable host can be used for expression, e.g., bacterial cells, insect cells, yeast cells, mammalian cells, and the like.

Expression of a zinc finger protein fused to a maltose binding protein (MBP-ZFP) in bacterial strain JM109 allows for straightforward purification through an amylose column (New England BioLabs, Beverly, Mass.). High expression levels of the zinc finger chimeric protein can be obtained by induction with IPTG since the MBP-ZFP fusion in the pMal-c2 expression plasmid is under the control of the tac promoter (New England BioLabs, Beverly, Mass.). Bacteria containing the MBP-ZFP fusion plasmids are inoculated into 2×YT medium containing 10 μM $ZnCl_2$, 0.02% glucose, plus 50 μg/ml ampicillin and shaken at 37° C. At mid-exponential growth IPTG is added to 0.3 mM and the cultures are allowed to shake. After 3 hours the bacteria are harvested by centrifugation, disrupted by sonication or by passage through a pressure cell or through the use of lysozyme, and insoluble material is removed by centrifugation. The MBP-ZFP proteins are captured on an amylose-bound resin, washed extensively with buffer containing 20 mM Tris-HCl (pH 7.5), 200 mM NaCl, 5 mM DTT and 50.mu.M $ZnCl_2$, then eluted with maltose in essentially the same buffer (purification is based on a standard protocol from New England BioLabs. Purified proteins are quantitated and stored for biochemical analysis.

The dissociation constant of a purified protein, e.g., Kd, is typically characterized via electrophoretic mobility shift assays (EMSA) (Buratowski & Chodosh, in Current Protocols in Molecular Biology pp. 12.2.1-12.2.7 (Ausubel ed., 1996)). Affinity is measured by titrating purified protein against a fixed amount of labeled double-stranded oligonucleotide target. The target typically comprises the natural binding site sequence flanked by the 3 bp found in the natural sequence and additional, constant flanking sequences. The natural binding site is typically 9 bp for a three-finger protein and 2.times.9 bp +intervening bases for a six finger ZFP. The annealed oligonucleotide targets possess a 1 base 5' overhang that allows for efficient labeling of the target with T4 phage polynucleotide kinase. For the assay the target is added at a concentration of 1 nM or lower (the actual concentration is kept at least 10-fold lower than the expected dissociation constant), purified ZFPs are added at various concentrations, and the reaction is allowed to equilibrate for at least 45 min. In addition the reaction mixture also contains 10 mM Tris (pH 7.5), 100 mM KCl, 1 mM $MgCl_2$, 0.1 mM $ZnCl_2$, 5 mM DTT, 10% glycerol, 0.02% BSA.

The equilibrated reactions are loaded onto a 10% polyacrylamide gel, which has been pre-run for 45 min in Tris/glycine buffer, then bound and unbound labeled target is resolved by electrophoresis at 150V. Alternatively, 10-20% gradient Tris-HCl gels, containing a 4% polyacrylamide stacking gel, can be used. The dried gels are visualized by autoradiography or phosphorimaging and the apparent Kd is determined by calculating the protein concentration that yields half-maximal binding.

The assays can also include a determination of the active fraction in the protein preparations. Active fraction is determined by stoichiometric gel shifts in which protein is titrated against a high concentration of target DNA. Titrations are done at 100, 50, and 25% of target (usually at micromolar levels).

B. Phage Display

The technique of phage display provides a largely empirical means of generating zinc finger proteins with desired target specificity (see e.g., Rebar, U.S. Pat. No. 5,789,538; Choo et al., WO 96/06166; Barbas et al., WO 95/19431 and WO 98/543111; Jamieson et al., supra). The method can be used in conjunction with, or as an alternative to rational design. The method involves the generation of diverse libraries of mutagenized zinc finger proteins, followed by the isolation of proteins with desired DNA-binding properties using affinity selection methods. To use this method, the experimenter typically proceeds as follows. First, a gene for a zinc finger protein is mutagenized to introduce diversity into regions important for binding specificity and/or affinity. In a typical application, this is accomplished via randomization of a single finger at positions −1, +2, +3, and +6, and sometimes accessory positions such as +1, +5, +8 and +10. Next, the mutagenized gene is cloned into a phage or phagemid vector as a fusion with gene III of a filamentous phage, which encodes the coat protein pIII. The zinc finger gene is inserted between segments of gene III encoding the membrane export signal peptide and the remainder of pill, so that the zinc finger protein is expressed as an amino-terminal fusion with pIII or in the mature, processed protein.

When using phagemid vectors, the mutagenized zinc finger gene may also be fused to a truncated version of gene III encoding, minimally, the C-terminal region required for assembly of pIII into the phage particle. The resultant vector library is transformed into *E. coli* and used to produce filamentous phage that express variant zinc finger proteins on their surface as fusions with the coat protein pIII. If a phagemid vector is used, then this step requires superinfection with helper phage. The phage library is then incubated with a target DNA site, and affinity selection methods are used to isolate phage that bind target with high affinity from bulk phage. Typically, the DNA target is immobilized on a solid support, which is then washed under conditions sufficient to remove all but the tightest binding phage. After washing, any phage remaining on the support are recovered via elution under conditions which disrupt zinc finger—DNA binding. Recovered phage are used to infect fresh *E. coli*, which is then amplified and used to produce a new batch of phage particles. Selection and amplification are then repeated as many times as is necessary to enrich the phage pool for tight binders such that these may be identified using sequencing and/or screening methods. Although the method is illustrated for pIII fusions, analogous principles can be used to screen ZFP variants as pVIII fusions.

In certain embodiments, the sequence bound by a particular zinc finger protein is determined by conducting binding reactions (see, e.g., conditions for determination of Kd, supra) between the protein and a pool of randomized double-stranded oligonucleotide sequences. The binding reaction is analyzed by an electrophoretic mobility shift assay (EMSA), in which protein-DNA complexes undergo retarded migration in a gel and can be separated from unbound nucleic acid. Oligonucleotides that have bound the finger are purified from the gel and amplified, for example, by a polymerase chain reaction. The selection (i.e. binding reaction and EMSA analysis) is then repeated as many times as desired, with the selected oligonucleotide sequences. In this way, the binding specificity of a zinc finger protein having a particular amino acid sequence is determined.

C. Regulatory Domains

Zinc finger proteins are often expressed with an exogenous domain (or functional fragment thereof) as fusion proteins. Common domains for addition to the ZFP include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. A preferred domain for fusing with a ZFP when the ZFP is to be used for repressing expression of a target gene is a KRAB repression domain from the human KOX-1 protein (Thiesen et al., New Biologist 2, 363-374 (1990); Margolin et al., Proc. Natl. Acad. Sci. USA 91, 4509-4513 (1994); Pengue et al., Nucl. Acids Res. 22:2908-2914 (1994); Witzgall et al., Proc. Natl. Acad. Sci. USA 91, 4514-4518 (1994). Preferred domains for achieving activation include the HSV VP16 activation domain (see, e.g., Hagmann et al., J. Virol. 71, 5952-5962 (1997)) nuclear hormone receptors (see, e.g., Torchia et al., Curr. Opin. Cell. Biol. 10:373-383 (1998)); the p65 subunit of nuclear factor kappa B (Bitko & Barik, J. Virol. 72:5610-5618 (1998) and Doyle & Hunt, Neuroreport 8:2937-2942 (1997)); Liu et al., Cancer Gene Ther. 5:3-28 (1998)), or artificial chimeric functional domains such as VP64 (Seifpal et al., EMBO J. 11, 4961-4968 (1992)).

The identification of novel sequences and accessible regions (e.g., DNase I hypersensitive sites) in genes involved in neuropathic pain allows for the design of fusion molecules for the treatment of pain. Thus, in certain embodiments, the compositions and methods disclosed herein involve fusions between a DNA-binding domain specifically targeted to one or more regulatory regions of a target gene involved in neuropathic pain and a functional (e.g., repression or activation) domain (or a polynucleotide encoding such a fusion). In this way, the repression or activation domain is brought into proximity with a sequence in the gene that is bound by the DNA-binding domain. The transcriptional regulatory function of the functional domain is then able to act on the selected regulatory sequences.

In additional embodiments, targeted remodeling of chromatin, as disclosed in co-owned WO 01/83793 can be used to generate one or more sites in cellular chromatin that are accessible to the binding of a DNA binding molecule.

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al. (2000) Proc. Natl. Acad. Sci. USA 97:3930-3935.

In certain embodiments, the target site bound by the zinc finger protein is present in an accessible region of cellular chromatin. Accessible regions can be determined as described, for example, in co-owned International Publication WO 01/83732. If the target site is not present in an accessible region of cellular chromatin, one or more accessible regions can be generated as described in co-owned WO 01/83793. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3). Cordingley et al. (1987) Cell 48:261-270; Pina et al. (1990) Cell 60:719-731; and Cirillo et al. (1998) EMBO J. 17:244-254.

For such applications, the fusion molecule is typically formulated with a pharmaceutically acceptable carrier, as is known to those of skill in the art. See, for example, Remington's Pharmaceutical Sciences, 17th ed., 1985; and co-owned WO 00/42219.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

Exemplary functional domains for fusing with a DNA-binding domain such as, for example, a ZFP, to be used for repressing expression of a gene is a KOX repression domain or a KRAB repression domain from the human KOX-1 protein (see, e.g., Thiesen et al., New Biologist 2, 363-374 (1990); Margolin et al., Proc. Natl. Acad. Sci. USA 91, 4509-4513 (1994); Pengue et al., Nucl. Acids Res. 22:2908-2914 (1994); Witzgall et al., Proc. Natl. Acad. Sci. USA 91, 4514-4518 (1994). Another suitable repression domain is methyl binding domain protein 2B (MBD-2B) (see, also Hendrich et al. (1999) Mamm Genome 10:906-912 for description of MBD proteins). Another useful repression domain is that associated with the v-ErbA protein. See, for example, Damm, et al. (1989) Nature 339:593-597; Evans (1989) Int. J. Cancer Suppl. 4:26-28; Pain et al. (1990) New Biol. 2:284-294; Sap et al. (1989) Nature 340:242-244; Zenke et al. (1988) Cell 52:107-119; and Zenke et al. (1990) Cell 61:1035-1049.

Suitable domains for achieving activation include the HSV VP16 activation domain (see, e.g., Hagmann et al., J. Virol. 71, 5952-5962 (1997)) nuclear hormone receptors (see, e.g., Torchia et al., Curr. Opin. Cell. Biol. 10:373-383 (1998)); the p65 subunit of nuclear factor kappa B (Bitko & Barik, J. Virol. 72:5610-5618 (1998) and Doyle & Hunt, Neuroreport 8:2937-2942 (1997)); Liu et al., Cancer Gene Ther. 5:3-28 (1998)), or artificial chimeric functional domains such as VP64 (Seifpal et al., EMBO J. 11, 4961-

4968 (1992)). Additional exemplary activation domains include, but are not limited to, VP16, VP64, p300, CBP, PCAF, SRC1 PvALF, AtHD2A and ERF-2. See, for example, Robyr et al. (2000) Mol. Endocrinol. 14:329-347; Collingwood et al. (1999) J. Mol. Endocrinol. 23:255-275; Leo et al. (2000) Gene 245:1-11; Manteuffel-Cymborowska (1999) Acta Biochim. Pol. 46:77-89; McKenna et al. (1999) J. Steroid Biochem. Mol. Biol. 69:3-12; Malik et al. (2000) Trends Biochem. Sci. 25:277-283; and Lemon et al. (1999) Curr. Opin. Genet. Dev. 9:499-504. Additional exemplary activation domains include, but are not limited to, OsGAI, HALF-1, C1, AP1, ARF-5,-6,-7, and -8, CPRF1, CPRF4, MYC-RP/GP, and TRABI. See, for example, Ogawa et al. (2000) Gene 245:21-29; Okanami et al. (1996) Genes Cells 1:87-99; Goff et al. (1991) Genes Dev. 5:298-309; Cho et al. (1999) Plant Mol. Biol. 40:419-429; Ulmason et al. (1999) Proc. Natl. Acad. Sci. USA 96:5844-5849; Sprenger-Haussels et al. (2000) Plant J. 22:1-8; Gong et al. (1999) Plant Mol. Biol. 41:33-44; and Hobo et al. (1999) Proc. Natl. Acad. Sci. USA 96:15,348-15,353.

Additional exemplary repression domains include, but are not limited to, KRAB (also referred to as "KOX"), SID, MBD2, MBD3, members of the DNMT family (e.g., DNMT1, DNMT3A, DNMT3B), Rb, and MeCP2. See, for example, Bird et al. (1999) Cell 99:451-454; Tyler et al. (1999) Cell 99:443-446; Knoepfler et al. (1999) Cell 99:447-450; and Robertson et al. (2000) Nature Genet. 25:338-342. Additional exemplary repression domains include, but are not limited to, ROM2 and AtHD2A. See, for example, Chem et al. (1996) Plant Cell 8:305-321; and Wu et al. (2000) Plant J. 22:19-27.

Additional exemplary functional domains are disclosed, for example, in co-owned U.S. Pat. No. 6,534,261 and US Patent Application Publication No. 2002/0160940.

D. Expression Vectors

The nucleic acid encoding the ZFP of choice is typically cloned into intermediate vectors for transformation into prokaryotic or eukaryotic cells for replication and/or expression, e.g., for determination of Kd. Intermediate vectors are typically prokaryote vectors, e.g., plasmids, or shuttle vectors, or insect vectors, for storage or manipulation of the nucleic acid encoding ZFP or production of protein. The nucleic acid encoding a ZFP is also typically cloned into an expression vector, for administration to a plant cell, animal cell, preferably a mammalian cell or a human cell, fungal cell, bacterial cell, or protozoal cell.

To obtain expression of a cloned gene or nucleic acid, a ZFP is typically subcloned into an expression vector that contains a promoter to direct transcription. Suitable bacterial and eukaryotic promoters are well known in the art and described, e.g., in Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994). Bacterial expression systems for expressing the ZFP are available in, e.g., *E. coli, Bacillus* sp., and *Salmonella* (Palva et al., Gene 22:229-235 (1983)). Kits for such expression systems are commercially available. Eukaryotic expression systems for mammalian cells, yeast, and insect cells are well known in the art and are also commercially available.

The promoter used to direct expression of a ZFP nucleic acid depends on the particular application. For example, a strong constitutive promoter is typically used for expression and purification of ZFP. In contrast, when a ZFP is administered in vivo for gene regulation, either a constitutive or an inducible promoter is used, depending on the particular use of the ZFP. In addition, a preferred promoter for administration of a ZFP can be a weak promoter, such as HSV TK or a promoter having similar activity. The promoter typically can also include elements that are responsive to transactivation, e.g., hypoxia response elements, Gal4 response elements, lac repressor response element, and small molecule control systems such as tet-regulated systems and the RU-486 system (see, e.g., Gossen & Bujard, PNAS 89:5547 (1992); Oligino et al., Gene Ther. 5:491-496 (1998); Wang et al., Gene Ther. 4:432-441 (1997); Neering et al., Blood 88:1147-1155 (1996); and Rendahl et al., Nat. Biotechnol. 16:757-761 (1998)).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the ZFP, and signals required, e.g., for efficient polyadenylation of the transcript, transcriptional termination, ribosome binding sites, or translation termination. Additional elements of the cassette may include, e.g., enhancers, and exogenous spliced intronic signals.

The particular expression vector used to transport the genetic information into the cell is selected with regard to the intended use of the ZFP. Standard bacterial expression vectors include plasmids such as pBR322 based plasmids, pSKF, pET23D, and commercially available fusion expression systems such as GST and LacZ. A preferred fusion protein is the maltose binding protein, "MBP." Such fusion proteins are used for purification of the ZFP. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with a ZFP encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

VII. Assays

Once a ZFP has been designed and prepared according to the procedures just set forth, an initial assessment of the activity of the designed ZFP is undertaken. ZFP proteins showing the ability to modulate the expression of a gene of interest can then be further assayed for more specific activities depending upon the particular application for which the ZFPs have been designed. Thus, for example, the ZFPs provided herein can be initially assayed for their ability to modulate expression of genes involved in neuropathic pain. More specific assays of the ability of the ZFP to modulate expression of the target genes involved in neuropathic pain to treat this pain are then typically undertaken. A description of these more specific assays are set forth infra in section IX.

The activity of a particular ZFP can be assessed using a variety of in vitro and in vivo assays, by measuring, e.g., protein or mRNA levels, product levels, enzyme activity, tumor growth; transcriptional activation or repression of a reporter gene; second messenger levels (e.g., cGMP, cAMP, IP3, DAG, Ca2+); cytokine and hormone production levels; and neovascularization, using, e.g., immunoassays (e.g., ELISA and immunohistochemical assays with antibodies), hybridization assays (e.g., RNase protection, Northerns, in situ hybridization, oligonucleotide array studies), colorimetric assays, amplification assays, enzyme activity assays, tumor growth assays, phenotypic assays, and the like.

ZFPs are typically first tested for activity in vitro using cultured cells, e.g., 293 cells, CHO cells, VERO cells, BHK cells, HeLa cells, COS cells, and the like. Preferably, human cells are used. The ZFP is often first tested using a transient expression system with a reporter gene, and then regulation of the target endogenous gene is tested in cells and in animals, both in vivo and ex vivo. The ZFP can be recombinantly expressed in a cell, recombinantly expressed in cells transplanted into an animal, or recombinantly expressed in a transgenic animal, as well as administered as a protein to an animal or cell using delivery vehicles described below. The cells can be immobilized, be in solution, be injected into an animal, or be naturally occurring in a transgenic or non-transgenic animal.

Modulation of gene expression is tested using one of the in vitro or in vivo assays described herein. Samples or assays are treated with a ZFP and compared to untreated control samples, to examine the extent of modulation. As described above, for regulation of endogenous gene expression, the ZFP typically has a Kd of 200 nM or less, more preferably 100 nM or less, more preferably 50 nM, most preferably 25 nM or less.

The effects of the ZFPs can be measured by examining any of the parameters described above. Any suitable gene expression, phenotypic, or physiological change can be used to assess the influence of a ZFP. When the functional consequences are determined using intact cells or animals, one can also measure a variety of effects such as neurotrophism, transcriptional changes to both known and uncharacterized genetic markers (e.g., Northern blots or oligonucleotide array studies), changes in cell metabolism such as cell growth or pH changes, and changes in intracellular second messengers such as cAMP or cGMP.

Preferred assays for ZFP regulation of endogenous gene expression can be performed in vitro. In one preferred in vitro assay format, ZFP regulation of endogenous gene expression in cultured cells is measured by examining protein production using an ELISA assay. The test sample is compared to control cells treated with a vector lacking ZFP-encoding sequences or a vector encoding an unrelated ZFP that is targeted to another gene.

In another embodiment, ZFP regulation of endogenous gene expression is determined in vitro by measuring the level of gene mRNA expression (e.g., expression level of VR1, TrkA and/or NaV1.8 gene). The level of gene expression is measured using amplification, e.g., using PCR, LCR, or hybridization assays, e.g., Northern hybridization, dot blotting and RNase protection. The use of quantitative RT-PCR techniques (i.e., the so-called TaqMan® assays) can also be utilized to quantitate the level of transcript. The level of protein or mRNA is detected using directly or indirectly labeled detection agents, e.g., fluorescently or radioactively labeled nucleic acids, radioactively or enzymatically labeled antibodies, and the like, as described herein. Such methods are also described in U.S. Pat. No. 5,210,015 to Gelfand, U.S. Pat. No. 5,538,848 to Livak, et al., and U.S. Pat. No. 5,863,736 to Haaland, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995), each of which is incorporated by reference in its entirety.

Alternatively, a reporter gene system can be devised using a gene promoter from the selected target gene (e.g., VR1, TRKA, and/or NAV1.8) operably linked to a reporter gene such as luciferase, green fluorescent protein, CAT, GAPDH, β-gal, etc. The reporter construct is typically co-transfected into a cultured cell. After treatment with the ZFP of choice, the amount of reporter gene transcription, translation, or activity is measured according to standard techniques known to those of skill in the art.

Another example of a preferred assay format useful for monitoring ZFP regulation of endogenous gene expression is performed in vivo. This assay is particularly useful for examining genes involved in chronic pain. In this assay, the ZFP of choice is administered (e.g., intramuscular or intravenous injection) into an animal exhibiting aberrant nerve excitability. After a suitable length of time, preferably 4-8 weeks, nerve function and/or gene expression are compared to control animals that also have aberrant nerve excitability but did not receive a ZFP. Nerve excitability that is significantly different as between control and test animals (using, e.g., Student's T test) are determined to have been affected by the ZFP.

VIII. Pharmaceutical Compositions

The ZFPs provided herein, and more typically the nucleic acids encoding them, can optionally be formulated with a pharmaceutically acceptable carrier as a pharmaceutical composition.

A. Nucleic Acid Based Compositions

Conventional viral and non-viral based gene transfer methods can be used to introduce nucleic acids encoding the present ZFPs in mammalian cells or target tissues. Such methods can be used to administer nucleic acids encoding ZFPs to cells in vitro. In some instances, the nucleic acids encoding ZFPs are administered for in vivo or ex vivo gene therapy uses. Non-viral vector delivery systems include DNA plasmids, naked nucleic acid, and nucleic acid complexed with a delivery vehicle such as poloxamers or liposomes. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11: 167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1:13-26 (1994).

Methods of non-viral delivery of nucleic acids encoding the ZFPs provided herein include lipofection, microinjection, biolistics, virosomes, liposomes, immunoliposomes, polycation or lipid:nucleic acid conjugates, naked DNA, artificial virions, electroporation and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered ZFP take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs can include retroviral, lentivirus, adenoviral, adeno-associated and herpes simplex virus (HSV) vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long-term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system can therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommerfelt et al., Virol. 176:58-59 (1990); Wilson et al., J. Virol. 63:2374-2378 (1989); Miller et al., J. Virol. 65:2220-2224 (1991); PCT/US94/05700).

In applications where transient expression of the ZFP is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). See, e.g., Examples 1.

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., Blood 85:3048-305 (1995); Kohn et al., Nat. Med. 1:1017-102 (1995); Malech et al., PNAS 94:22 12133-12138 (1997)). PA317/pLASN was the first therapeutic vector used in a gene therapy trial. (Blaese et al., Science 270:475-480 (1995)). Transduction efficiencies of 50% or greater have been observed for MFG-S packaged vectors. (Ellem et al., Immunol Immunother. 44(1):10-20 (1997); Dranoffet al., Hum. Gene Ther. 1:111-2 (1997).

Recombinant adeno-associated virus vectors (rAAV) is another alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., Lancet 351:9117 1702-3 (1998), Kearns et al., Gene Ther. 9:748-55 (1996)).

Replication-deficient recombinant adenoviral vectors (Ad) are predominantly used for colon cancer gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiply types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., Hum. Gene Ther. 7:1083-9 (1998)). Additional examples of the use of adenovirus vectors for gene transfer in clinical trials include Rosenecker et al., Infection 24:1 5-10 (1996); Sterman et al., Hum. Gene Ther. 9:7 1083-1089 (1998); Welsh et al., Hum. Gene Ther. 2:205-18 (1995); Alvarez et al., Hum. Gene Ther. 5:597-613 (1997); Topfet al., Gene Ther. 5:507-513 (1998); Sterman et al., Hum. Gene Ther. 7:1083-1089 (1998).

Packaging cells are used to form virus particles that are capable of infecting a host cell. Such cells include 293 cells, which package adenovirus, and .psi.2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome that are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

As stated above, various viral delivery vehicles, as are known in the art, can be used to introduce a nucleic acid (e.g., a nucleic acid encoding a zinc finger protein) into a cell. The choice of delivery vehicle depends upon a number of factors, including but not limited to the size of the nucleic acid to be delivered and the desired target cell.

In certain embodiments, adenoviruses are used as delivery vehicles. Exemplary adenovirus vehicles include Adenovirus Types 2, 5, 12 and 35. For example, vehicles useful for introduction of transgenes into hematopoietic stem cells, e.g., CD34+cells, include adenovirus Type 35. Additional adenoviral vehicles include the so-called "gutless" adenoviruses. See, for example, Kochanek et al. (1996) *Proc. Natl. Acad. Sci. USA* 93:5,731-5,736.

Lentivirus delivery vehicles have been described, for example, in U.S. Pat. Nos. 6,312,682 and 6,669,936 and in U.S. Patent Application Publication No. 2002/0173030 and can be used, e.g., to introduce transgenes into immune cells (e.g., T-cells). Lentiviruses are capable of integrating a DNA copy of their RNA genome into the genome of a host cell. See, for example, Ory et al. (1996) *Proc. Natl. Acad. Sci. USA* 93:11382-11388; Miyoshi et al. (1998) *J. Virology* 72:8150-8157; Dull et al. (1998) *J. Virol.* 72:8463-8471; Zuffery et al. (1998) *J. Virol.* 72:9873-9880; Follenzi et al. (2000) *Nature Genetics* 25:217-222 and Delenda (2004) *J Gene Medicine* 6:S 125-S 138. In certain lentiviral vehicles, this integration function has been disabled to generate non-integrating lentivirus vehicles. See, for example, Poon et al. (2003) *J. Virology* 77:3962-3972 and Vargas et al. (2004) *Human Gene Therapy* 15:361-372. The use of both integrating and non-integrating lentivirus vectors for transduction of hematopoietic stem cells has been described by Haas et al. (2000) *Mol. Therapy* 2:71-80. Transduction of CD4+ T-cells with integrating lentivirus vectors has been described by Humeau et al. (2004) Mol. Therapy 9:902-913.

Herpes simplex virus vehicles, which are capable of long-term expression in neurons and ganglia, have been described. See, for example, Krisky et al. (1998) *Gene Therapy* 5(11):1517-1530; Krisky et al. (1998) *Gene Therapy* 5(12):1593-1603; Burton et al. (2001) *Stem Cells* 19:358-377; Lilley et al. (2001) *J. Virology* 75(9):4343-4356

Methods for improving the efficiency of retroviral transduction of hematopoietic stem cells are disclosed, for example, in U.S. Pat. No. 5,928,638.

The tropism of retroviral and lentiviral delivery vehicles can be altered by the process of pseudotyping, thereby enabling viral delivery of a nucleic acid to a particular cell type. See, for example, U.S. Pat. No. 5,817,491.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., PNAS 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In some instances, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., Culture of Animal Cells, A Manual of Basic Technique (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+cells in vitro into clinically important immune cell types using cytokines such a GM-CSF, IFN-Y and TNF-$\alpha$ are known (see Inaba et al., J. Exp. Med. 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panb cells), GR-1 (granulocytes), and lad (differentiated antigen presenting cells) (see Inaba et al., J. Exp. Med. 176:1693-1702 (1992)).

Vectors (e.g., retroviruses, adenoviruses, liposomes, etc.) containing therapeutic ZFP nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions, as described below (see, e.g., Remington's Pharmaceutical Sciences, 17th ed., 1989).

B. Protein Compositions

An important factor in the administration of polypeptide compounds, such as the present ZFPs, is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as ZFPs across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629-634 (1996)). Another subsequence, the h (hydrophobic) domain of signal peptides, was found to have similar cell membrane translocation characteristics (see, e.g., Lin et al., J. Biol. Chem. 270: 14255-14258 (1995)).

Examples of peptide sequences which can be linked to a ZFP, for facilitating uptake of ZFP into cells, include, but are not limited to: an 11 amino acid peptide of the tat protein of HIV; a 20 residue peptide sequence which corresponds to amino acids 84-103 of the p16 protein (see Fahraeus et al., Current Biology 6:84 (1996)); the third helix of the 60-amino acid long homeodomain of Antennapedia (Derossi et al., J. Biol. Chem. 269:10444 (1994)); the h region of a signal peptide such as the Kaposi fibroblast growth factor (K-FGF) h region (Lin et al., supra); or the VP22 translocation domain from HSV (Elliot & O'Hare, Cell 88:223-233 (1997)). Other suitable chemical moieties that provide enhanced cellular uptake may also be chemically linked to ZFPs. Membrane translocation domains (i.e., internalization domains) can also be selected from libraries of randomized peptide sequences. See, for example, Yeh et al. (2003) *Molecular Therapy* 7(5): S461, Abstract #1191.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., J. Biol. Chem., 268:3334-3341 (1993); Perelle et al., Infect. Immun., 61:5147-5156 (1993); Stemnark et al., J. Cell Biol. 113:1025-1032 (1991); Donnelly et al., PNAS 90:3530-3534 (1993); Carbonetti et al., Abstr. Annu. Meet. Am. Soc. Microbiol. 95:295 (1995); Sebo et al., Infect. Immun. 63:3851-3857 (1995); Klimpel et al., PNAS U.S.A. 89:10277-10281 (1992); and Novak et al., J. Biol. Chem. 267:17186-17193 1992)).

Such subsequences can be used to translocate ZFPs across a cell membrane. ZFPs can be conveniently fused to or derivatized with such sequences. Typically, the translocation sequence is provided as part of a fusion protein. Optionally, a linker can be used to link the ZFP and the translocation sequence. Any suitable linker can be used, e.g., a peptide linker.

The ZFP can also be introduced into an animal cell, preferably a mammalian cell, via a liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, i.e., a ZFP. The liposome fuses with the plasma membrane, thereby releasing the drug into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound (in this case, a ZFP) at the target tissue or cell. For systemic or tissue specific delivery, this can be accomplished, for example, in a passive manner wherein the liposome bilayer degrades over time through the action of various agents in the body. Alternatively, active drug release involves using an agent to induce a permeability change in the liposome vesicle. Liposome membranes can be constructed so that they become destabilized when the environment becomes acidic near the liposome membrane (see, e.g., PNAS 84:7851 (1987); Biochemistry 28:908 (1989)). When liposomes are endocytosed by a target cell, for example, they become destabilized and release their contents. This destabilization is termed fusogenesis. Dioleoylphosphatidylethanolamine (DOPE) is the basis of many “fusogenic” systems.

Such liposomes typically comprise a ZFP and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., Ann. Rev. Biophys. Bioeng. 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91.backslash.17424, Deamer & Bangham, Biochim. Biophys. Acta 443:629-634 (1976); Fraley, et al., PNAS 76:3348-3352 (1979); Hope et al., Biochim. Biophys. Acta 812:55-65 (1985); Mayer et al., Biochim. Biophys. Acta 858:161-168 (1986); Williams et al., PNAS 85:242-246 (1988); Liposomes (Ostro (ed.), 1983, Chapter 1); Hope et al., Chem. Phys. Lip. 40:89 (1986); Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vesicles and ether-fusion methods, all of which are well known in the art.

In some instances, liposomes are targeted using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957,773 and 4,603,044).

Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see Renneisen et al., J. Biol. Chem., 265:16337-16342 (1990) and Leonetti et al., PNAS 87:2448-2451(1990).

C. Dosage

For therapeutic applications of ZFPs, the dose administered to a patient should be sufficient to affect a beneficial therapeutic response in the patient over time. The dose will be determined by the efficacy and Kd of the particular ZFP employed, the nuclear volume of the target cell, and the condition of the patient, as well as the body weight or surface area of the patient to be treated. The size of the dose also will be determined by the existence, nature, and extent of any adverse side effects that accompany the administration of a particular compound or vector in a particular patient.

In determining the effective amount of the ZFP to be administered in the treatment or prophylaxis of neuropathic pain, the physician evaluates circulating plasma levels of the ZFP or nucleic acid encoding the ZFP, potential ZFP toxicities, progression of the disease, and the production of anti-ZFP antibodies. Administration can be accomplished via single or divided doses.

D. Compositions and Modes of Administration

1. General

ZFPs and the nucleic acids encoding the ZFPs can be administered directly to a subject (e.g., patient) for modulation of gene expression and for therapeutic or prophylactic applications. In general, and in view of the discussion herein, phrases referring to introducing a ZFP into an animal or patient can mean that a ZFP or ZFP fusion protein is introduced and/or that a nucleic acid encoding a ZFP or ZFP fusion protein is introduced in a form that can be expressed in the animal. For example, as described in greater detail in the following section, the ZFPs and/or nucleic acids can be used in the treatment of chronic pain.

Administration of therapeutically effective amounts is by any of the routes normally used for introducing ZFP into ultimate contact with the tissue to be treated. The ZFPs are administered in any suitable manner, preferably with pharmaceutically acceptable carriers (e.g., poloxamer and/or buffer). Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there are a wide variety of suitable formulations of pharmaceutical compositions (see, e.g., Remington’s Pharmaceutical Sciences, 17th ed. 1985)).

The ZFPs, alone or in combination with other suitable components, can be made into aerosol formulations (i.e., they can be “nebulized”) to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of the disclosed methods, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

2. Exemplary Delivery Options

A variety of delivery options are available for the delivery of the pharmaceutical compositions provided herein so as to modulate expression of genes involved in neuropathic pain. Depending upon the particular indication (e.g., which nerve(s) involved in the pain), the compositions can be targeted to specific areas or tissues of a subject. For example, in some methods, one delivers compositions to specific regions of the body to treat pain. Other treatments, in contrast, involve administering the composition in a general manner without seeking to target delivery to specific regions.

A number of approaches can be utilized to localize the delivery of agents to particular regions. Certain of these methods involve delivery to the body lumen or to a tissue (see, e.g., U.S. Pat. Nos. 5,941,868; 6,067,988; 6,050,986; and 5,997,509; as well as PCT Publications WO 00/25850; WO 00/04928; 99/59666; and 99/38559). Options for the delivery of compositions to modulate genes involved in neuropathic pain include systemic administration using intravenous or subcutaneous administration, and tissue engineering (U.S. Pat. No. 5,944,754). Various vectors can be used to deliver polynucleotides to sensory neurons and/or ganglia. See, e.g., Glorioso et al. (2003) Curr Opin Mol Ther. 5(5):483-488. See also Fleming et al. (2001) *Hum Gene Ther.* 12(1):77-86; Goins et al. (1999) *J. Virol.* 73(1):519-532; Xu et al. (2003) *Proc Natl Acad Sci USA* 100(10): 6204-6209 and Glatzel et al. (2000) *Proc Natl Acad Sci USA* 97(1):442-447.

Other delivery methods known by those skilled in the art include the methods disclosed in U.S. Pat. Nos. 5,698,531; 5,893,839; 5,797,870; 5,693,622; 5,674,722; 5,328,470; and 5,707,969.

IX. Applications

A. General

ZFPs engineered to bind a chosen target site in a gene of interest, and nucleic acids encoding them, can be utilized to modulate expression of a target gene (e.g., genes involved in neuropathic pain) in any subject and by so doing, treat neuropathic pain. Generally, a target site of a nucleic acid within a cell or population of cells is contacted with a ZFP that has binding specificity for that target site. Methods can be performed in vitro with cell cultures or in vivo. Certain methods are performed such that chronic pain is treated by repressing expression of one or more genes involved hyper-excitability (e.g., VR1, TRK-A, and/or NAV1.8).

B. Transgenic/Knockout Animals

Using the compositions and methods described herein, transgenic animals can be generated using standard techniques. In addition, gene knockouts (e.g., of VR1, TRK-A, and/or NAV1.8) or knockdowns can also be generated. For example, a ZFP as described herein, which is targeted to one or more genes involved in neuropathic pain, is administered to any animal in order to create a knockout or knockdown animal. These animals are useful as models for disease and for drug testing. Thus, ZFP repressors as described herein make it possible to reduce or eliminate gene (e.g., VR1, TRK-A, and/or NAV1.8) activity in any animal model, for which no feasible ways currently exist to generate knockouts. Furthermore, as many accepted animal models for studying chronic pain and evaluating candidate drugs are non-mouse models, the ability to create these knockouts/knockdowns in any animal using the ZFPs described herein represents an important advance in the field.

In addition, animal models for screening can be generated by using ZFPs comprising a transcriptional activation domain to up-regulate expression of, e.g., VR1, TrkA or NaV 1.8 genes.

C. Therapeutic Applications

The ZFPs provided herein and the nucleic acids encoding them such as in the pharmaceutical compositions described herein can be utilized to modulate (e.g., activate or repress) expression of one or more genes involved in nerve excitability, thereby modulating chronic pain. Modulation of nerve excitability can result in the amelioration or elimination of chronic pain. For example, genes overexpressed in chronic pain can be repressed using targeted ZFPs both in cell cultures (i.e., in in vitro applications) and in vivo to decrease nerve hyper-excitability and thereby treat chronic pain. Because ZFP repressors as described herein do not significantly change the expression levels of any other genes (see, Examples), they are likely to be more specific than antisense methods. Unlike the antisense approach, which needs to target a large number of copies of mRNA, there are a limited number of binding sites in each cell to be targeted by a ZFP, i.e., the chromosomal copies of the target gene(s), therefore, ZFPs can function at a relatively low expression level.

Hence, certain methods for treating chronic pain involve introducing a ZFP targeted to one or more of VR1, TRK-A, and/or NAV1.8 into an animal. Binding of the ZFP bearing a repression domain to its target site results in decreased nerve excitability and amelioration (or elimination) of neuropathic pain. Typically, a repression domain fused to the ZFP represses the expression of the target gene.

A variety of assays for assessing gene expression as it relates to nerve excitability and pain are known. For example, electrophysiological recordings (e.g., to determine hyper-excitability and/or spontaneous activity) can be obtained. See, e.g., Liu et al. (2001) Neuroscience 105(1): 265-75; Cain et al. (2001) J. Neurosci. 21(23):9367-76. Heat sensitization can also be measured. Other options that may be used alone or in combination with any of the above assay methods are immunostaining of nerves and/or of overlying tissue (e.g., skin), for example to determine morphological changes (e.g., branching, decrease in fibers, etc). In addition, microscopic examination of tissue sections can be performed. These and other methods are accepted assays and the results can also be extrapolated to other systems.

Additional assays are described, for example, by Lutfy et al. (1997) *Pain* 70(1):31-40; Foo et al. (1993) *Pharmacol Biochem Behav* 45(2):501-505 and Eaton et al. (2002) *Gene Ther.* 9(20):1387-1395.

The compositions provided herein can also be utilized to activate expression of genes in therapeutic applications. In these instances, a ZFP engineered to bind a target site in a gene is fused to a transcriptional activation domain. Exemplary genes whose activation can be used to treat neuropathic pain include those encoding brain-derived neurotrophic factor (BDNF), glial-derived neurotrophic factor (GDNF) and nerve growth factor (NGF).

The following examples are provided solely to illustrate in greater detail particular aspects of the disclosed methods and compositions and should not be construed to be limiting in any way.

EXAMPLE 1

Materials and Methods

A. Cell Culture and Transfection

Rat C6 cells were cultured in DMEM with 10% FBS. Nucleofection was carried out according the manufacture's protocol (Amaxa Biosystems, Cologne, Germany). In brief, $2\times10^6$ cells and 2 μg plasmid DNA were mixed with 1001 μNucleofector Solution V. After electroporation with the Nucleofector program U-30, the cells were plated into 6-well plates. Cells were harvested 72 hours post-transfection.

Rat ND8/34 cells were cultured in DMEM with 20% FBS. Cells were seeded into 24-well plates at the density of $\sim1.5\times10^5$ cells/well 16 to 24 hours prior to transfection. Duplicate transfections were performed for each construct using FuGENE 6 transfection reagents (Roche, Indianapolis, Ind.). 0.25 μg of the ZFP-TF expression plasmid or control plasmid and 0.05 μg of the puromycin resistance plasmid were transfected into each well using 0.75 μl of Fugene 6 reagent. Transfection reagent-containing media was removed after 8-16 hours and fresh media containing 2

μg/ml puromycin was added. Cells were harvested 72 hours post-transfection for RNA isolation.

Human IMR32 cells were cultured in DMEM with 20% FBS. Cells were seeded into 24-well plates at the density of ~$1.5\times10^5$ cells/well 16 to 24 hours prior to transfection. Triplicate transfections were performed for each construct using Lipofectamine 2000 transfection reagents (Invitrogen). For each well, 0.25 ug ZFP repressor plasmids were mixed with 1 μl of Lipofectamine 2000 transfection reagents for 30 minutes. The complex was then added into the culture. Transfection reagent-containing media was removed after 8 hours and fresh media was added. Cells were harvested 72 hours post-transfection.

B. Drug Selection to Enrich for Transgene-positive Cells

To enrich the transfected cell population, a drug selection protocol was performed to kill untransfected cells. 1.2 μg of the ZFP-TF expression plasmid or control plasmid were co-transfected with 0.3 μg of puromycin resistance vector. At 24 hours post-transfection, puromycin was added to the media. After 60 hours of puromycin selection, most untransfected cells were killed. The resistant cells were harvested for subsequent RNA analysis.

C. Tagman® Analysis

RNA was isolated using the RNeasy Kit (Qiagen, Valencia, Calif.). Taqman assays were performed as previously described (J. Biol. Chem. 275 33850). In brief, TaqMan was performed in 96-well plate format on ABI 7700 SDS machine (Perkin Elmer, Boston, Mass.) and analyzed with SDS version 1.6.3 software. RNA samples (25 ng) were mixed with 0.1 μM of probe and optimal amount of each primer, 5.5 mM $MgCl_2$ and 0.3 mM (each) dNTP, 0.625 unit of AmpliTaq Gold DNA Polymerase, 6.25 units of MultiScribe Reverse Transcriptase, and 5 units of RNase Inhibitor in 1× TaqMan buffer A from PE. The reverse transcription reactions were performed at 48° C. for 30 minutes. After denaturing at 95° C. for 10 minutes, PCR amplification reactions were conducted for 40 cycles at 95° C. for 15 seconds and at 60° C. for 1 minute. The levels of the target gene and 18S mRNA were quantified using standard curves sparming a 125-fold concentration range (relative levels of 0.2 to 25; five-fold dilution series). Each RNA sample was assayed in duplicate Taqman reactions. The ratio of target/18S was used to determine the relative levels of the target RNA in various samples. Sequences and concentrations of primers and probes are provided in Table 1.

For VR1 and TrkA, Taqman analysis, the reverse transcription step is performed using a poly dT primer instead of the gene specific primer pair. This allows us to analyze exclusively polyadenylated messenger RNA (and thereby increases our chances to observe a decrease in the transcript levels). 50 ng of oligo dT (12-18) primer (Invitrogen) are added in the reaction mix. The reverse transcription reaction is performed at 48° C. for 60 minutes and then the reverse transcriptase is inactivated at 95° C. for 5 minutes. The gene-specific primers are then added to the reaction, and the PCR reaction is performed as described above. Sequences and concentrations of primers and probes are provided in Table 8.

TABLE 8

TAQMAN ® REAGENTS

| Gene Target | Oligonucleotide name | Sequence (5'--> 3') | μM/rxn | SEQ ID NO. |
|---|---|---|---|---|
| 18S | 18S-For1 | TTCCGATAACGAACGAGACTCT | 0.3 | 215 |
| | 18S-Rev1 | TGGCTGAACGCCACTTGTC | 0.3 | 216 |
| | 18S-Pro1** | TAACTAGTTACGCGACCCCCCGAG | 0.1 | 217 |
| rat VR1 | rVR1-For1 | CCTGTGAAAAGAACTCGGTTCTG | 0.9 | 218 |
| | rVR1-Rev1 | TCCACGAGAAGCATGTCATGA | 0.9 | 219 |
| | rVR1-Pro1** | TCGCTTACAGCAGCAGTGAGACCCCTA | 0.1 | 220 |
| rat TrkA | r TrkA -For1 | CATGGAGAACCCACAGTACTTCAG | 0.9 | 221 |
| | r TrkA -Rev 1 | CCCCTAGCTCCCACTTGAGAA | 0.9 | 222 |
| | r TrkA -Pro1** | ACCTGTGTCCACCATATCAAGGGCCA | 0.1 | 223 |
| human NAV1.8 | r NAV1.8-For1 | TCTTCTTCACCACCTACATCAT | 0.3 | 224 |
| | r NAV1.8-Rev1 | CCAGGTCTCATAGAACATGTC | 0.1 | 225 |
| | r NAV1.8-Pro1** | CCTTCCTCATCGTGGTCAACATGTA | 0.1 | 226 |

Note: Asterisks (**) denote probes. Probe ends are labeled with: 5'-- 6FAM; and 3'-- BHQ1("Black Hole Quencher 1" ® -- Biosearch).

D. Immunodetection and FACS Analysis

Cells were resuspended by incubation in PBS+EDTA 0.5 mM for 5-10 minutes at room temperature. After centrifugation for 5 minutes at 1000 rpm, cells were resuspended in PBS+1% Tween 20+8% powdered milk (used as a blocking reagent) and incubated at 4° C. for 30 minutes. The cell suspension was then centrifuged and, after discarding the supernatant, resuspended in the primary antibody solution (diluted at 1/100 in PBS+1% Tween 20+1% powdered milk). The cells were incubated at 4° C. for 1 hour.

After incubation, the cells were washed three times in a PBS+1% Tween 20 solution, and resuspended in the secondary antibody solution (goat anti-rabbit IgG-PE, Santa Cruz Biotechnology, sc 3739, diluted at 1/100 in PBS+1% Tween 20+1% powdered milk). The cells were incubated at 4° C. for 1 hour.

Following this step, the cells were washed three times in a PBS+1% Tween 20 solution, and resuspended in the tertiary antibody solution (bovine anti-goat IgG-PE, Santa Cruz Biotechnology, sc 3747, diluted at 1/100 in PBS+1% Tween 20+1% powdered milk). The cells were incubated at 4° C. for 1 hour.

After three washes in a PBS+1% Tween 20 solution, the cells were resuspended in a PBS solution containing 1% fetal bovine serum. The analysis was performed using a Facscalibur (Becton Dickinson) flow cytometer according to the manufacturer's instructions and the intensity of the phycoerythrin fluorescent labeling in the different samples was measured.

EXAMPLE 2

Repression of VR1 in C6 Cells

Fusion proteins comprising 6-fingered zinc finger proteins designed to recognize a target site in rat VR1 (rVR1) and a repression domain were designed as described above in and in U.S. Pat. No. 6,607,882. The designed ZFPs and the target sites recognized by these ZFPs are shown in Tables 1 and 2. In order to test the ZFPs designed as above and shown in Tables 2, the following experiments were conducted.

A. Gene Expression

Sequences encoding a fusion protein comprising a rVR1-targeted ZFP (6150, 6332, 6337 and 6338) and a repression domain (KOX) were introduced into a pcDNA3.1 plasmid backbone (Invitrogen, Carlsbad, Calif.) to create rVR1-targeted ZFP expression plasmids. The fusion proteins were designated 6150-KOX, 6332-KOX, 6337-KOX and 6338-KOX. Empty pcDNA3.1 plasmid vectors were also prepared for use as controls.

Plasmids vectors including one of 6150-KOX, 6332-KOX, 6337-KOX and 6338-KOX were transfected into cultured Rat C6 cells as described in Example 1. Empty vectors were used as controls. ZFP expression was measured by Taqman assay as described in Example 1.

Figure 2:
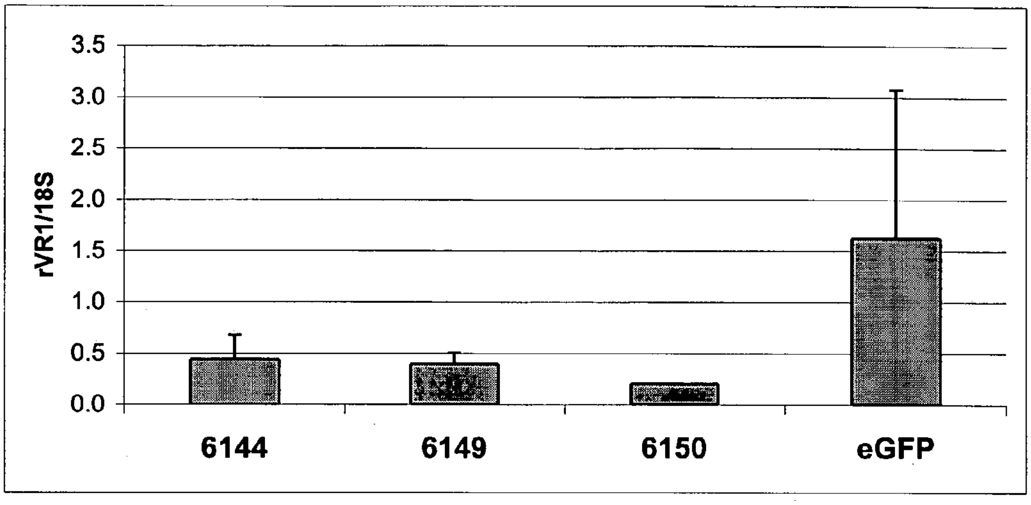
FIG. 2 is a graph depicting repression of VR1 gene expression in rat cells transfected with a plasmid encoding a fusion of a KOX repression domain and a VR1-targeted ZFP (designated 6144, 6149, 6150). The fusion proteins are designated 6144-KOX, 6149-KOX, and 6150-KOX. "eGFP" refers to an enhanced Green Fluorescent Protein (GFP) control.

FIGS. 1 and 2 show the results of repression of rat VR1 expression using 6332-KOX, 6337-KOX or 6338-KOX. Administration of rVR1-targeted ZFPs significantly repressed rat VR1 expression.

B. Protein Expression

Figure 3:
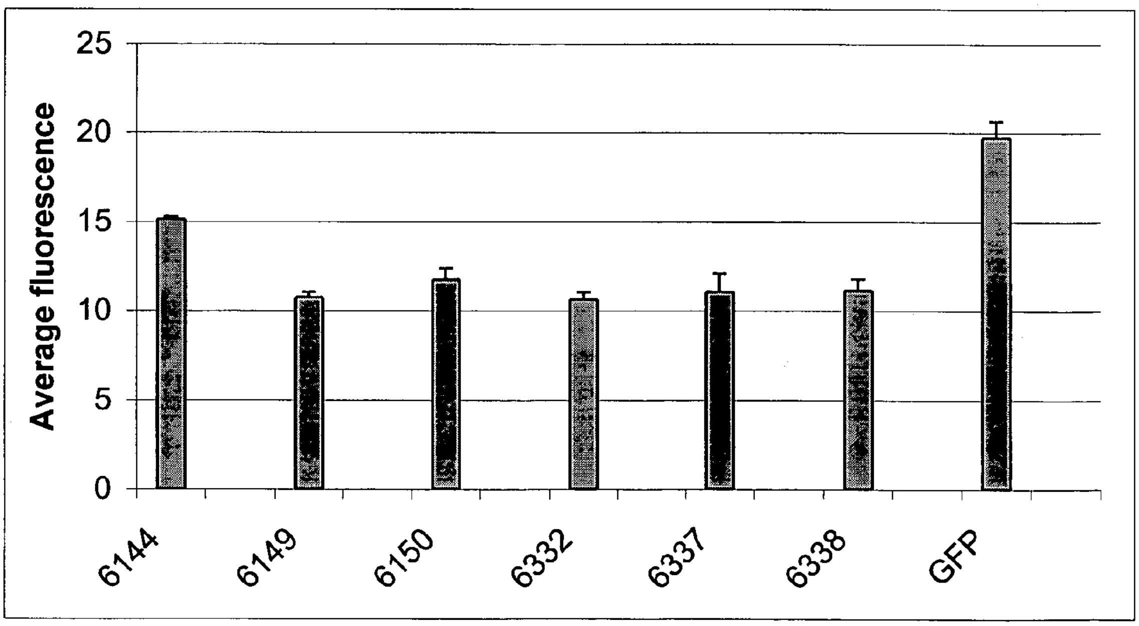
FIG. 3 is a graph depicting results of FACS and shows repression of VR1 protein levels in rat cells transfected with a plasmid encoding 6144-KOX, 6149-KOX, 6150-KOX a fusion of a KOX repression domain and a VR1-targeted ZFP (designated 6144, 6149, 6150). The fusion proteins are designated 6144-KOX, 6149-KOX, 6150-KOX, 6332-KOX, 6337-KOX, and 6338-KOX. "GFP" refers to a FACS results obtained with a GFP control.

Repression of rVR1 was also demonstrated at the protein level using an immunofluorescent labeling assay described in Example 1. ZFP repressors expression plasmids were transfected into rat C6 cell cultures using Fugene 6 reagent (Roche, Cat. #1 814 443). To increase the proportion of cells having received the expression plasmid, a puromycin-resistance plasmid was co-transfected with either the ZFP plasmid or the control vector (cells were selected with 2 ug/ml puromycin for two days to kill untransfected cells). The primary antibody used for detection of rVR1 protein is anti-rat VR1 (rabbit polyclonal), ABR PA1-747 (see Immunodetection protocol, Example 1). This experiment revealed that 6144, 6149, 6150, 6332, 6337 and 6338 down-regulate the expression of rVR1 at the protein level. (FIG. 3).

In this analysis, the average fluorescence was determined using the cell population between the fluorescence values of 2 and 100. For each sample, this encompassed >95% of the cells. FIG. 3.

Thus, VR1-targeted ZFPs repress expression of rVR1 at the nucleotide and protein levels.

EXAMPLE 3

Repression of TRKA Expression

A. Gene Expression

Figure 4:
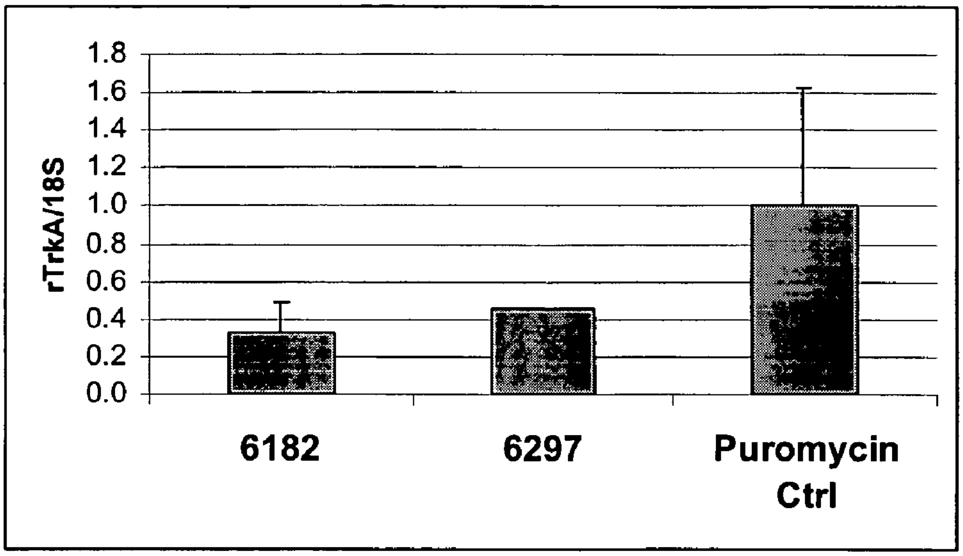
FIG. 4 is a graph depicting repression of TrkA gene expression by in rat cells transfected with a plasmid encoding a fusion of a KOX repression domain and a TrkA-targeted ZFP (designated 6182, 6297) and a plasmid encoding puromycin resistance. Puromycin selection is used to kill untransfected cells. The fusion proteins are designated 6182-KOX and 6297-KOX. "Puromycin cntrl" refers to controls co-transfected with a control plasmid and the plasmid encoding puromycin resistance.

Expression plasmids comprising ZFP repressors shown in Table 3 were transfected into ND8/34 cell cultures (mouse neuroblastoma/rat DRG neuron hybrid cell line) using the Fugene 6 reagent. To increase the proportion of cells having received the expression plasmid, a puromycin-resistance plasmid was co-transfected with either the ZFP plasmid or the control vector. Cells were selected with 2 μg/ml puromycin for two days to kill untransfected cells. As shown FIG. 4, 6182-KOX and 6297-KOX down-regulate the expression of rTrkA at the mRNA level.

B. Protein Expression

Figure 5:
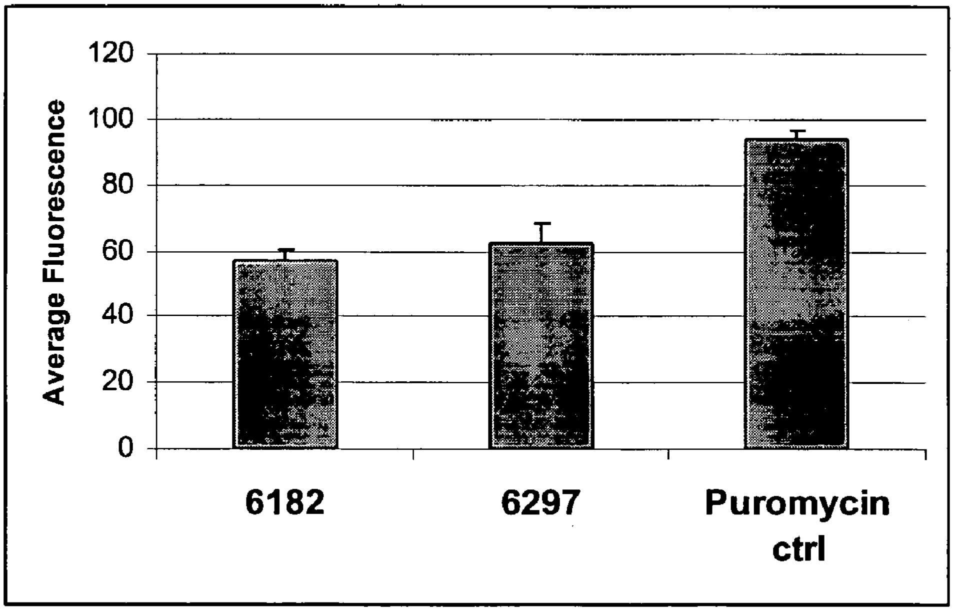
FIG. 5 is a graph depicting FACS results of FACS and shows repression of TrkA protein levels in rat cells co-transfected with a plasmid encoding 6182-KOX or 6297-KOX and a plasmid encoding puromycin resistance. "Puromycin cntrl" refers to controls co-transfected with a control plasmid and the plasmid encoding puromycin resistance.

Repression of rTrkA was also demonstrated at the protein level. ZFP repressors expression plasmids were transfected into ND8/34 cell cultures using Fugene 6 reagent. To increase the proportion of cells having received the expression plasmid, a puromycin-resistance plasmid was co-transfected with either the ZFP plasmid or the control vector (cells were selected with 2 ug/ml puromycin for two days to kill untransfected cells). The primary antibody used in this assay was anti TrkA (rabbit polyclonal), Upstate #06574 (see Immunodetection protocol, Example 1). Average fluorescence was determined using the cell population between the fluorescence values of 0 and 1000. For each sample, this encompassed >99% of the cells. As shown in FIG. 5, TRKA-targeted ZFPs effectively down-regulate the expression of rTrkA at the protein level.

Thus, VR1-targeted ZFPs repress expression of rTRKA at the nucleotide and protein levels.

EXAMPLE 4

Repression of NAV1.8 Expression

Figure 6:
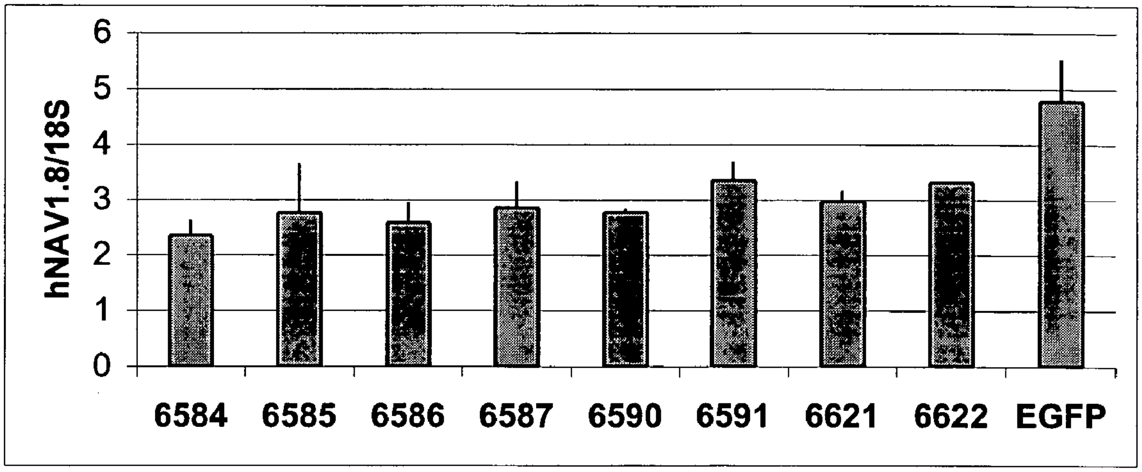
FIG. 6 is a graph depicting repression of NAV1.8 in human cells transfected with a plasmid encoding a fusion of a KOX repression domain and a NAV1.8-targeted ZFP (designated 6584, 6585, 6586, 6587, 6590, 6591, 6621, and 6622). The fusion proteins are designated 6584-KOX, 6585-KOX, 6586-KOX, 6587-KOX, 6590-KOX, 6591-KOX, 6621-KOX, and 6622-KOX. "eGFP" refers to an enhanced Green Fluorescent Protein (GFP) control.

ZFP repressors expression plasmids were transfected into IMR32 cell cultures (human neuroblastoma cells). The transfection was performed using the Lipofectamine 2000 protocol (Invitrogen, #11668-019), which gave ~80% transfection efficiency. As shown in FIG. 6, NAV1.8-targeted ZFPs 6584, 6585, 6586, 6587, 6590, 6591, 6621 and 6622 (linked to the Kox domain) down-regulate the expression of hNAV1.8.

EXAMPLE 5

Repression of Human TRKA Expression

Plasmids encoding fusions of various human TrkA-targeted zinc finger proteins (Table 5) with a KOX repression domain were constructed using standard molecular biological techniques. See, for example, co-owned U.S. Pat. Nos. 6,453,242 and 6,534,261. Expression of the fusion proteins was controlled by a human EF-1α promoter, included in the plasmid in operative linkage to sequences encoding the fusion proteins. The EF-1α promoter was chosen because it functions effectively in neural cells and cell lines, and its activity can be enhanced by the presence of all-trans-retinoic acid in the cellular culture medium.

The chronic myelogenous leukemia cell line K562 was chosen for testing TrkA repression, because they grow well in suspension, express TrkA and can be transfected with high efficiency. Cells were cultured in 6-well dishes to a concentration of 2×106 cells per well in the presence of 1 mM all-trans-retinoic acid. Plasmids were introduced into K562 cells by nucleofection (Amaxa, Solution V, Program T-16), and transfection efficiencies of >90% were routinely achieved.

RNA Analysis 72 hours after transfection, RNA was isolated using a RNeasy Mini Kit (Qiagen, Valencia, Calif.). 25 ng of total RNA was assayed by reverse transcription and real-time PCR (TaqMan®) in a 96-well format using an ABI 7700

Figure 7:
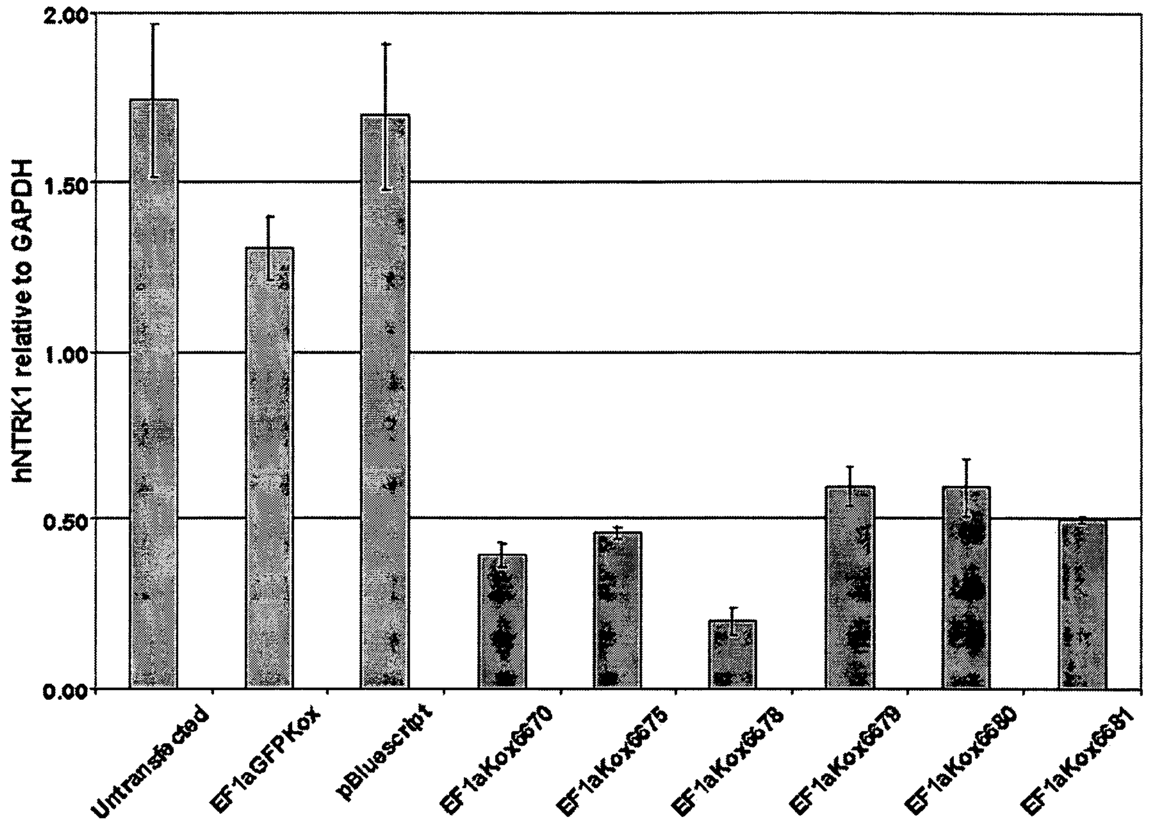
FIG. 7 is a graph showing levels of human TrkA mRNA, normalized to human GAPDH mRNA, in K562 cells transfected with plasmids encoding ZFP/KOX fusion proteins. The identity of the encoded protein is shown on the abscissa: EF-1a refers to the promoter controlling expression of the fusion protein; Kox refers to the presence of a KOX repression domain in the encoded protein, and the number refers to the particular TrkA-targeted zinc finger binding domain (see Tables 1 and 5 for DNA target sequences and recognition domain amino acid sequences, respectively, for these zinc finger domains). EF-1aGFPKox and pBluescript are control plasmids: EF-1aGFPKox lacks an engineered zinc finger binding domain; pBluescript is a vector lacking sequences encoding a fusion protein. Bars show the standard error of the mean for duplicate determinations.

Sequence Detection System (Perkin-Elmer Life Sciences). TrkA mRNA levels were normalized to levels of GAPDH mRNA and the results are shown in FIG. 7. All of the human TrkA-specific ZFP/KOX fusion proteins repress TrkA mRNA levels; the degree of repression varies from 3-5-fold.

Protein Analysis

Samples from the same experiment in which TrkA mRNA was analyzed (above) were analyzed for TrkA protein levels (i.e. at 72 hours after transfection). Cell lysates were prepared in RIPA buffer and passed through a QIAshredder column (Qiagen, Valencia, Calif.) and analyzed on a NuPAGE 4-12% BisTris (1 mm×10 well) gel (Cat # $NP_{0321}$BOX, Invitrogen) on the Novex minigel system. The gel was blotted onto 0.2 μm pore nitrocellulose membrane (Cat # LC2000, Invitrogen) on the Xcell II blot module (Invitrogen). The blot was exposed to rabbit anti-TrkA (1:1,000 dilution, Upstate Biotechnology, NY) and rabbit anti-TFIIB (1:1,000 dilution, Santa Cruz Biotechnology) overnight at 4° C. on a rocking platform, then washed and exposed to horseradish peroxidase-conjugated goat anti-rabbit IgG (1:5,000 dilution, Santa Cruz Biotechnology) at room temperature for 2 hours with agitation. Signal was detected using a SuperSignal WestDura Extended Duration substrate and Chemiluminescence Detection Kit, both obtained from Pierce Chemical Co (Rockland, Ill.).

Figure 8:
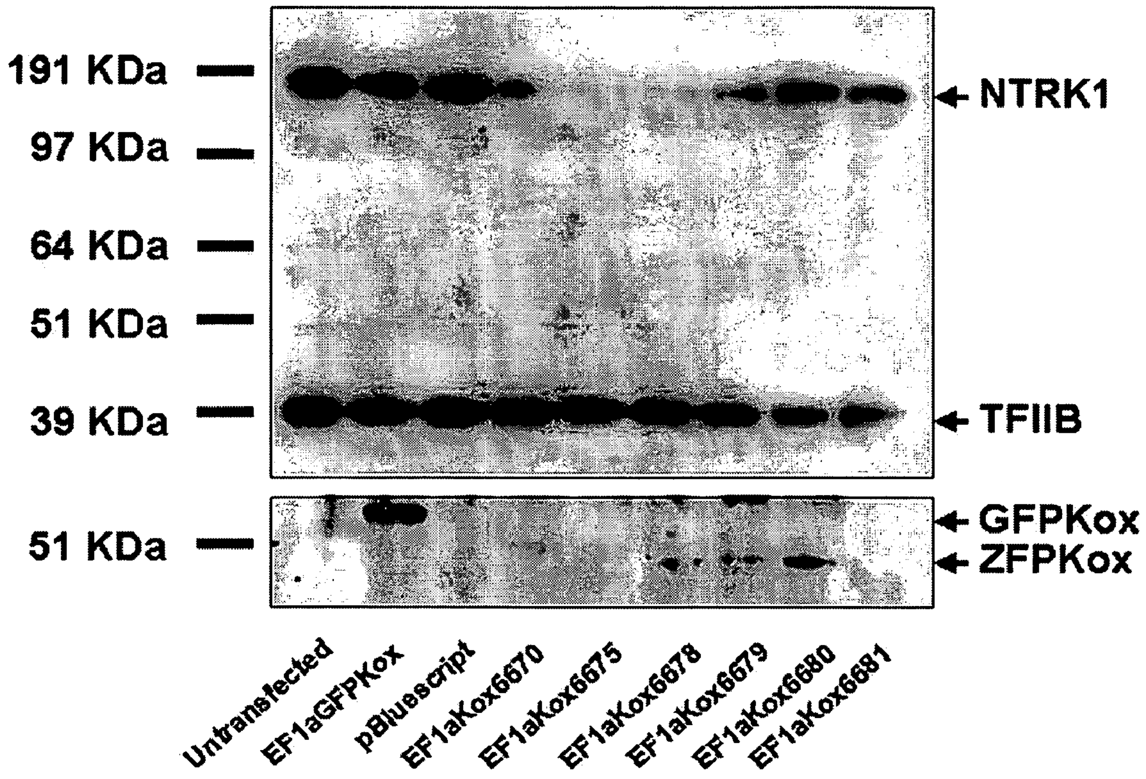
FIG. 8 is an autoradiographic image of a protein blot in which lysates from cells transfected with plasmids encoding TrkA-targeted ZFP/KOX fusion proteins were analyzed. The top panel shows assays for the presence of TrkA and TFIIB. The lower panel shows assays for the presence of the zinc finger/Kox fusion proteins, using a primary mouse anti-FLAG M2 monoclonal antibody and a donkey anti-mouse IgG-horseradish peroxidase secondary antibody. Abbreviations and protein identifications are the same as in FIG. 7.

The results, shown in FIG. 8, indicate that levels of TrkA protein are reduced after transfection of cells with TrkA-targeted ZFP/KOX fusion proteins, confirming the results obtained by analysis of TrkA mRNA.

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entireties for all purposes to the same extent as if each individual publication, patent or patent application were specifically and individually indicated to be so incorporated by reference.

What is claimed is:

1. A polynucleotide encoding a protein comprising an engineered zinc finger DNA-binding domain, wherein the DNA-binding domain comprises six zinc fingers in the following order, F1 through F6, wherein each zinc finger comprises a recognition region as follows:

F1: RKDDLIR (SEQ ID: 88)
F2: TSSSLSR (SEQ ID: 89)
F3: RSDNLSA (SEQ ID: 90)
F4: RSQNRTR (SEQ ID: 91)
F5: RSDDLSK (SEQ ID: 92)
F6: QSATRTK (SEQ ID: 39).

2. The polynucleotide of claim 1, wherein the protein further comprises a transcriptional repression domain.

3. The polynucleotide of claim 2, wherein the repression domain is a KOX repression domain.

* * * * *

SEQUENCE LISTING

```
<160> NUMBER OF SEQ ID NOS: 227

<210> SEQ ID NO 1
<211> LENGTH: 25
<212> TYPE: PRT
<213> ORGANISM: Artificial
<220> FEATURE:
<223> OTHER INFORMATION: Chemically synthesized peptide (zinc finger
      protein motif)
<220> FEATURE:
<221> NAME/KEY: MISC_FEATURE
<222> LOCATION: (1)..(25)
<223> OTHER INFORMATION: Residues 4, 5, 23, and 24 are optional
<220> FEATURE:
<221> NAME/KEY: MISC_FEATURE
<222> LOCATION: (1)..(25)
<223> OTHER INFORMATION: Residues 3-5 are optional
<220> FEATURE:
<221> NAME/KEY: MISC_FEATURE
<222> LOCATION: (1)..(25)
<223> OTHER INFORMATION: X is any amino acid

<400> SEQUENCE: 1

Cys Xaa Xaa Xaa Xaa Cys Xaa Xaa Xaa Xaa Xaa Xaa Xaa Xaa Xaa Xaa
1               5                   10                  15

Xaa Xaa His Xaa Xaa Xaa Xaa Xaa His
            20                  25


<210> SEQ ID NO 2
<211> LENGTH: 19
<212> TYPE: DNA
<213> ORGANISM: Artificial
<220> FEATURE:
<223> OTHER INFORMATION: Chemically synthesized oligonucleotide (zinc
      finger protein target)

<400> SEQUENCE: 2

tgggggtggg cattggctg                                               19


<210> SEQ ID NO 3
<211> LENGTH: 18
<212> TYPE: DNA
<213> ORGANISM: Artificial
<220> FEATURE:
```

-continued

<223> OTHER INFORMATION: Chemically synthesized oligonucleotide (zinc
finger protein target)

<400> SEQUENCE: 3
gattgggatc agctcaag 18

<210> SEQ ID NO 4
<211> LENGTH: 19
<212> TYPE: DNA
<213> ORGANISM: Artificial
<220> FEATURE:
<223> OTHER INFORMATION: Chemically synthesized oligonucleotide (zinc
finger protein target)

<400> SEQUENCE: 4
gttaagtgtg cagtaatgg 19

<210> SEQ ID NO 5
<211> LENGTH: 18
<212> TYPE: DNA
<213> ORGANISM: Artificial
<220> FEATURE:
<223> OTHER INFORMATION: Chemically synthesized oligonucleotide (zinc
finger protein target)

<400> SEQUENCE: 5
ctcaaggacg aggcaaag 18

<210> SEQ ID NO 6
<211> LENGTH: 18
<212> TYPE: DNA
<213> ORGANISM: Artificial
<220> FEATURE:
<223> OTHER INFORMATION: Chemically synthesized oligonucleotide (zinc
finger protein target)

<400> SEQUENCE: 6
cggaagaccc agaacaag 18

<210> SEQ ID NO 7
<211> LENGTH: 18
<212> TYPE: DNA
<213> ORGANISM: Artificial
<220> FEATURE:
<223> OTHER INFORMATION: Chemically synthesized oligonucleotide (zinc
finger protein target)

<400> SEQUENCE: 7
ccgcggggct aggcggtc 18

<210> SEQ ID NO 8
<211> LENGTH: 19
<212> TYPE: DNA
<213> ORGANISM: Artificial
<220> FEATURE:
<223> OTHER INFORMATION: Chemically synthesized oligonucleotide (zinc
finger protein target)

<400> SEQUENCE: 8
catgaggaag gcgagctgg 19

<210> SEQ ID NO 9
<211> LENGTH: 19
<212> TYPE: DNA
<213> ORGANISM: Artificial
<220> FEATURE:
<223> OTHER INFORMATION: Chemically synthesized oligonucleotide (zinc -continued finger protein target)

<400> SEQUENCE: 9
tccctgctcc aaggcacag 19

<210> SEQ ID NO 10
<211> LENGTH: 19
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 10
gatggacaac aaggttgag 19

<210> SEQ ID NO 11
<211> LENGTH: 19
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 11
gtgaggggac aagccaagg 19

<210> SEQ ID NO 12
<211> LENGTH: 18
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 12
tttcagtgga agaagggg 18

<210> SEQ ID NO 13
<211> LENGTH: 18
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 13
taatagagga ggaaactg 18

<210> SEQ ID NO 14
<211> LENGTH: 19
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 14
gatcaggatc agagcagtg 19

<210> SEQ ID NO 15
<211> LENGTH: 18
<212> TYPE: DNA
<213> ORGANISM: Artificial
<220> FEATURE:
<223> OTHER INFORMATION: Chemically synthesized oligonucleotide (zinc finger protein target)

-continued

<400> SEQUENCE: 15
gctgagccac tgtcactg 18

<210> SEQ ID NO 16
<211> LENGTH: 19
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 16
aaggcggggc cgggcgggg 19

<210> SEQ ID NO 17
<211> LENGTH: 20
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 17
gaggggcaag gcggggccgg 20

<210> SEQ ID NO 18
<211> LENGTH: 18
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 18
cgcaccctgc cccgatgc 18

<210> SEQ ID NO 19
<211> LENGTH: 19
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 19
gagtaggaag cgggtggag 19

<210> SEQ ID NO 20
<211> LENGTH: 18
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 20
ctgcccccac ggctcctc 18

<210> SEQ ID NO 21
<211> LENGTH: 18
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 21
agccgccgct gccctagc 18

<210> SEQ ID NO 22
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 22

Arg Ser Asp Ser Leu Ser Arg
1 5

<210> SEQ ID NO 23
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 23

Asn Asn Asp His Arg Lys Thr
1 5

<210> SEQ ID NO 24
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 24

Thr Arg Glu Asp Leu Lys Arg
1 5

<210> SEQ ID NO 25
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 25

Arg Ser Asp His Leu Ser Arg
1 5

<210> SEQ ID NO 26
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 26

Arg Ser Asp His Leu Ser Asn
1 5

<210> SEQ ID NO 27
<211> LENGTH: 7
<212> TYPE: PRT
<213> ORGANISM: Artificial

-continued

<220> FEATURE:
<223> OTHER INFORMATION: Chemically synthesized peptide (zinc finger
protein recognition region)

<400> SEQUENCE: 27

Arg Ser Asp His Arg Thr Asn
1 5

<210> SEQ ID NO 28
<211> LENGTH: 7
<212> TYPE: PRT
<213> ORGANISM: Artificial
<220> FEATURE:
<223> OTHER INFORMATION: Chemically synthesized peptide (zinc finger
protein recognition region)

<400> SEQUENCE: 28

Arg Ser Asp Asp Leu Ser Val
1 5

<210> SEQ ID NO 29
<211> LENGTH: 7
<212> TYPE: PRT
<213> ORGANISM: Artificial
<220> FEATURE:
<223> OTHER INFORMATION: Chemically synthesized peptide (zinc finger
protein recognition region)

<400> SEQUENCE: 29

Thr Ser Ser Asn Arg Thr Lys
1 5

<210> SEQ ID NO 30
<211> LENGTH: 7
<212> TYPE: PRT
<213> ORGANISM: Artificial
<220> FEATURE:
<223> OTHER INFORMATION: Chemically synthesized peptide (zinc finger
protein recognition region)

<400> SEQUENCE: 30

Arg Asn Asp Met Leu Asn Glu
1 5

<210> SEQ ID NO 31
<211> LENGTH: 7
<212> TYPE: PRT
<213> ORGANISM: Artificial
<220> FEATURE:
<223> OTHER INFORMATION: Chemically synthesized peptide (zinc finger
protein recognition region)

<400> SEQUENCE: 31

Thr Ser Ser Asn Leu Ser Arg
1 5

<210> SEQ ID NO 32
<211> LENGTH: 7
<212> TYPE: PRT
<213> ORGANISM: Artificial
<220> FEATURE:
<223> OTHER INFORMATION: Chemically synthesized peptide (zinc finger
protein recognition region)

<400> SEQUENCE: 32

Arg Ser Asp His Leu Ser Thr
1 5

-continued

<210> SEQ ID NO 33
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 33

Arg Ser Asp His Leu Ser Gln
1 5

<210> SEQ ID NO 34
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 34

Thr Ser Ser Asn Arg Ile Thr
1 5

<210> SEQ ID NO 35
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 35

Arg Ser Asp Asn Leu Ser Gln
1 5

<210> SEQ ID NO 36
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 36

Arg Ser Asn Ala Arg Thr Lys
1 5

<210> SEQ ID NO 37
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 37

Arg Ser Asp Asn Leu Ser Thr
1 5

<210> SEQ ID NO 38
<211> LENGTH: 7
<212> TYPE: PRT
<213> ORGANISM: Artificial
<220> FEATURE:
<223> OTHER INFORMATION: Chemically synthesized peptide (zinc finger protein recognition region)

-continued

<400> SEQUENCE: 38

His Asn Ala Thr Arg Ile Asn
1 5

<210> SEQ ID NO 39
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 39

Gln Ser Ala Thr Arg Thr Lys
1 5

<210> SEQ ID NO 40
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 40

Asp Ser Ala Asn Arg Ile Lys
1 5

<210> SEQ ID NO 41
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 41

Arg Ser Asp Ala Leu Ser Glu
1 5

<210> SEQ ID NO 42
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 42

Thr Ser Ser Ser Arg Lys Lys
1 5

<210> SEQ ID NO 43
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 43

Thr Lys Leu His Leu Ile Glu
1 5

<210> SEQ ID NO 44
<211> LENGTH: 7
<212> TYPE: PRT

-continued

<213> ORGANISM: Artificial
<220> FEATURE:
<223> OTHER INFORMATION: Chemically synthesized peptide (zinc finger protein recognition region)

<400> SEQUENCE: 44

Gln Ser Ala Asn Leu Ser Arg
1 5

<210> SEQ ID NO 45
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 45

Arg Ser Asp Ala Leu Ser Val
1 5

<210> SEQ ID NO 46
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 46

Asp Asn Ala Asn Arg Ile Thr
1 5

<210> SEQ ID NO 47
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 47

Arg Ser Asp Asn Leu Ser Glu
1 5

<210> SEQ ID NO 48
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 48

Ala Ser Lys Thr Arg Thr Asn
1 5

<210> SEQ ID NO 49
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 49

Arg Ser Asp Asn Leu Ser Val
1 5

-continued

<210> SEQ ID NO 50
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 50

Arg Asn Ala His Arg Ile Asn
1               5

<210> SEQ ID NO 51
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 51

Asp Ser Arg Ser Leu Thr Glu
1               5

<210> SEQ ID NO 52
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 52

Arg Arg Asp Asp Leu Ser Arg
1               5

<210> SEQ ID NO 53
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 53

Asp Asn Ser His Arg Thr Arg
1               5

<210> SEQ ID NO 54
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 54

Arg Ser Asp His Leu Ser Glu
1               5

<210> SEQ ID NO 55
<211> LENGTH: 7
<212> TYPE: PRT
<213> ORGANISM: Artificial
<220> FEATURE:
<223> OTHER INFORMATION: Chemically synthesized peptide (zinc finger protein recognition region)

-continued

<400> SEQUENCE: 55

Arg Asn Arg Asp Arg Ile Thr
1               5

<210> SEQ ID NO 56
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 56

Arg Ser Ser Asn Arg Ile Lys
1               5

<210> SEQ ID NO 57
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 57

Arg Ser Asp Asp Leu Ser Arg
1               5

<210> SEQ ID NO 58
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 58

Arg Asn Asp Asn Arg Ile Thr
1               5

<210> SEQ ID NO 59
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 59

Thr Ser Gln Asn Arg Lys Asn
1               5

<210> SEQ ID NO 60
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 60

Gln Asn Ala Thr Arg Thr Lys
1               5

<210> SEQ ID NO 61
<211> LENGTH: 7

-continued

<212> TYPE: PRT
<213> ORGANISM: Artificial
<220> FEATURE:
<223> OTHER INFORMATION: Chemically synthesized peptide (zinc finger protein recognition region)

<400> SEQUENCE: 61

Arg Ser Asp Asn Leu Ser Asn
1 5

<210> SEQ ID NO 62
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 62

Thr Asn Ser Asn Arg Ile Lys
1 5

<210> SEQ ID NO 63
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 63

Arg Ser Asp Ser Leu Ser Ala
1 5

<210> SEQ ID NO 64
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 64

Asp Arg Ser Ser Arg Thr Lys
1 5

<210> SEQ ID NO 65
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 65

His Ser His Ala Arg Ile Lys
1 5

<210> SEQ ID NO 66
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 66

Thr Ser Asp Ser Leu Thr Glu

-continued 1 5

<210> SEQ ID NO 67
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 67

Asn Arg Asp Asn Leu Ser Arg
1 5

<210> SEQ ID NO 68
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 68

Arg Ser Asp His Leu Ser Ala
1 5

<210> SEQ ID NO 69
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 69

Gln Ser Ala Thr Arg Ile Thr
1 5

<210> SEQ ID NO 70
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 70

Asp Asn Ala Asn Arg Thr Lys
1 5

<210> SEQ ID NO 71
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 71

Arg Ser Ala Val Arg Lys Asn
1 5

<210> SEQ ID NO 72
<211> LENGTH: 7
<212> TYPE: PRT
<213> ORGANISM: Artificial
<220> FEATURE:
<223> OTHER INFORMATION: Chemically synthesized peptide (zinc finger -continued protein recognition region)

<400> SEQUENCE: 72

Arg Asn Asp Asn Arg Lys Thr
1 5

<210> SEQ ID NO 73
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 73

Thr Ser Ser Ser Arg Lys Asn
1 5

<210> SEQ ID NO 74
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 74

Arg Ser Asp Val Leu Ser Glu
1 5

<210> SEQ ID NO 75
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 75

Gln Arg Asn His Arg Thr Thr
1 5

<210> SEQ ID NO 76
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 76

Asn Arg Ser Asn Arg Thr Thr
1 5

<210> SEQ ID NO 77
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 77

Arg Ser Asp Val Leu Ser Lys
1 5

<210> SEQ ID NO 78

-continued

```
<211> LENGTH: 7
<212> TYPE: PRT
<213> ORGANISM: Artificial
<220> FEATURE:
<223> OTHER INFORMATION: Chemically synthesized peptide (zinc finger
      protein recognition region)

<400> SEQUENCE: 78

Gln Asn Ala Thr Arg Ile Lys
1               5


<210> SEQ ID NO 79
<211> LENGTH: 7
<212> TYPE: PRT
<213> ORGANISM: Artificial
<220> FEATURE:
<223> OTHER INFORMATION: Chemically synthesized peptide (zinc finger
      protein recognition region)

<400> SEQUENCE: 79

Arg Ser Ser Asp Arg Thr Lys
1               5


<210> SEQ ID NO 80
<211> LENGTH: 7
<212> TYPE: PRT
<213> ORGANISM: Artificial
<220> FEATURE:
<223> OTHER INFORMATION: Chemically synthesized peptide (zinc finger
      protein recognition region)

<400> SEQUENCE: 80

Arg Ser Asp Thr Leu Ser Thr
1               5


<210> SEQ ID NO 81
<211> LENGTH: 7
<212> TYPE: PRT
<213> ORGANISM: Artificial
<220> FEATURE:
<223> OTHER INFORMATION: Chemically synthesized peptide (zinc finger
      protein recognition region)

<400> SEQUENCE: 81

Gln Lys Ala Thr Arg Thr Thr
1               5


<210> SEQ ID NO 82
<211> LENGTH: 7
<212> TYPE: PRT
<213> ORGANISM: Artificial
<220> FEATURE:
<223> OTHER INFORMATION: Chemically synthesized peptide (zinc finger
      protein recognition region)

<400> SEQUENCE: 82

His Ser Ala Asp Leu Thr Gln
1               5


<210> SEQ ID NO 83
<211> LENGTH: 7
<212> TYPE: PRT
<213> ORGANISM: Artificial
<220> FEATURE:
<223> OTHER INFORMATION: Chemically synthesized peptide (zinc finger
      protein recognition region)

<400> SEQUENCE: 83
```

-continued

```
Gln Ser Ser Asp Leu Ser Arg
1               5


<210> SEQ ID NO 84
<211> LENGTH: 7
<212> TYPE: PRT
<213> ORGANISM: Artificial
<220> FEATURE:
<223> OTHER INFORMATION: Chemically synthesized peptide (zinc finger
      protein recognition region)

<400> SEQUENCE: 84

His Ser Asp Thr Arg Lys Lys
1               5


<210> SEQ ID NO 85
<211> LENGTH: 7
<212> TYPE: PRT
<213> ORGANISM: Artificial
<220> FEATURE:
<223> OTHER INFORMATION: Chemically synthesized peptide (zinc finger
      protein recognition region)

<400> SEQUENCE: 85

Arg Asn Asp Asp Arg Lys Lys
1               5


<210> SEQ ID NO 86
<211> LENGTH: 7
<212> TYPE: PRT
<213> ORGANISM: Artificial
<220> FEATURE:
<223> OTHER INFORMATION: Chemically synthesized peptide (zinc finger
      protein recognition region)

<400> SEQUENCE: 86

Asn Ser Ser Ser Arg Ile Lys
1               5


<210> SEQ ID NO 87
<211> LENGTH: 7
<212> TYPE: PRT
<213> ORGANISM: Artificial
<220> FEATURE:
<223> OTHER INFORMATION: Chemically synthesized peptide (zinc finger
      protein recognition region)

<400> SEQUENCE: 87

Arg Asn Asp Asn Arg Lys Arg
1               5


<210> SEQ ID NO 88
<211> LENGTH: 7
<212> TYPE: PRT
<213> ORGANISM: Artificial
<220> FEATURE:
<223> OTHER INFORMATION: Chemically synthesized peptide (zinc finger
      protein recognition region)

<400> SEQUENCE: 88

Arg Lys Asp Asp Leu Ile Arg
1               5


<210> SEQ ID NO 89
<211> LENGTH: 7
<212> TYPE: PRT
<213> ORGANISM: Artificial
<220> FEATURE:
```

-continued

```
<223> OTHER INFORMATION: Chemically synthesized peptide (zinc finger
      protein recognition region)

<400> SEQUENCE: 89

Thr Ser Ser Ser Leu Ser Arg
1               5


<210> SEQ ID NO 90
<211> LENGTH: 7
<212> TYPE: PRT
<213> ORGANISM: Artificial
<220> FEATURE:
<223> OTHER INFORMATION: Chemically synthesized peptide (zinc finger
      protein recognition region)

<400> SEQUENCE: 90

Arg Ser Asp Asn Leu Ser Ala
1               5


<210> SEQ ID NO 91
<211> LENGTH: 7
<212> TYPE: PRT
<213> ORGANISM: Artificial
<220> FEATURE:
<223> OTHER INFORMATION: Chemically synthesized peptide (zinc finger
      protein recognition region)

<400> SEQUENCE: 91

Arg Ser Gln Asn Arg Thr Arg
1               5


<210> SEQ ID NO 92
<211> LENGTH: 7
<212> TYPE: PRT
<213> ORGANISM: Artificial
<220> FEATURE:
<223> OTHER INFORMATION: Chemically synthesized peptide (zinc finger
      protein recognition region)

<400> SEQUENCE: 92

Arg Ser Asp Asp Leu Ser Lys
1               5


<210> SEQ ID NO 93
<211> LENGTH: 7
<212> TYPE: PRT
<213> ORGANISM: Artificial
<220> FEATURE:
<223> OTHER INFORMATION: Chemically synthesized peptide (zinc finger
      protein recognition region)

<400> SEQUENCE: 93

Arg Ser Asp Asn Leu Ser Arg
1               5


<210> SEQ ID NO 94
<211> LENGTH: 7
<212> TYPE: PRT
<213> ORGANISM: Artificial
<220> FEATURE:
<223> OTHER INFORMATION: Chemically synthesized peptide (zinc finger
      protein recognition region)

<400> SEQUENCE: 94

Arg Ser Asp Ala Arg Thr Asn
1               5
```

-continued

<210> SEQ ID NO 95
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 95

Gln Ser Ala Asn Arg Thr Lys
1 5

<210> SEQ ID NO 96
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 96

Asn Asn Asn Ser Arg Lys Thr
1 5

<210> SEQ ID NO 97
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 97

Arg Lys Asp Thr Arg Thr Asn
1 5

<210> SEQ ID NO 98
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 98

Asp Asn Asn Ala Arg Ile Asn
1 5

<210> SEQ ID NO 99
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 99

Met Arg Ala Asp Leu Ile Arg
1 5

<210> SEQ ID NO 100
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 100

Arg Asn Thr Asp Leu Ile Arg
1 5

<210> SEQ ID NO 101
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 101

Thr Ser Ser Asp Leu Ser Arg
1 5

<210> SEQ ID NO 102
<211> LENGTH: 7
<212> TYPE: PRT
<213> ORGANISM: Artificial
<220> FEATURE:
<223> OTHER INFORMATION: Chemically synthesized peptide (zinc finger protein recognition region)

<400> SEQUENCE: 102

Ala Ser Ser Thr Arg Thr Lys
1 5

<210> SEQ ID NO 103
<211> LENGTH: 18
<212> TYPE: DNA
<213> ORGANISM: Artificial
<220> FEATURE:
<223> OTHER INFORMATION: Chemically synthesized oligonucleotide (zinc finger protein binding domain)

<400> SEQUENCE: 103
agtaaggatc aggatcag 18

<210> SEQ ID NO 104
<211> LENGTH: 18
<212> TYPE: DNA
<213> ORGANISM: Artificial
<220> FEATURE:
<223> OTHER INFORMATION: Chemically synthesized oligonucleotide (zinc finger protein binding domain)

<400> SEQUENCE: 104
ccactgtcac tgaggagg 18

<210> SEQ ID NO 105
<211> LENGTH: 19
<212> TYPE: DNA
<213> ORGANISM: Artificial
<220> FEATURE:
<223> OTHER INFORMATION: Chemically synthesized oligonucleotide (zinc finger protein binding domain)

<400> SEQUENCE: 105
cctatggccc tgtggacag 19

<210> SEQ ID NO 106
<211> LENGTH: 19
<212> TYPE: DNA
<213> ORGANISM: Artificial
<220> FEATURE:
<223> OTHER INFORMATION: Chemically synthesized oligonucleotide (zinc finger protein target)

-continued

<400> SEQUENCE: 106
gggaggggta ggtggagga 19

<210> SEQ ID NO 107
<211> LENGTH: 19
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 107
ggaggggtag gtggaggag 19

<210> SEQ ID NO 108
<211> LENGTH: 18
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 108
aaggggtccc aggccaag 18

<210> SEQ ID NO 109
<211> LENGTH: 19
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 109
caaaagggag gggtaggtg 19

<210> SEQ ID NO 110
<211> LENGTH: 18
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 110
agggaggggt aggtggag 18

<210> SEQ ID NO 111
<211> LENGTH: 18
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 111
gcatggtctc cgggtcag 18

<210> SEQ ID NO 112
<211> LENGTH: 19
<212> TYPE: DNA
<213> ORGANISM: Artificial
<220> FEATURE:
<223> OTHER INFORMATION: Chemically synthesized oligonucleotide (zinc finger protein target)

-continued

<400> SEQUENCE: 112
tctctgggtc agggttcca 19

<210> SEQ ID NO 113
<211> LENGTH: 20
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 113
ggaggggtag gtggaggagg 20

<210> SEQ ID NO 114
<211> LENGTH: 19
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 114
gaggggtagg tggaggagg 19

<210> SEQ ID NO 115
<211> LENGTH: 20
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 115
ggcctggagt ggggtccaag 20

<210> SEQ ID NO 116
<211> LENGTH: 20
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 116
agggaggggt aggtggagga 20

<210> SEQ ID NO 117
<211> LENGTH: 19
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 117
tcactgagga ggacaaacg 19

<210> SEQ ID NO 118
<211> LENGTH: 20
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 118

-continued

```
tccatgaact aggaaatatg                                                20


<210> SEQ ID NO 119
<211> LENGTH: 18
<212> TYPE: DNA
<213> ORGANISM: Artificial
<220> FEATURE:
<223> OTHER INFORMATION: Chemically synthesized oligonucleotide (zinc
      finger protein target)

<400> SEQUENCE: 119

gataagggtg agggagtg                                                  18


<210> SEQ ID NO 120
<211> LENGTH: 18
<212> TYPE: DNA
<213> ORGANISM: Artificial
<220> FEATURE:
<223> OTHER INFORMATION: Chemically synthesized oligonucleotide (zinc
      finger protein target)

<400> SEQUENCE: 120

gcaggggaat gggttcct                                                  18


<210> SEQ ID NO 121
<211> LENGTH: 19
<212> TYPE: DNA
<213> ORGANISM: Artificial
<220> FEATURE:
<223> OTHER INFORMATION: Chemically synthesized oligonucleotide (zinc
      finger protein target)

<400> SEQUENCE: 121

tcctgggagg agccaagtg                                                 19


<210> SEQ ID NO 122
<211> LENGTH: 19
<212> TYPE: DNA
<213> ORGANISM: Artificial
<220> FEATURE:
<223> OTHER INFORMATION: Chemically synthesized oligonucleotide (zinc
      finger protein target)

<400> SEQUENCE: 122

gaagaagaat gagaagatg                                                 19


<210> SEQ ID NO 123
<211> LENGTH: 18
<212> TYPE: DNA
<213> ORGANISM: Artificial
<220> FEATURE:
<223> OTHER INFORMATION: Chemically synthesized oligonucleotide (zinc
      finger protein target)

<400> SEQUENCE: 123

aagaagaatg agaagatg                                                  18


<210> SEQ ID NO 124
<211> LENGTH: 18
<212> TYPE: DNA
<213> ORGANISM: Artificial
<220> FEATURE:
<223> OTHER INFORMATION: Chemically synthesized oligonucleotide (zinc
      finger protein target)

<400> SEQUENCE: 124
```

-continued ccggagtcac tggtggag 18

<210> SEQ ID NO 125
<211> LENGTH: 18
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 125
gcatagggag cagaagga 18

<210> SEQ ID NO 126
<211> LENGTH: 19
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 126
ggaggcccca ggccagagg 19

<210> SEQ ID NO 127
<211> LENGTH: 18
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 127
tagtgggttt ataaaatg 18

<210> SEQ ID NO 128
<211> LENGTH: 19
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 128
ctactggaat gtgtgcctg 19

<210> SEQ ID NO 129
<211> LENGTH: 19
<212> TYPE: DNA
<213> ORGANISM: Artificial
<220> FEATURE:
<223> OTHER INFORMATION: Chemically synthesized oligonucleotide (zinc finger protein binding domain)

<400> SEQUENCE: 129
aagaaggctg cagacacag 19

<210> SEQ ID NO 130
<211> LENGTH: 18
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 130
agactgaacc tggaggtc 18

-continued

<210> SEQ ID NO 131
<211> LENGTH: 18
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 131
aacttggagg tccaaatg 18

<210> SEQ ID NO 132
<211> LENGTH: 18
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 132
aatctggtgg tggtggta 18

<210> SEQ ID NO 133
<211> LENGTH: 18
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 133
cccagggcca aggaggac 18

<210> SEQ ID NO 134
<211> LENGTH: 19
<212> TYPE: DNA
<213> ORGANISM: Artificial
<220> FEATURE:
<223> OTHER INFORMATION: Chemically synthesized oligonucleotide (zinc finger protein target)

<400> SEQUENCE: 134
gcagagcttt cagggaaag 19

<210> SEQ ID NO 135
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 135

Ala Asn His His Arg Ile Asn
1 5

<210> SEQ ID NO 136
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 136

Gln Ser Ala Val Leu Thr Glu

-continued 1 5

<210> SEQ ID NO 137
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 137

Gln Ser Gln His Leu Thr Arg
1 5

<210> SEQ ID NO 138
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 138

Arg Ser Asp Ser Leu Ser Val
1 5

<210> SEQ ID NO 139
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 139

Arg Asn Gln Asp Arg Lys Asn
1 5

<210> SEQ ID NO 140
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 140

Thr Ser His Ala Leu Thr Gln
1 5

<210> SEQ ID NO 141
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 141

Asp Ser Ala His Leu Ser Arg
1 5

<210> SEQ ID NO 142
<211> LENGTH: 7
<212> TYPE: PRT
<213> ORGANISM: Artificial
<220> FEATURE:
<223> OTHER INFORMATION: Chemically synthesized peptide (zinc finger -continued protein binding domain)

<400> SEQUENCE: 142

Thr Ser Ala His Arg Ile Lys
1 5

<210> SEQ ID NO 143
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 143

Gln Lys Asp Ser Arg Lys Asn
1 5

<210> SEQ ID NO 144
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 144

Arg Ser Asp Ala Leu Ser Gln
1 5

<210> SEQ ID NO 145
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 145

Arg Ser Asp His Leu Thr Lys
1 5

<210> SEQ ID NO 146
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 146

Asn Ser Asp His Leu Ser Arg
1 5

<210> SEQ ID NO 147
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 147

Arg Ser Asp Thr Leu Ser Val
1 5

<210> SEQ ID NO 148

-continued

<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 148

Asp Asn Ser Thr Arg Ile Lys
1 5

<210> SEQ ID NO 149
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 149

Ala Ser Asn Asp Arg Lys Lys
1 5

<210> SEQ ID NO 150
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 150

Gln Asn Ala Asn Arg Ile Thr
1 5

<210> SEQ ID NO 151
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 151

Arg Ser Asp His Arg Lys Thr
1 5

<210> SEQ ID NO 152
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 152

Arg Ser Asp His Arg Ile Thr
1 5

<210> SEQ ID NO 153
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 153

-continued

```
Ala Ser Ala His Leu Thr Glu
1               5


<210> SEQ ID NO 154
<211> LENGTH: 7
<212> TYPE: PRT
<213> ORGANISM: Artificial
<220> FEATURE:
<223> OTHER INFORMATION: Chemically synthesized peptide (zinc finger
      protein binding domain)

<400> SEQUENCE: 154

Arg Ser Asp Ala Leu Ser Arg
1               5


<210> SEQ ID NO 155
<211> LENGTH: 7
<212> TYPE: PRT
<213> ORGANISM: Artificial
<220> FEATURE:
<223> OTHER INFORMATION: Chemically synthesized peptide (zinc finger
      protein binding domain)

<400> SEQUENCE: 155

Arg Ser Asp Thr Leu Ser Glu
1               5


<210> SEQ ID NO 156
<211> LENGTH: 7
<212> TYPE: PRT
<213> ORGANISM: Artificial
<220> FEATURE:
<223> OTHER INFORMATION: Chemically synthesized peptide (zinc finger
      protein binding domain)

<400> SEQUENCE: 156

Asn Asn Arg Asp Arg Thr Lys
1               5


<210> SEQ ID NO 157
<211> LENGTH: 7
<212> TYPE: PRT
<213> ORGANISM: Artificial
<220> FEATURE:
<223> OTHER INFORMATION: Chemically synthesized peptide (zinc finger
      protein binding domain)

<400> SEQUENCE: 157

Ser Asn Glu Ala Leu Ile Glu
1               5


<210> SEQ ID NO 158
<211> LENGTH: 7
<212> TYPE: PRT
<213> ORGANISM: Artificial
<220> FEATURE:
<223> OTHER INFORMATION: Chemically synthesized peptide (zinc finger
      protein binding domain)

<400> SEQUENCE: 158

Arg Asn Ser Asp Arg Thr Lys
1               5


<210> SEQ ID NO 159
<211> LENGTH: 7
<212> TYPE: PRT
<213> ORGANISM: Artificial
<220> FEATURE:
```

-continued

<223> OTHER INFORMATION: Chemically synthesized peptide (zinc finger
protein binding domain)

<400> SEQUENCE: 159

Asp Ser Ser His Arg Thr Arg
1 5

<210> SEQ ID NO 160
<211> LENGTH: 7
<212> TYPE: PRT
<213> ORGANISM: Artificial
<220> FEATURE:
<223> OTHER INFORMATION: Chemically synthesized peptide (zinc finger
protein binding domain)

<400> SEQUENCE: 160

Gln Asn Ala Asn Arg Thr Thr
1 5

<210> SEQ ID NO 161
<211> LENGTH: 7
<212> TYPE: PRT
<213> ORGANISM: Artificial
<220> FEATURE:
<223> OTHER INFORMATION: Chemically synthesized peptide (zinc finger
protein binding domain)

<400> SEQUENCE: 161

Arg Ser Asp Ser Leu Ser Asn
1 5

<210> SEQ ID NO 162
<211> LENGTH: 7
<212> TYPE: PRT
<213> ORGANISM: Artificial
<220> FEATURE:
<223> OTHER INFORMATION: Chemically synthesized peptide (zinc finger
protein binding domain)

<400> SEQUENCE: 162

Thr Ser Asn Asn Arg Thr Thr
1 5

<210> SEQ ID NO 163
<211> LENGTH: 7
<212> TYPE: PRT
<213> ORGANISM: Artificial
<220> FEATURE:
<223> OTHER INFORMATION: Chemically synthesized peptide (zinc finger
protein binding domain)

<400> SEQUENCE: 163

Ala Ser Ser Thr Arg Ile Thr
1 5

<210> SEQ ID NO 164
<211> LENGTH: 7
<212> TYPE: PRT
<213> ORGANISM: Artificial
<220> FEATURE:
<223> OTHER INFORMATION: Chemically synthesized peptide (zinc finger
protein binding domain)

<400> SEQUENCE: 164

Arg Ser Asp Val Leu Ser Ala
1 5

-continued

<210> SEQ ID NO 165
<211> LENGTH: 7
<212> TYPE: PRT
<213> ORGANISM: Artificial
<220> FEATURE:
<223> OTHER INFORMATION: Chemically synthesized peptide (zinc finger
      protein binding domain)

<400> SEQUENCE: 165

Gln Asn Gln His Arg Ile Asn
1               5

<210> SEQ ID NO 166
<211> LENGTH: 7
<212> TYPE: PRT
<213> ORGANISM: Artificial
<220> FEATURE:
<223> OTHER INFORMATION: Chemically synthesized peptide (zinc finger
      protein binding domain)

<400> SEQUENCE: 166

Arg Ser Asp Asn Leu Ala Arg
1               5

<210> SEQ ID NO 167
<211> LENGTH: 7
<212> TYPE: PRT
<213> ORGANISM: Artificial
<220> FEATURE:
<223> OTHER INFORMATION: Chemically synthesized peptide (zinc finger
      protein binding domain)

<400> SEQUENCE: 167

Thr Ser Gly His Leu Ser Arg
1               5

<210> SEQ ID NO 168
<211> LENGTH: 7
<212> TYPE: PRT
<213> ORGANISM: Artificial
<220> FEATURE:
<223> OTHER INFORMATION: Chemically synthesized peptide (zinc finger
      protein binding domain)

<400> SEQUENCE: 168

Ala Asn Ser Asn Arg Ile Lys
1               5

<210> SEQ ID NO 169
<211> LENGTH: 7
<212> TYPE: PRT
<213> ORGANISM: Artificial
<220> FEATURE:
<223> OTHER INFORMATION: Chemically synthesized peptide (zinc finger
      protein binding domain)

<400> SEQUENCE: 169

Arg Ser His Asp Leu Ile Glu
1               5

<210> SEQ ID NO 170
<211> LENGTH: 7
<212> TYPE: PRT
<213> ORGANISM: Artificial
<220> FEATURE:
<223> OTHER INFORMATION: Chemically synthesized peptide (zinc finger
      protein binding domain)

<400> SEQUENCE: 170

Gln Ser Ala Asn Arg Thr Thr
1 5

<210> SEQ ID NO 171
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 171

Gln Ser Gly Asp Leu Thr Arg
1 5

<210> SEQ ID NO 172
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 172

Arg Ser Asp Ser Leu Ser Lys
1 5

<210> SEQ ID NO 173
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 173

Arg Ser Ala Asp Arg Thr Lys
1 5

<210> SEQ ID NO 174
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 174

Thr Arg Ala Ser Arg Ile Thr
1 5

<210> SEQ ID NO 175
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 175

Thr Asn Gln Asn Arg Ile Thr
1 5

<210> SEQ ID NO 176
<211> LENGTH: 7
<212> TYPE: PRT
<213> ORGANISM: Artificial

-continued

<220> FEATURE:
<223> OTHER INFORMATION: Chemically synthesized peptide (zinc finger protein binding domain)

<400> SEQUENCE: 176

Gln Ser Gly Asn Leu Ala Arg
1 5

<210> SEQ ID NO 177
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 177

Arg Lys Asp Thr Arg Ile Thr
1 5

<210> SEQ ID NO 178
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 178

Arg Ser Asp Ala Leu Ala Arg
1 5

<210> SEQ ID NO 179
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 179

Arg Asn Gln Asp Arg Thr Asn
1 5

<210> SEQ ID NO 180
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 180

Gln Ser Gly His Leu Gln Arg
1 5

<210> SEQ ID NO 181
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 181

Gln Ser Gly His Leu Ser Arg
1 5

-continued

<210> SEQ ID NO 182
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 182

Gln Ser Ala Thr Arg Lys Lys
1 5

<210> SEQ ID NO 183
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 183

Arg Asn Ala Asp Arg Lys Thr
1 5

<210> SEQ ID NO 184
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 184

Asp Asn Arg Asp Arg Ile Lys
1 5

<210> SEQ ID NO 185
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 185

Asp Ser Ala Ala Leu Thr Ala
1 5

<210> SEQ ID NO 186
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 186

Arg Ser Asp Thr Leu Ser Ala
1 5

<210> SEQ ID NO 187
<211> LENGTH: 7
<212> TYPE: PRT
<213> ORGANISM: Artificial
<220> FEATURE:
<223> OTHER INFORMATION: Chemically synthesized peptide (zinc finger protein binding domain)

-continued

<400> SEQUENCE: 187

Gln Asn Ala Asn Arg Lys Thr
1 5

<210> SEQ ID NO 188
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 188

Ala Lys Ser Glu Leu Asn Thr
1 5

<210> SEQ ID NO 189
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 189

Thr Ser Ala Asn Arg Thr Thr
1 5

<210> SEQ ID NO 190
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 190

Arg Ser Asp Ala Leu Ser Thr
1 5

<210> SEQ ID NO 191
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 191

Ala Ser Ser Asn Arg Ile Lys
1 5

<210> SEQ ID NO 192
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 192

Arg Ser Asp Val Leu Ser Gln
1 5

<210> SEQ ID NO 193
<211> LENGTH: 7
<212> TYPE: PRT

-continued

<213> ORGANISM: Artificial
<220> FEATURE:
<223> OTHER INFORMATION: Chemically synthesized peptide (zinc finger protein binding domain)

<400> SEQUENCE: 193

Thr Ser Ser Asn Arg Lys Thr
1 5

<210> SEQ ID NO 194
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 194

Asp Asn Ser Asn Arg Ile Asn
1 5

<210> SEQ ID NO 195
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 195

Gln Ser Ala Ser Arg Lys Asn
1 5

<210> SEQ ID NO 196
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 196

Gln Ser Ser Asp Leu Arg Arg
1 5

<210> SEQ ID NO 197
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 197

Asp Arg Ser Ala Leu Ser Arg
1 5

<210> SEQ ID NO 198
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 198

Arg Ser Asp Asn Leu Thr Arg
1 5

-continued

<210> SEQ ID NO 199
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 199

Arg Ser Asp Ser Leu Ser Thr
1 5

<210> SEQ ID NO 200
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 200

Asp Ser Ser Asn Arg Ile Thr
1 5

<210> SEQ ID NO 201
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 201

Gln Asn Ala His Arg Lys Thr
1 5

<210> SEQ ID NO 202
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 202

Asp Arg Ser Asn Arg Lys Thr
1 5

<210> SEQ ID NO 203
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 203

Gln Ser Gly Ala Leu Ala Arg
1 5

<210> SEQ ID NO 204
<211> LENGTH: 7
<212> TYPE: PRT
<213> ORGANISM: Artificial
<220> FEATURE:
<223> OTHER INFORMATION: Chemically synthesized peptide (zinc finger protein binding domain)

-continued

<400> SEQUENCE: 204

Thr Lys Ser Asn Arg Thr Thr
1 5

<210> SEQ ID NO 205
<211> LENGTH: 7
<212> TYPE: PRT
<213> ORGANISM: Artificial
<220> FEATURE:
<223> OTHER INFORMATION: Chemically synthesized peptide (zinc finger protein binding domain)

<400> SEQUENCE: 205

Asp Arg Ser Asn Leu Ser Arg
1 5

<210> SEQ ID NO 206
<211> LENGTH: 5
<212> TYPE: PRT
<213> ORGANISM: Artificial
<220> FEATURE:
<223> OTHER INFORMATION: Chemically synthesized peptide (peptide linker)

<400> SEQUENCE: 206

Thr Gly Glu Lys Pro
1 5

<210> SEQ ID NO 207
<211> LENGTH: 5
<212> TYPE: PRT
<213> ORGANISM: Artificial
<220> FEATURE:
<223> OTHER INFORMATION: Chemically synthesized peptide (peptide linker)

<400> SEQUENCE: 207

Gly Gly Gly Gly Ser
1 5

<210> SEQ ID NO 208
<211> LENGTH: 8
<212> TYPE: PRT
<213> ORGANISM: Artificial
<220> FEATURE:
<223> OTHER INFORMATION: Chemically synthesized peptide (peptide linker)

<400> SEQUENCE: 208

Gly Gly Arg Arg Gly Gly Gly Ser
1 5

<210> SEQ ID NO 209
<211> LENGTH: 9
<212> TYPE: PRT
<213> ORGANISM: Artificial
<220> FEATURE:
<223> OTHER INFORMATION: Chemically synthesized peptide (peptide linker)

<400> SEQUENCE: 209

Leu Arg Gln Arg Asp Gly Glu Arg Pro
1 5

<210> SEQ ID NO 210
<211> LENGTH: 12
<212> TYPE: PRT
<213> ORGANISM: Artificial
<220> FEATURE:
<223> OTHER INFORMATION: Chemically synthesized peptide (peptide linker)

<400> SEQUENCE: 210

Leu Arg Gln Lys Asp Gly Gly Gly Ser Glu Arg Pro
1 5 10

<210> SEQ ID NO 211
<211> LENGTH: 16
<212> TYPE: PRT
<213> ORGANISM: Artificial
<220> FEATURE:
<223> OTHER INFORMATION: Chemically synthesized peptide (peptide linker)

<400> SEQUENCE: 211

Leu Arg Gln Lys Asp Gly Gly Gly Ser Gly Gly Gly Ser Glu Arg Pro
1 5 10 15

<210> SEQ ID NO 212
<211> LENGTH: 30
<212> TYPE: PRT
<213> ORGANISM: Artificial
<220> FEATURE:
<223> OTHER INFORMATION: Chemically synthesized peptide (DNA binding domain)

<400> SEQUENCE: 212

Tyr Ala Cys Pro Val Glu Ser Cys Asp Arg Arg Phe Ser Arg Ser Asp
1 5 10 15

Glu Leu Thr Arg His Ile Arg Ile His Thr Gly Gln Lys Pro
20 25 30

<210> SEQ ID NO 213
<211> LENGTH: 28
<212> TYPE: PRT
<213> ORGANISM: Artificial
<220> FEATURE:
<223> OTHER INFORMATION: Chemically synthesized peptide (DNA binding domain)

<400> SEQUENCE: 213

Phe Gln Cys Arg Ile Cys Met Arg Asn Phe Ser Arg Ser Asp His Leu
1 5 10 15

Thr Thr His Ile Arg Thr His Thr Gly Glu Lys Pro
20 25

<210> SEQ ID NO 214
<211> LENGTH: 27
<212> TYPE: PRT
<213> ORGANISM: Artificial
<220> FEATURE:
<223> OTHER INFORMATION: Chemically synthesized peptide (DNA binding domain)

<400> SEQUENCE: 214

Phe Ala Cys Asp Ile Cys Gly Arg Lys Phe Ala Arg Ser Asp Glu Arg
1 5 10 15

Lys Arg His Thr Lys Ile His Leu Arg Gln Lys
20 25

<210> SEQ ID NO 215
<211> LENGTH: 22
<212> TYPE: DNA
<213> ORGANISM: Artificial
<220> FEATURE:
<223> OTHER INFORMATION: Chemically synthesized oligonucleotide (zinc finger protein target sequence)

-continued

<400> SEQUENCE: 215
ttccgataac gaacgagact ct 22

<210> SEQ ID NO 216
<211> LENGTH: 19
<212> TYPE: DNA
<213> ORGANISM: Artificial
<220> FEATURE:
<223> OTHER INFORMATION: Reverse transcriptase PCR primer

<400> SEQUENCE: 216
tggctgaacg ccacttgtc 19

<210> SEQ ID NO 217
<211> LENGTH: 24
<212> TYPE: DNA
<213> ORGANISM: Artificial
<220> FEATURE:
<223> OTHER INFORMATION: Reverse transcriptase PCR primer

<400> SEQUENCE: 217
taactagtta cgcgaccccc cgag 24

<210> SEQ ID NO 218
<211> LENGTH: 23
<212> TYPE: DNA
<213> ORGANISM: Artificial
<220> FEATURE:
<223> OTHER INFORMATION: Reverse transcriptase probe

<400> SEQUENCE: 218
cctgtgaaaa gaactcggtt ctg 23

<210> SEQ ID NO 219
<211> LENGTH: 21
<212> TYPE: DNA
<213> ORGANISM: Artificial
<220> FEATURE:
<223> OTHER INFORMATION: Reverse transcriptase PCR primer

<400> SEQUENCE: 219
tccacgagaa gcatgtcatg a 21

<210> SEQ ID NO 220
<211> LENGTH: 27
<212> TYPE: DNA
<213> ORGANISM: Artificial
<220> FEATURE:
<223> OTHER INFORMATION: Reverse transcriptase PCR primer

<400> SEQUENCE: 220
tcgcttacag cagcagtgag accccta 27

<210> SEQ ID NO 221
<211> LENGTH: 24
<212> TYPE: DNA
<213> ORGANISM: Artificial
<220> FEATURE:
<223> OTHER INFORMATION: Reverse transcriptase probe

<400> SEQUENCE: 221
catggagaac ccacagtact tcag 24

<210> SEQ ID NO 222
<211> LENGTH: 21

-continued

```
<212> TYPE: DNA
<213> ORGANISM: Artificial
<220> FEATURE:
<223> OTHER INFORMATION: Reverse transcriptase PCR primer

<400> SEQUENCE: 222

cccctagctc ccacttgaga a                                              21


<210> SEQ ID NO 223
<211> LENGTH: 26
<212> TYPE: DNA
<213> ORGANISM: Artificial
<220> FEATURE:
<223> OTHER INFORMATION: Reverse transcriptase PCR primer

<400> SEQUENCE: 223

acctgtgtcc accatatcaa gcgcca                                         26


<210> SEQ ID NO 224
<211> LENGTH: 22
<212> TYPE: DNA
<213> ORGANISM: Artificial
<220> FEATURE:
<223> OTHER INFORMATION: Reverse transcriptase probe

<400> SEQUENCE: 224

tcttcttcac cacctacatc at                                             22


<210> SEQ ID NO 225
<211> LENGTH: 21
<212> TYPE: DNA
<213> ORGANISM: Artificial
<220> FEATURE:
<223> OTHER INFORMATION: Reverse transcriptase PCR primer

<400> SEQUENCE: 225

ccaggtctca tagaacatgt c                                              21


<210> SEQ ID NO 226
<211> LENGTH: 25
<212> TYPE: DNA
<213> ORGANISM: Artificial
<220> FEATURE:
<223> OTHER INFORMATION: Reverse transcriptase PCR primer

<400> SEQUENCE: 226

ccttcctcat cgtggtcaac atgta                                          25


<210> SEQ ID NO 227
<211> LENGTH: 7
<212> TYPE: PRT
<213> ORGANISM: Artificial
<220> FEATURE:
<223> OTHER INFORMATION: Reverse transcriptase probe

<400> SEQUENCE: 227

Ala Lys His His Arg Lys Thr
1               5
```